United States Patent
Liu et al.

(10) Patent No.: US 8,877,822 B2
(45) Date of Patent: Nov. 4, 2014

(54) POROGEN COMPOSITIONS, METHODS OF MAKING AND USES

(75) Inventors: Futian Liu, Sunnyvale, CA (US); Nicholas J. Manesis, Summerland, CA (US); Xiaojie Yu, Irvine, CA (US); Athene Wan Chie Chan, South San Francisco, CA (US)

(73) Assignee: Allergan, Inc., Irvine, CA (US)

( * ) Notice: Subject to any disclaimer, the term of this patent is extended or adjusted under 35 U.S.C. 154(b) by 306 days.

(21) Appl. No.: 13/246,568

(22) Filed: Sep. 27, 2011

(65) Prior Publication Data

US 2012/0077891 A1    Mar. 29, 2012

Related U.S. Application Data

(60) Provisional application No. 61/387,083, filed on Sep. 28, 2010.

(51) Int. Cl.
- *C08J 9/14* (2006.01)
- *B05D 3/00* (2006.01)
- *A61L 27/56* (2006.01)
- *C08J 9/26* (2006.01)

(52) U.S. Cl.
CPC .............. *A61L 27/56* (2013.01); *C08J 2383/04* (2013.01); *C08J 2207/10* (2013.01); *C08J 2207/12* (2013.01); *C08J 2201/05* (2013.01); *C08J 2201/042* (2013.01); *C08J 2201/04* (2013.01); *C08J 2201/0462* (2013.01); *C08J 9/26* (2013.01); *C08J 2201/0422* (2013.01); *A61L 2400/08* (2013.01)
USPC ............... 521/61; 521/82; 521/146; 521/148; 521/154

(58) Field of Classification Search
CPC .... C08J 9/26; C08J 2201/04; C08J 2201/042; C08J 2201/0422; C08J 2201/046; C08J 2201/0462; C08J 2201/05; C08J 2207/10; C08J 2207/12; C08J 2383/04; A61L 27/56; A61L 2400/08
USPC ............................... 521/61, 82, 146, 148, 154
See application file for complete search history.

(56) References Cited

U.S. PATENT DOCUMENTS

| | | | |
|---|---|---|---|
| 2,324,735 A | 1/1941 | Spanel | |
| 2,805,208 A | 9/1957 | Roche | |
| 3,189,921 A | 6/1965 | Pangman | |
| 3,293,663 A | 12/1966 | Cronin | |
| 3,366,975 A | 2/1968 | Pangman | |
| 3,559,214 A | 2/1971 | Pangman | |
| 3,600,718 A | 8/1971 | Boone | |
| 3,665,520 A | 5/1972 | Perras | |
| 3,700,380 A | 10/1972 | Kitrilakis | |
| 3,852,832 A | 12/1974 | McGhan | |
| 3,934,274 A | 1/1976 | Hartley, Jr. | |
| 4,034,751 A | 7/1977 | Hung | |
| 4,157,085 A | 6/1979 | Austad | |
| 4,231,979 A | 11/1980 | White | |
| 4,237,237 A | 12/1980 | Jarre et al. | |
| 4,264,990 A | 5/1981 | Hamas | |
| 4,298,997 A | 11/1981 | Rybka | |
| 4,298,998 A | 11/1981 | Naficy | |
| 4,329,385 A | 5/1982 | Banks | |
| 4,428,082 A | 1/1984 | Naficy | |
| 4,433,440 A | 2/1984 | Cohen | |
| 4,470,160 A | 9/1984 | Cavon | |
| 4,482,577 A | 11/1984 | Goldstein | |
| 4,499,211 A | 2/1985 | Walch | |
| 4,531,244 A | 7/1985 | Hamas | |
| 4,573,999 A | 3/1986 | Netto | |
| 4,584,324 A | 4/1986 | Baumann et al. | |
| 4,592,755 A | 6/1986 | Penton | |
| 4,608,396 A | 8/1986 | Bauman et al. | |
| 4,610,690 A | 9/1986 | Tiffamy | |
| 4,636,213 A | 1/1987 | Pakiam | |
| 4,643,733 A | 2/1987 | Becker | |
| 4,647,618 A | 3/1987 | Baumann et al. | |
| 4,648,880 A | 3/1987 | Brauman | |
| 4,650,487 A | 3/1987 | Chaglassian | |
| 4,651,717 A | 3/1987 | Jakubczak | |
| 4,681,587 A | 7/1987 | Eberl | |
| 4,740,208 A | 4/1988 | Cavon | |
| 4,772,285 A | 9/1988 | Ksander | |
| 4,773,908 A | 9/1988 | Becker | |
| 4,773,909 A | 9/1988 | Chaglassian | |

(Continued)

FOREIGN PATENT DOCUMENTS

| | | |
|---|---|---|
| EP | 0230672 | 8/1987 |
| EP | 0315814 | 5/1989 |

(Continued)

OTHER PUBLICATIONS

Alvarez, Sonia et al., "Synthesis of Macro/Mesoporous Silica and Carbon Monoliths by Using a Commercial Polyurethane Foam as Sacrificial Template", Materials Letters, 61, 2378-2381 (2007).
Barr, S. et al., "Current Implant Surface Technology: An Examination of Their Nanostructure and Their Influence on Fibroblast Alignment and Biocompatibility", Elastic, 2009, 9, 198-217.
Barnsley, Philip et al., "Textured Surface Breast Implants in the Prevention of Capsular Contracture Among Breast Augmentation Patients: A Meta-Analysis of Randomized Controlled Trials", Plastic and Reconstructive Surgery, 2006, 117(7), 2182-2190.
Inamed Aesthetics Brochure, Directions fo Use Style 410 Silicone-Filled Breast Implants (2003).
Ma, Peter, "Scaffolds for tissue fabrication", Materials Today, 2004, 7, 30-40.
Mikes, Antonius et al., "Formation of Highly Porous Biodegradable Scaffolds for Tissue Engineering", Electronic Journal of Biotechnology, 2000, 3(2), 114-119.

(Continued)

*Primary Examiner* — Irina S Zemel
(74) *Attorney, Agent, or Firm* — Linda Allyson Fox

(57) ABSTRACT

Provided are porogen compositions and methods of using such porogen compositions in the manufacture of porous materials, for example, porous silicone elastomers. The porogens generally include comprising a core material and shell material different from the core material. The porogens can be used to form a scaffold for making a resulting porous elastomer when the scaffold is removed.

6 Claims, 5 Drawing Sheets

(56) References Cited

U.S. PATENT DOCUMENTS

| | | |
|---|---|---|
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan |
| 4,965,430 A | 10/1990 | Curtis |
| 4,969,899 A | 11/1990 | Cox, Jr. |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan |
| 5,026,394 A | 6/1991 | Baker |
| 5,034,422 A | 7/1991 | Triolo |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,128,088 A | 7/1992 | Shimomura et al. |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iverson |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| RE35,391 E | 12/1996 | Brauman |
| 5,589,176 A | 12/1996 | Seare |
| 5,605,693 A | 2/1997 | Seare |
| 5,607,473 A | 3/1997 | Weber-Unger |
| 5,624,674 A | 4/1997 | Seare, Jr. |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare, Jr. |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker |
| 5,935,164 A | 8/1999 | Iversen |
| 5,961,552 A | 10/1999 | Iversen |
| 5,964,803 A | 10/1999 | Iversen |
| 5,965,076 A | 10/1999 | Banks |
| 5,984,943 A | 11/1999 | Young |
| 5,993,716 A | 11/1999 | Draenert |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. |
| 6,214,926 B1 | 4/2001 | Winn |
| 6,315,796 B1 | 11/2001 | Eaton |
| 6,340,648 B1 | 1/2002 | Imura et al. |
| 6,387,133 B1 | 5/2002 | Perouse |
| 6,432,138 B1 | 8/2002 | Offray |
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson |
| 6,602,452 B2 | 8/2003 | Schuessler |
| 6,605,116 B2 | 8/2003 | Falcon |
| 6,638,308 B2 | 10/2003 | Corbitt, Jr. |
| 6,673,285 B2 | 1/2004 | Ma |
| 6,692,527 B1 | 2/2004 | Bellin |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt, Jr. |
| 6,900,055 B1 | 5/2005 | Fuller |
| 6,913,626 B2 | 7/2005 | McGhan |
| 6,916,339 B1 | 7/2005 | Missana |
| 6,921,418 B2 | 7/2005 | Ledergerber |
| 6,932,840 B1 | 8/2005 | Bretz |
| 7,056,840 B2 * | 6/2006 | Miller et al. .................. 438/781 |
| 7,081,135 B2 | 7/2006 | Smith et al. |
| 7,081,136 B2 | 7/2006 | Becker |
| 7,105,116 B2 | 9/2006 | Bellin |
| 7,169,180 B2 | 1/2007 | Brennan |
| 7,192,450 B2 | 3/2007 | Brauker |
| 7,244,270 B2 | 7/2007 | Lesh |
| 7,323,208 B2 | 1/2008 | Ma |
| 7,476,249 B2 | 1/2009 | Frank |
| 7,520,896 B2 | 4/2009 | Benslimane |
| 7,547,393 B2 | 6/2009 | Ramaswamy |
| 7,625,405 B2 | 12/2009 | Purkait |
| 7,632,228 B2 | 12/2009 | Brauker |
| 7,632,291 B2 | 12/2009 | Stephens |
| 7,641,688 B2 | 1/2010 | Lesh |
| 7,645,475 B2 | 1/2010 | Prewett |
| 8,202,317 B2 | 6/2012 | Becker |
| 8,313,527 B2 | 11/2012 | Powell et al. |
| 8,487,012 B2 | 7/2013 | Goraltchouk et al. |
| 8,506,627 B2 | 8/2013 | Van Epps et al. |
| 8,546,458 B2 | 10/2013 | Thompson et al. |
| 8,679,279 B2 | 3/2014 | Thompson et al. |
| 8,679,570 B2 | 3/2014 | Goraltchouk et al. |
| 8,685,296 B2 | 4/2014 | Liu et al. |
| 8,697,763 B2 | 4/2014 | Goraltchouk et al. |

(56) References Cited

U.S. PATENT DOCUMENTS

| | | |
|---|---|---|
| 2002/0038147 A1 | 3/2002 | Miller |
| 2002/0193885 A1 | 12/2002 | Legeay |
| 2003/0036803 A1 | 2/2003 | McGhan |
| 2003/0093151 A1 | 5/2003 | Zhang |
| 2003/0105469 A1 | 6/2003 | Karmon |
| 2003/0205846 A1 | 11/2003 | Bellin |
| 2003/0208269 A1 | 11/2003 | Eaton |
| 2004/0010225 A1 | 1/2004 | Schuessler |
| 2004/0115241 A1 | 6/2004 | Calhoun |
| 2004/0127985 A1 | 7/2004 | Bellin |
| 2004/0143327 A1 | 7/2004 | Ku |
| 2004/0148024 A1 | 7/2004 | Williams |
| 2004/0153151 A1 | 8/2004 | Gonzalez |
| 2004/0176493 A1 | 9/2004 | Ferguson |
| 2004/0213986 A1 | 10/2004 | Kim |
| 2005/0055093 A1 | 3/2005 | Brennan |
| 2005/0070124 A1 | 3/2005 | Miller |
| 2005/0112169 A1 | 5/2005 | Brauker |
| 2005/0122169 A1 | 6/2005 | Watanabe |
| 2005/0196452 A1 | 9/2005 | Boyan et al. |
| 2005/0216094 A1 | 9/2005 | Prewett |
| 2005/0251083 A1 | 11/2005 | Carr-Brendel et al. |
| 2006/0002810 A1 | 1/2006 | Grohowski |
| 2006/0036266 A1 | 2/2006 | Sulmandize et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2007/0093911 A1 | 4/2007 | Fricke |
| 2007/0104693 A1 | 5/2007 | Quijano |
| 2007/0104695 A1 | 5/2007 | Quijano |
| 2007/0116735 A1 | 5/2007 | Calhoun |
| 2007/0135916 A1 | 6/2007 | Maxwell |
| 2007/0154525 A1 | 7/2007 | Calhoun |
| 2007/0190108 A1 | 8/2007 | Datta et al. |
| 2007/0198085 A1 | 8/2007 | Benslimane |
| 2008/0009830 A1 | 1/2008 | Fujimoto |
| 2008/0058499 A1* | 3/2008 | Fukazawa et al. ............ 528/395 |
| 2008/0071371 A1 | 3/2008 | Elshout |
| 2008/0075752 A1 | 3/2008 | Ratner |
| 2008/0154366 A1 | 6/2008 | Frank |
| 2008/0241212 A1 | 10/2008 | Moses |
| 2008/0268019 A1 | 10/2008 | Badylak |
| 2008/0312739 A1 | 12/2008 | Agerup |
| 2009/0045166 A1 | 2/2009 | Li |
| 2009/0082864 A1 | 3/2009 | Chen |
| 2009/0087641 A1 | 4/2009 | Favis |
| 2009/0093878 A1 | 4/2009 | Glicksman |
| 2009/0118829 A1 | 5/2009 | Powell |
| 2009/0125107 A1 | 5/2009 | Maxwell |
| 2009/0169716 A1 | 7/2009 | Linhardt |
| 2009/0198331 A1 | 8/2009 | Kesten et al. |
| 2009/0198332 A1 | 8/2009 | Becker |
| 2009/0198333 A1 | 8/2009 | Becker |
| 2010/0042211 A1 | 2/2010 | Van Epps et al. |
| 2010/0292790 A1 | 11/2010 | Stroumpoulis et al. |
| 2011/0054605 A1 | 3/2011 | Becker |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0196488 A1 | 8/2011 | Goralthcouk et al. |
| 2011/0196489 A1 | 8/2011 | Van Epps et al. |
| 2011/0276133 A1 | 11/2011 | Liu et al. |
| 2011/0276134 A1 | 11/2011 | Manesis et al. |
| 2011/0282444 A1 | 11/2011 | Liu et al. |
| 2011/0309541 A1 | 12/2011 | Thompson et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077012 A1 | 3/2012 | Liu et al. |
| 2012/0101574 A1 | 4/2012 | Goralthchouk et al. |
| 2012/0245685 A1 | 9/2012 | Yu |
| 2012/0321777 A1 | 12/2012 | Stroumpoulis et al. |
| 2013/0023987 A1 | 1/2013 | Liu et al. |
| 2013/0032962 A1 | 2/2013 | Liu et al. |
| 2013/0053956 A1 | 2/2013 | Powell et al. |
| 2013/0158657 A1 | 6/2013 | Nofrey et al. |
| 2013/0245148 A1 | 9/2013 | Thompson et al. |
| 2013/0295379 A1 | 11/2013 | Goraltchouk et al. |
| 2013/0302511 A1 | 11/2013 | Goraltchouk et al. |
| 2013/0310934 A1 | 11/2013 | Van Epps et al. |
| 2014/0003685 A1 | 1/2014 | Van Epps et al. |
| 2014/0005783 A1 | 1/2014 | Van Epps et al. |
| 2014/0005784 A1 | 1/2014 | Van Epps et al. |
| 2014/0094662 A1 | 4/2014 | Van Epps et al. |
| 2014/0154491 A1 | 6/2014 | Goraltchouk et al. |
| 2014/0154508 A1 | 6/2014 | Liu et al. |
| 2014/0156002 A1 | 6/2014 | Thompson et al. |

FOREIGN PATENT DOCUMENTS

| | | |
|---|---|---|
| EP | 0522585 | 5/2005 |
| EP | 1532942 | 5/2005 |
| FR | 2840617 | 12/2003 |
| JP | 2003-062062 | 4/2003 |
| JP | 2007-029717 | 8/2007 |
| WO | WO 98/10803 | 3/1998 |
| WO | WO 00/24437 | 5/2000 |
| WO | WO 2004/037318 | 5/2004 |
| WO | WO 2004/062531 | 7/2004 |
| WO | 2006/133366 | 12/2006 |
| WO | WO 2009/061672 | 5/2009 |
| WO | WO 2009/110917 | 9/2009 |
| WO | WO 2011/094155 | 8/2011 |
| WO | WO 2011/097499 | 8/2011 |

OTHER PUBLICATIONS

Minami, Eliza et al., "The Composition and Behavior of Capsules Around Smooth and Textured Breast Implants in Pigs", Plastic and Reconstructive Surgery, 2006, 118940, 874-884.

Murphy, William et al., "Salt Fusion: An Approach to Improve Pore Interconnectivity Within Tissue Engineering Scaffolds", Tissue Engineering, vol. 8, Iss. 1, 2004.

Wei, Guobao et al., "Macroporous and Nanofibers Polymer Scaffolds and Polymer/bone-like Apatite Composite Scaffolds Generated by Sugar Spheres", Journal of Biomedical Materials Research Part A, 2006, 306-315.

Zhang, Yuan et al., "Macroporous Alumina Monoliths Prepared by Filling Polymer Foams With Alumina Hydrosols", J. Mater Sci., 44, 931-938 (2009).

Brauker et al., "Neovascularization of synthetic membranes directed by membrane microarchitecture", Journal of Biomedical Materials Research, 1995, pp. 1517-1524, vol. 29, John Wiley & Sons, Inc.

Brohim et al., "Early Tissue Reaction to Textured Breast Implant Surfaces", Anals of Plastic Surgery, 28(4): 354-362, 1992.

Sharkawy et al. "Engineering the tissue which encapsulates subcutaneous implants", II Plasma—tissue exchange properties, 1998, pp. 586-597, John Wiley & Sons, Inc.

* cited by examiner

POROGEN COMPOSITIONS, METHODS OF MAKING AND USES

This application claims priority to U.S. Patent Application No. 61/387,083, filed Sep. 28, 2010, the entire of disclosure of which is incorporated herein by this reference.

Porous materials are widely used in biomedical, industrial, and household applications. The present invention provides porous materials useful in numerous varied applications. In the biomedical field, porous materials of the invention can be used as a matrix for tissue engineering/regeneration, wound dressings, drug release matrices, membranes for separations and filtration, sterile filters, artificial kidneys, absorbents, hemostatic devices, and the like. In various industrial and household applications, porous materials of the invention can be used as insulating materials, packaging materials, impact absorbers, liquid or gas absorbents, wound dressings, personal hygiene products, such as but not limited to, cleaning and cleansing pads, wipes and swabs, deodorant, disposable towels, dry shampoo, facial tissues, handkerchiefs, hygiene wipes, paper towels, shaving brushes, tampons, towels, underarm liners, washing mitts, and wet wipes, membranes, filters and so forth.

One conventional method of making a porous material relies on a three-dimensional scaffold used as a negative template. One such example is the porogen scaffold method. In this method, porogens are pored into a mold and treated, such as, e.g., by physical and/or chemical means to fuse the porogens, thereby forming a porogen scaffold comprising fused porogens that are all connected to one another. A material is then poured into the mold to coat the porogen scaffold and this material is then stabilized, such as, e.g., a curing process or a freezing process. After stabilization, the porogen scaffold is removed, leaving behind a porous material. See, e.g., Ma, Reverse Fabrication of Porous Materials, U.S. Patent Publication 2002/0005600; Ratner and Marshall, Novel Porous Materials, U.S. Patent Publication 2008/0075752; Ma and Chen, Porous Materials having Multi-Sized Geometries, U.S. Patent Publication 2007/0036844, each of which is incorporated by reference in its entirety.

Conventionally, the porogens used to make the porogen scaffolds are composed of a single material, such as, e.g., gelatin, sucrose, or poly(lactide-co-glycolide). However, the physical and/or chemical treatment to fuse the porogens together does not typically result in a uniform fusion of all porogens to form a well-structured porogen scaffold. For example, most porogens are fused using thermal means where the porogens, in the solid phase, are heated to a temperature above the melting point (or glass transition point). At this temperature, the porogens transition to a liquid phase allowing the porogens to melt together. This process is carefully controlled to allow sufficient melting to form the desired numbers of connections. Too short a thermal treatment will result in an insufficient number of porogen fusions, whereas to long a thermal treatment will result in formation of a solid block. However, even though comprised of the same material, not all porogens melt at the same time. So, even under carefully controlled conditions, the resulted porogen scaffold is not uniformly structured.

As such, there is a continuing need for porogens that upon physical and/or chemical treatment, a porogen scaffold of uniformly fused porogens is produced. The present application discloses porogen compositions comprising a shell material and a core material and methods of making these porogen compositions. Upon physical and/or chemical treatment the porogen compositions disclosed herein produce porogen scaffold of uniformly fused porogens.

Thus, aspects of the present specification disclose a porogen composition comprising a shell material and a core material.

Other aspects of the present specification disclose a method of forming a porogen composition, the method comprising the steps of: a) making a particle out of a core material; and b); coating the particle with a shell material.

Yet other aspects of the present specification disclose a method of forming a porous material, the method comprising the steps of: a) fusing porogens disclosed herein to form a porogen scaffold comprising fused porogens; b) coating the porogen scaffold with a material to form an material coated porogen scaffold; c) stabilizing the material coated porogen scaffold; and d) removing the porogen scaffold, wherein porogen scaffold removal results in a porous material, the porous material comprising a matrix defining an array of interconnected pores.

Still other aspects of the present specification disclose a method of forming a porous material, the method comprising the steps of: a) coating porogens disclosed herein with a material to form a material coated porogen mixture; b) treating the material coated porogen mixture to form a porogen scaffold comprising fused porogens and a stabilized material; and c) removing the porogen scaffold for the stabilized material, wherein porogen scaffold removal results in a porous material, the porous material comprising a matrix defining an array of interconnected pores.

Further aspects of the present specification disclose a method of making a device having a porous, textured surface, the method comprising the steps of: a) preparing the surface of a device to receive a porous material; b) attaching a porous material to the prepared surface of the device. The porous material can be made by a method disclosed herein.

Further aspects of the present specification disclose a method for making an article or device including a porous elastomeric surface, the method comprising the step of: a) coating a mandrel with a matrix material base; b) curing the matrix material base to form a base layer; c) coating the cured base layer with a matrix material base; d) coating the matrix material base with porogens to form a matrix material-coated porogen mixture, the porogens comprise a shell material and a core material as disclosed herein; e) treating the matrix material coated porogen mixture to form a porogen scaffold comprising fused porogens and stabilize the matrix material base; and f) removing the porogen scaffold, wherein porogen scaffold removal results in a porous material, the porous material comprising a matrix defining an array of interconnected pores. In this method steps (c) and (d) can be repeated multiple times until the desired thickness of the material layer is achieved.

DETAILED DESCRIPTION

Figure 1:
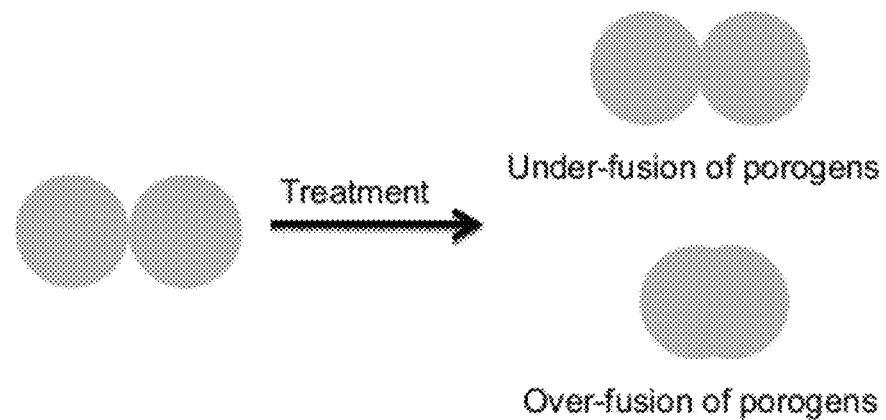
FIG. 1 illustrates a comparison of the use of porogens consisting of a single material, and the use of porogens comprising a shell material and a core material as disclosed herein.
Figure 1:
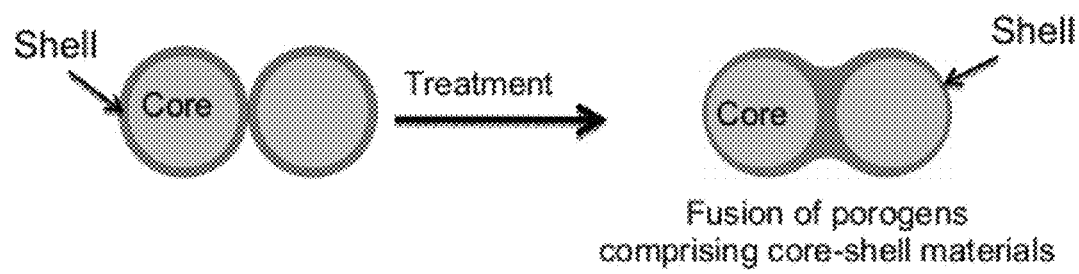

FIG. 1 illustrates a comparison of the use of porogens consisting of a single material, and the use of porogens comprising a shell material and a core material as disclosed herein. Controlled fusion of porogens consisting of a single material is difficult due to the random timing that each porogen transitions from its solid phase to its liquid phase. As such, fusing porogens under a treatment results in insufficient fusion of the porogens (or under-fusion) and/or too much fusion of porogens (over-fusion). Controlled fusion of porogens can be accomplished using the porogen compositions disclosed herein. Treatment is done under conditions that allow the shell material to transition from its solid phase to its liquid phase, but maintain the core material in its solid phase. As such, fusion of porogen compositions disclosed herein result in a more uniform porogen scaffold.

The porogen compositions disclosed herein provide a means to control the degree and amount of fusion that occurs during a formation of a scaffold that can be used to make a porous material, for example, a porous silicone elastomer having a predetermined, clearly defined pore structure. This is accomplished, in part, by providing a shell material and a core material, where the shell material has a lower melting point temperature and/or glass transition temperature relative to the core material. Currently, porogens are composed of a single material. Controlling the fusion of these single material porogens is difficult, due, in part, to the random timing that each individual porogen transitions from its solid phase to its liquid phase. As such, under any given treatment condition designed to cause porogen fusion, there will be a population of porogens that have remained in the solid phase, and yet at the same time, a population of porogens that have completely transitioned into their liquid or rubbery phase (FIG. 1). This unequal or uncontrolled transition from the solid phase to the liquid or rubbery phase results in a porogen scaffold that comprises regions of insufficient porogen fusion (or under-fusion) and/or too much porogen fusion (over-fusion). The uncontrolled nature of the fusion process produces an un-uniform porogen scaffold that ultimately results in porous materials with a matrix of un-uniform pore sizes and interconnections. Such a disorganized structure can reduce the utility of porous materials. The porogen compositions disclosed herein overcome the uncontrollable fusion rates observed in single material porogens. The compositions disclosed herein comprise porogens comprising a shell material and a core material. Controlled fusion of porogens is achieved because fusion treatment is performed under conditions that allow the shell material to transition from its solid phase to its liquid or rubbery phase, but the core material is maintained in its solid phase. As such, fusion of porogen compositions disclosed herein result in a more uniform porogen scaffold (FIG. 1). Thus, a method of making a porous material that utilizes a porogen composition of the present specification will produce a porous material with a more uniform matrix of pore size and interconnections.

The present specification discloses, in part, a porogen composition. As used herein, the term "porogen composition" or "porogen(s)" refers to any structured material that can be used to create a porous material.

Porogens have a shape sufficient to allow formation of a porogen scaffold useful in making a matrix as disclosed herein. Any porogen shape is useful with the proviso that the porogen shape is sufficient to allow formation of a porogen scaffold useful in making a matrix as disclosed herein. Useful porogen shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

In an embodiment, porogens have a shape sufficient to allow formation of a porogen scaffold useful in making a matrix as disclosed herein. In aspects of this embodiment, porogens have a shape that is roughly spherical, perfectly spherical, ellipsoidal, polyhedronal, triangular, pyramidal, quadrilateral, or polygonal.

Porogens have a roundness sufficient to allow formation of a porogen scaffold useful in making a matrix as disclosed herein. As used herein, "roundness" is defined as $(6 \times V)/(\pi \times D^3)$, where V is the volume and D is the diameter. Any porogen roundness is useful with the proviso that the porogen roundness is sufficient to allow formation of a porogen scaffold useful in making a matrix as disclosed herein.

In an embodiment, porogens has a roundness sufficient to allow formation of a porogen scaffold useful in making a matrix as disclosed herein. In aspects of this embodiment, porogens have a mean roundness of, e.g., about 0.1, about 0.2, about 0.3, about 0.4, about 0.5, about 0.6, about 0.7, about 0.8, about 0.9, or about 1.0. In other aspects of this embodiment, porogens have a mean roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, porogens have a mean roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, porogens have a mean roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

A porogen has a thickness sufficient to allow formation of a porogen scaffold. As such, a porogen can be of any thickness, with the proviso that the thickness of the porogen is sufficient to create a porogen scaffold useful for its intended purpose. The thickness of a porogen can be measured base on its shape. For example, for spherical and elliptical porogens, thickness is measured based on the diameter of the core material. For example, for sided-shaped porogens, like polyhedrons, triangles, pyramids, quadrilateral, or polygons, thickness is measured based on the base width of the porogen.

In another embodiment, a porogen comprises mean porogen diameter sufficient to allow formation of a porogen scaffold useful in making a matrix as disclosed herein. In aspects of this embodiment, a porogen comprises mean porogen diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen comprises mean porogen diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen comprises mean porogen diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porogen comprises mean porogen diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen comprises mean porogen diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porogen comprises mean porogen diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen comprises mean porogen diameter of, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porogen comprise mean porogen base sufficient to allow formation of a porogen scaffold useful in making a matrix as disclosed herein. In aspects of this embodiment, a porogen comprises mean porogen base of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen comprises mean porogen base of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen comprises mean porogen base of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porogen comprises mean porogen base of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen comprises mean porogen base of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porogen comprises mean porogen base of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen comprises mean porogen base of, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

The present specification discloses, in part, a porogen comprising a shell material. A shell material of a porogen can be made of any material with the proviso that 1) the melting point temperature (Tm) of the shell material is lower than the melting point temperature of the core material; and/or 2) the glass transition temperature ($T_g$) of the shell material is lower than the glass transition temperature of the core material. As used herein, the term "melting point temperature" or "melting point" refers to the temperature at which the solid and liquid phases of a material exist in equilibrium, at any fixed pressure, and is the temperature at which the first trace of liquid appears. For a matrix material made of a pure substance, the melting, or fusion, process occurs at a single temperature. For a matrix material made of two or more substances, the melting process normally occurs over a range of temperatures, and a distinction is made between the melting point and the freezing point temperature. As used herein, the term "freezing point temperature" or "freezing point" refers to the temperature at which the solid and liquid phases of a matrix material exist in equilibrium, at any fixed pressure, and is the temperature at which the last trace of solid disappears. The freezing point temperature is usually higher than the melting point temperature in matrix materials made from two or more substances.

Amorphous materials, as well as some polymers, do not have a true melting point temperature as there is no abrupt phase change from a solid phase to a liquid phase at any specific temperature. Instead, amorphous materials and polymers exhibit a gradual change in viscoelastic properties over a range of temperatures. Such materials are characterized by vitrification, or glass transition, the process of converting a material into a glassy amorphous solid that is free from crystalline structure. Vitrification occurs at a glass transition temperature. As used herein, the term "glass transition temperature" refers to the temperature at which the glass and liquid phases of an amorphous material exist in equilibrium, at any fixed pressure, and is the temperature that roughly defined the "knee" point of the material's density vs. temperature graph. The glass transition temperature of an amorphous material is lower than its melting temperature.

A shell material can comprise a natural or synthetic, inorganic or organic material. Exemplary materials suitable as a shell material disclosed herein, include, without limitation, natural and synthetic salt and its derivatives, natural and synthetic ceramic and/or its derivatives, natural and synthetic sugar and its derivatives, natural and synthetic polysaccharide and its derivatives, natural and synthetic wax and its derivatives, natural and synthetic metal and its derivatives, natural and synthetic surfactant and its derivatives, natural and synthetic organic solid and its derivatives, natural and synthetic water soluble solid and its derivatives, and/or natural and synthetic polymer and its derivatives, composites thereof, and/or combinations thereof.

A natural or synthetic salt and its derivatives refer to ionic compounds composed of cations and anions so that the product is electrically neutral. The component ions of a salt can be inorganic or organic, as well as, a monoatomic ion or a polyatomic ion. Common salt-forming cations include, without limitation, Ammonium $NH_4^+$, Calcium $Ca^{2+}$, Iron $Fe^{2+}$ and $Fe^{3+}$, Magnesium $Mg^{2+}$, Potassium $K^+$, Pyridinium $C_5H_5NH^+$, Quaternary ammonium $NR_4^+$, and Sodium $Na^+$. Common salt-forming anions include, without limitation, Acetate $CH_3COO^-$, Carbonate $CO_3^{2-}$, Chloride $Cl^-$, Citrate $HOC(COO^-)(CH_2COO^-)_2$, Cyanide $C\equiv N^-$, Hydroxide $OH^-$, Nitrate $NO_3^-$, Nitrite $NO_2^-$, Oxide $O^{2-}$, Phosphate $PO_4^{3-}$, and Sulfate $SO_4^{2-}$. Non-limiting examples of salts include, cobalt chloride hexahydrate, copper sulfate pentahydrate, ferric hexacyanoferrate, lead diacetate, magnesium sulfate, manganese dioxide, mercury sulfide, monosodium glutamate, nickel chloride hexahydrate, potassium bitartrate, potassium chloride, potassium dichromate, potassium fluoride, potassium permanganate, sodium alginate, sodium chromate, sodium chloride, sodium fluoride, sodium iodate, sodium iodide, sodium nitrate, sodium sulfate, and/or mixtures thereof.

A natural or synthetic ceramic and its derivatives refer to inorganic, non-metallic solids that can have a crystalline or partly crystalline structure, or can be amorphous (e.g., a glass). Ceramics include oxides, such as, e.g., alumina and zirconium dioxide, non-oxides, such as, e.g., carbides, borides, nitrides, and silicides; and composites comprising combinations of oxides and non-oxides. Non-limiting examples of salts include, alumina, barium titanate, bismuth strontium calcium copper oxide, boron nitride, lead zirconate titanate, magnesium diboride, silicone aluminium oxynitride, silicone carbide, silicone nitride, strontium titanate, titanium carbide, uranium oxide, yttrium barium copper oxide, zinc oxide, and zirconium dioxide.

A natural or synthetic sugar and its derivatives refer to a compound comprising one to 10 monosaccharide units, e.g., a monosaccharide, a disaccharide, a trisaccharide, and an oligosaccharide comprising four to ten monosaccharide units. Monosaccharides are polyhydroxy aldehydes or polyhydroxy ketones with three or more carbon atoms, including aldoses, dialdoses, aldoketoses, ketoses and diketoses, as well as cyclic forms, deoxy sugars and amino sugars, and their derivatives, provided that the parent monosaccharide has a (potential) carbonyl group. Oligosaccharides are compounds in which at least two monosaccharide units are joined by glycosidic linkages. According to the number of units, they are called disaccharides, trisaccharides, tetrasaccharides, pentasaccharides, hexasaccharides, heptasaccharides, octasaccharides, nonasaccharides, decasaccharides, etc. An oligosaccharide can be unbranched, branched or cyclic. Non-limiting examples of sugars include, monosaccharides, such as, e.g., trioses, like glyceraldehyde and dihydroxyacetone; tetroses, like erythrose, threose and erythrulose; pentoses, like arabinose, lyxose, ribose, xylose, ribulose, xylulose; hexoses, like allose, altrose, galactose, glucose, gulose, idose, mannose, talose, fructose, psicose, sorbose, tagatose, fucose, rhamnose; heptoses, like sedoheptulose and mannoheptulose; octooses, like octulose and 2-keto-3-deoxy-manno-octonate; nonoses like sialose; and decose; and oligosaccharides, such as, e.g., disaccharides, like sucrose, lactose, maltose, trehalose, cellobiose, gentiobiose, kojibiose, laminaribiose, mannobiose, melibiose, nigerose, rutinose, and xylobiose; trisaccharides like raffinose, acarbose, maltotriose, and melezitose and/or mixtures thereof. Sugars also include sugar substitutes like acesulfame potassium, alitame, aspartame, acesulfame, cyclamate, dulcin, glucin, neohesperidin dihydrochalcone, neotame, saccharin, and sucralose.

A natural or synthetic polysaccharide and its derivatives refer to a polymeric carbohydrate compound comprising more than 10 repeating monosaccharide of disaccharide units joined by glycosidic bonds. A polysaccharide can be linear or contain various degrees of branching. Depending on the structure, these macromolecules can have distinct properties from their monosaccharide building blocks. They may be amorphous or even insoluble in water. When all the monosaccharides in a polysaccharide are the same type the polysaccharide is called a homopolysaccharide, but when more than one type of monosaccharide is present they are called heteropolysaccharides. Non-limiting examples of polysaccharides include, amylose; cellulose; cellulose derivatives (like FICOLL, alkyl cellulose, carboxy cellulose, methyl cellulose, carboxymethyl cellulose, hemicellulose, hydroxyethyl cellulose, hydroxypropyl cellulose, hydroxyethyl methyl cellulose, hydroxypropyl methyl cellulose); chitin; chitosan; dextrans (like dextran 1K, dextran 4K, dextran 40K, dextran 60K, and dextran 70K); dextrin; glycogen; inulin; glycosaminoglycans (like chondroitin sulfates, keratin sulfates, heparin sulfates, alginic acid, hyaluronic acid); pectin; pullulan; starch; hetastarch; starch derivatives (like hydroxymethyl starch, hydroxyethyl starch, hydroxypropyl starch, hydroxybutyl starch, and hydroxypentyl starch); xanthan; and salts thereof.

A natural or synthetic wax and its derivatives refer to a type of lipid that contain a wide variety of long-chain alkanes, esters, polyesters and hydroxy esters of long-chain primary alcohols and fatty acids. Waxes are usually distinguished from fats by the lack of triglyceride esters of glycerin(propan-1,2,3-triol) and three fatty acids. Waxes include animal waxes, vegetable waxes, mineral waxes, petroleum waxes, synthetic waxes and/or mixtures thereof. Non-limiting examples of waxes include animal waxes like beeswax, Chinese wax, lanolin (wool wax), shellac wax, spermaceti; vegetable waxes like bayberry wax, candelilla wax, carnauba wax, castor wax, esparto wax, Japan wax, jojoba wax, ouricury wax, rice bran wax, soy wax; mineral waxes like ceresin wax, montan wax, ozocerite, peat wax; petroleum waxes like paraffin wax, microcrystalline wax, petroleum jelly; and synthetic waxes like polyethylene wax, Fischer-Tropsch wax, esterified wax, saponified wax, substituted amide wax, polymerized $\alpha$-olefin wax.

A natural or synthetic metal and its derivatives refer to an element, compound, or alloy characterized by high electrical conductivity. An alloy is a mixture of two or more elements in solid solution in which the major component is a metal. A metal can be a base metal, a ferrous metal, a noble metal, or a precious metal. Non limiting examples of metals include alkali metals, like Lithium, Sodium, Potassium, Rubidium, Caesium, and Francium; alkaline earth metals like Beryllium, Magnesium, Calcium, Strontium, Barium, and Radium; transition metals like Zinc, Molybdenum, Cadmium, Scandium, Titanium, Vanadium, Chromium, Manganese, Iron, Cobalt, Nickel, Copper, Yttrium, Zirconium, Niobium, Technetium, Ruthenium, Rhodium, Palladium, Silver, Hafnium, Tantalum, Tungsten, Rhenium, Osmium, Iridium, Platinum, Gold, Mercury, Rutherfordium, Dubnium, Seaborgium, Bohrium, Hassium, Meitnerium, Darmstadtium, Roentgenium, and Copernicium; post-transition metals like Aluminium, Gallium, Indium, Tin, Thallium, Lead, Bismuth, Ununtrium, Ununquadium, Ununpentium, and Ununhexium; lanthanoids like Lanthanum, Cerium, Praseodymium, Neodymium, Promethium, Samarium, Europium, Gadolinium, Terbium, Dysprosium, Holmium, Erbium, Thulium, Ytterbium, and Lutetium; and actinoids like Actinium, Thorium, Protactinium, Uranium, Neptunium, Plutonium, Americium, Curium, Berkelium, Californium, Einsteinium, Fermium, Mendelevium, Nobelium, and Lawrencium.

A natural or synthetic surfactant and its derivatives refer to organic compounds that are amphiphilic and are soluble in both organic solvents and water. A surfactant includes, without limitation, ionic surfactants like cationic surfactants (based on quaternary ammonium cations) and anionic surfactants (based on sulfate, sulfonate or carboxylate anions), zwitterionic (amphoteric) surfactants, and/or non-ionic surfactants. Non-limiting examples of surfactants include anionic surfactants like perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate, also known as sodium lauryl ether sulfate (SLES), alkyl benzene sulfonate, soaps, and fatty acid salts; cationic surfactants like cetyl trimethylammonium bromide (CTAB), also known as hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); zwitterionic surfactants like dodecyl betaine, cocamidopropyl betaine, coco ampho glycinate; and non-ionic surfactants like sucrose monolaurate, sodium cholate, dodecyl dimethylamine oxide, alkyl naphthalene sulfonates (ANS), alkyl poly(ethylene oxide), alkylphenol poly(ethylene oxide), poly(ethylene oxide) and poly(propylene oxide) co-polymers, also known as Poloxamers or Poloxamines including Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and Poloxamer 407 (PLURONIC® F127), alkyl polyglucosides, including octyl glucoside and decyl maltoside, fatty alcohols including cetyl alcohol and oleyl alcohol, cocamide MEA, cocamide DEA, polysorbates including polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); and 3-[(3-Cholamidopropyl)dimethyl ammonio]-2-hydroxy-1-propanesulfonate (CHAPSO).

A natural or synthetic inorganic solid and its derivatives refer to a mineral not of biological origin. Non-limiting examples of inorganic solids include hydroxyapatite (HAP), carbonated hydroxyapatite, fluorinated hydroxyapatite, various calcium phosphates (CAP), glass, salts, oxides, silicates, and/or the like, and/or mixtures thereof.

A natural or synthetic water-soluble solid and its derivatives refer to any material that can be dissolved in water. Non-limiting examples of inorganic solids include sodium hydroxide and naphthalene.

A natural or synthetic polymer and its derivatives, refer to natural and synthetic macromolecules composed of repeating structural units typically connected by covalent chemical bonds. A polymer includes natural or synthetic hydrophilic polymers, natural or synthetic hydrophobic polymers, natural or synthetic amphiphilic polymers, degradable polymers, partially degradable polymers, non-degradable polymers, and combinations thereof. Polymers may be homopolymers or copolymers. Copolymers may be random copolymers, blocked copolymers, graft copolymers, and/or mixtures thereof. Non-limiting examples of polymers include poly(alkylene oxide), poly(acrylamide), poly(acrylic acid), poly(acrylamide-co-acrylic acid), poly(acrylamide-co-diallyldimethylammonium chloride), poly(acrylonitrile), poly(allylamine), poly(amide), poly(anhydride), poly(butylene), poly(c-caprolactone), poly(carbonate), poly(ester), poly(etheretherketone), poly(ethersulphone), poly(ethylene), poly(ethylene alcohol), poly(ethylenimine), poly(ethylene glycol), poly(ethylene oxide), poly(glycolide) ((like poly(glycolic acid)), poly(hydroxy butyrate), poly(hydroxyethylmethacrylate), poly(hydroxypropylmethacrylate), poly(hydroxystyrene), poly(imide), poly(lactide), poly(L-lactic acid), poly(D,L-lactic acid), poly(lactide-co-glycolide), poly(lysine), poly(methacrylate), poly(methacrylic acid), poly(methylmethacrylate), poly(orthoester), poly(phenylene oxide), poly(phosphazene), poly(phosphoester), poly(propylene fumarate), poly(propylene), poly(propylene glycol), poly(propylene oxide), poly(styrene), poly(sulfone), poly(tetrafluoroethylene), poly(vinyl acetate), poly(vinyl alcohol), poly(vinyl chloride), poly(vinylidene fluoride), poly(vinyl pyrrolidone), poly(urethane), collagen, gelatin, any copolymer thereof (like poly(ethylene oxide) poly(propylene oxide) copolymers (poloxamers), poly(vinyl alcohol-co-ethylene), poly(styrene-co-allyl alcohol), and poly(ethylene)-block-poly(ethylene glycol), and/or any mixtures thereof.

A shell material has a thickness sufficient to allow formation of a porogen scaffold. As such, a shell material can be of any thickness, with the proviso that the amount of shell material is sufficient to create a porogen scaffold useful for its intended purpose. The thickness of the shell material is measured from the interior surface of the shell that is adjacent of the core material to the exterior surface of the shell.

Thus, in an embodiment, a porogen composition comprises a shell material. In an aspect of this embodiment, a porogen composition comprises a shell material having a melting point temperature that is lower than a melting point temperature of the core material. In aspects of this embodiment, a porogen composition comprises a shell material having a melting point temperature that is lower than a melting point temperature of the core material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a shell material having a melting point temperature that is lower than a melting point temperature of the core material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a shell material having a melting point temperature that is lower than a melting point temperature of the core material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In an aspect of this embodiment, a porogen composition comprises a shell material having a glass transition temperature that is lower than a glass transition temperature of the core material. In aspects of this embodiment, a porogen composition comprises a shell material having a glass transition temperature that is lower than a glass transition temperature of the core material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a shell material having a glass transition temperature that is lower than a glass transition temperature of the core material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a shell material having a glass transition temperature that is lower than a glass transition temperature of the core material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In another embodiment, a porogen composition comprises a shell material having a thickness sufficient to allow formation of a porogen scaffold. In aspects of this embodiment, a porogen composition comprises a shell material having a thickness of, e.g., about 1 μm, about 2 μm, about 3 μm, about 4 μm, about 5 μm, about 6 μm, about 7 μm, about 8 μm, about 9 μm, about 10 μm, about 15 μm, about 20 μm, about 25 μm, about 30 μm, about 35 μm, about 40 μm, about 45 μm, or about 50 μm. In other aspects of this embodiment, a porogen composition comprises a shell material having a thickness of, e.g., at least 1 μm, at least 2 μm, at least 3 μm, at least 4 μm, at least 5 μm, at least 6 μm, at least 7 μm, at least 8 μm, at least 9 μm, at least 10 μm, at least 15 μm, at least 20 μm, at least 25 μm, at least 30 μm, at least 35 μm, at least 40 μm, at least 45 μm, or at least 50 μm. In yet other aspects of this embodiment, a porogen composition comprises a shell material having a thickness of, e.g., about 5 μm to about 50 μm, about 5 μm to about 75 μm, about 5 μm to about 100 μm, about 5 μm to about 200 μm, about 5 μm to about 300 μm, about 10 μm to about 50 μm, about 10 μm to about 75 μm, about 10 μm to about 100 μm, about 10 μm to about 200 μm, about 10 μm to about 300 μm, about 15 μm to about 50 μm, about 15 μm to about 75 μm, about 15 μm to about 100 μm, about 15 μm to about 200 μm, or about 15 μm to about 300 μm.

In another embodiment, a shell material comprises an inorganic material. In another embodiment, a shell material comprises an organic material. In another embodiment, a shell material comprises a salt and/or its derivatives, a ceramic and/or its derivatives, a sugar and/or its derivatives, a polysaccharide and/or its derivatives, a wax and/or its derivatives, a metal and/or its derivatives, a surfactant and/or its derivatives, a water soluble solid and/or its derivatives, or a polymer and/or its derivatives.

The present specification discloses, in part, a porogen comprising a core material. A core material of a porogen can be made of any material with the proviso that 1) the melting point temperature ($T_m$) of the core material is higher than the melting point temperature of the shell material; and/or 2) the glass transition temperature ($T_g$) of the core material is higher than the glass transition temperature of the shell material. A core material can be of any shape, with the proviso that the shape is useful to create a porogen scaffold. Useful core shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

A core material has a thickness sufficient to allow formation of a porogen scaffold. As such, a core material can be of any thickness, with the proviso that the amount of core material is sufficient to create a porogen scaffold useful for its intended purpose. The thickness of a core material can be measured base on its shape. For example, for triangular cores, quadrilateral cores, and any other type of polygonal shape, thickness is measured based on the base width of the core material. For example, for sided-shaped cores, like polyhedrons, triangles, pyramids, quadrilateral, or polygons, thickness is measured based on the base width of the core.

A core material can comprise a natural or synthetic, inorganic or organic material. Exemplary materials suitable as a core material disclosed herein, include, without limitation, natural and synthetic salts and its derivatives, natural and synthetic ceramics and/or its derivatives, natural and synthetic sugars and its derivatives, natural and synthetic polysaccharides and its derivatives, natural and synthetic waxes and its derivatives, natural and synthetic metals and its derivatives, natural and synthetic organic solids and its derivatives, natural and synthetic water soluble solids and its derivatives, and/or natural and synthetic polymers and its derivatives, composites thereof, and/or combinations thereof. Exemplary materials suitable as a core material are described above in the present specification.

Thus, in an embodiment, a porogen composition comprises a core material. In an aspect of this embodiment, a porogen composition comprises a core material having a melting point temperature that is higher than a melting point temperature of the shell material. In aspects of this embodiment, a porogen composition comprises a core material having a melting point temperature that is higher than a melting point temperature of the shell material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a core material having a melting point temperature that is higher than a melting point temperature of the shell material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a core material having a melting point temperature that is higher than a melting point temperature of the shell material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In an aspect of this embodiment, a porogen composition comprises a core material having a glass transition temperature that is higher than a glass transition temperature of the shell material. In aspects of this embodiment, a porogen composition comprises a core material having a glass transition temperature that is higher than a glass transition temperature of the shell material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a core material having a glass transition temperature that is higher than a glass transition temperature of the shell material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a core material having a glass transition temperature that is higher than a glass transition temperature of the shell material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In another embodiment, a porogen composition comprises a core material having a thickness sufficient to allow formation of a porogen scaffold. In aspects of this embodiment, a porogen composition comprises a core material having a thickness of, e.g., about 10 μm, about 20 μm, about 30 μm, about 40 μm, about 50 μm, about 60 μm, about 70 μm, about 80 μm, about 90 μm, about 100 μm, about 200 μm, about 300 μm, about 400 μm, about 500 μm, about 600 μm, about 700 μm, about 800 μm, or about 900 μm. In other aspects of this embodiment, a porogen composition comprises a shell material having a thickness of, e.g., at least 10 μm, at least 20 μm, at least 30 μm, at least 40 μm, at least 50 μm, at least 60 μm, at least 70 μm, at least 80 μm, at least 90 μm, at least 100 μm, at least 200 μm, at least 300 μm, at least 400 μm, at least 500 μm, at least 600 μm, at least 700 μm, at least 800 μm, or at least 900 μm. In yet other aspects of this embodiment, a porogen composition comprises a shell material having a thickness of, e.g., about 10 μm to about 500 μm, about 10 μm to about 750 μm, about 10 μm to about 1000 μm, about 10 μm to about 2000 μm, about 10 μm to about 3000 μm, about 25 μm to about 500 μm, about 25 μm to about 750 μm, about 25 μm to about 1000 μm, about 25 μm to about 2000 μm, about 25 μm to about 3000 μm, about 50 μm to about 500 μm, about 50 μm to about 750 μm, about 50 μm to about 1000 μm, about 50 μm to about 2000 μm, about 50 μm to about 3000 μm, about 100 μm to about 500 μm, about 100 μm to about 750 μm, about 100 μm to about 1000 μm, about 100 μm to about 2000 μm, or about 100 μm to about 3000 μm.

In another embodiment, a core material comprises an inorganic material. In another embodiment, a core material comprises an organic material. In another embodiment, a core material comprises a salt and/or its derivatives, a ceramic and/or its derivatives, a sugar and/or its derivatives, a polysaccharide and/or its derivatives, a wax and/or its derivatives, a metal and/or its derivatives, a water soluble solid and/or its derivatives, or a polymer and/or its derivatives.

The present specification discloses, in part, a porogen comprising a shell material and a core material, where the core material has a higher melting point temperature or glass transition temperature relative to the melting point temperature or the glass transition temperature of the shell material. The melting point temperature or glass transition temperature of any of the shell and core materials is well known to a person of ordinary skill and is publicly available information. See, e.g., Polymer Physics, pp. 454 (Ed. Michael Rubinstein, Edmund T. Rolls, Ralph H. Colby, Oxford University Press, 2003); Inorganic Chemistry, pp. 822 (Ed. Peter Atkins, Duward F. Shriver, Tina Overton, Jonathan Rourke, W.H. Freeman, 2006); and Carbohydrate Chemistry, pp. 96 (B. G. Davis and A. J. Fairbanks, Oxford University Press 2002), each of which is incorporated by reference in its entirety.

Thus, in an embodiment, a porogen comprises a shell material comprising an inorganic material and a core material comprising an inorganic material, where the core material has a higher melting point temperature or glass transition temperature relative to the melting point temperature or the glass transition temperature of the shell material. In another embodiment, a porogen comprises a shell material comprising an organic material and a core material comprising an inorganic material, where the core material has a higher melting point temperature or glass transition temperature relative to the melting point temperature or the glass transition temperature of the shell material. In another embodiment, a porogen comprises a shell material comprising an inorganic material and a core material comprising an organic material, where the core material has a higher melting point temperature or glass transition temperature relative to the melting point temperature or the glass transition temperature of the shell material. In another embodiment, a porogen comprises a shell material comprising an organic material and a core material comprising an organic material, where the core material has a higher melting point temperature or glass transition temperature relative to the melting point temperature or the glass transition temperature of the shell material.

In another embodiment, a porogen comprises a shell material comprising a salt and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a salt and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a ceramic and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a sugar and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a polysaccharide and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a wax and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a metal and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a water-soluble solid and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a polymer and/or its derivatives, where the core material has a higher melting point temperature or glass transition temperature relative to the melting point temperature or the glass transition temperature of the shell material.

Aspects of the present specification disclose, in part, a porogen comprising a core material and shell material where the shell material is fusible and the core material is non-fusible under a given physical or physicochemical treatment. As used herein, the term "under a given physical or physicochemical treatment" refers to a physical or physicochemical treatment that permits the shell material to transition from its solid phase to its liquid phase, but maintains the core material in its solid phase.

Thus, in an embodiment, a porogen comprises a shell material comprising an inorganic material and a core material comprising an inorganic material, where under a given physical or physicochemical treatment the shell material is fusible and the core material is non-fusible. In another embodiment, a porogen comprises a shell material comprising an organic material and a core material comprising an inorganic material, where under a given physical or physicochemical treatment the shell material is fusible and the core material is non-fusible. In another embodiment, a porogen comprises a shell material comprising an inorganic material and a core material comprising an organic material, where under a given physical or physicochemical treatment the shell material is fusible and the core material is non-fusible. In another embodiment, a porogen comprises a shell material comprising an organic material and a core material comprising an organic material, where under a given physical or physicochemical treatment the shell material is fusible and the core material is non-fusible.

In another embodiment, a porogen comprises a shell material comprising a salt and/or its derivatives and a core material comprising a salt and/or its derivatives, where under a given physical or physicochemical treatment the shell material is fusible and the core material is non-fusible. In another embodiment, a porogen comprises a shell material comprising a ceramic and/or its derivatives and a core material comprising a salt and/or its derivatives, where under a given physical or physicochemical treatment the shell material is fusible and the core material is non-fusible. In another embodiment, a porogen comprises a shell material comprising a sugar and/or its derivatives and a core material comprising a salt and/or its derivatives, where under a given physical or physicochemical treatment the shell material is fusible and the core material is non-fusible. In another embodiment, a porogen comprises a shell material comprising a polysaccharide and/or its derivatives and a core material comprising a salt and/or its derivatives, where under a given physical or physicochemical treatment the shell material is fusible and the core material is non-fusible. In another embodiment, a porogen comprises a shell material comprising a wax and/or its derivatives and a core material comprising a salt and/or its derivatives, where under a given physical or physicochemical treatment the shell material is fusible and the core material is non-fusible. In another embodiment, a porogen comprises a shell material comprising a metal and/or its derivatives and a core material comprising a salt and/or its derivatives, where under a given physical or physicochemical treatment the shell material is fusible and the core material is non-fusible. In another embodiment, a porogen comprises a shell material comprising a surfactant and/or its derivatives and a core material comprising a salt and/or its derivatives, where under a given physical or physicochemical treatment the shell material is fusible and the core material is non-fusible. In another embodiment, a porogen comprises a shell material comprising a water-soluble solid and/or its derivatives and a core material comprising a salt and/or its derivatives, where under a given physical or physicochemical treatment the shell material is fusible and the core material is non-fusible. In another embodiment, a porogen comprises a shell material comprising a polymer and/or its derivatives and a core material comprising a salt and/or its derivatives, where under a given physical or physicochemical treatment the shell material is fusible and the core material is non-fusible.

In another embodiment, a porogen comprises a shell material comprising a salt and/or its derivatives and a core material comprising a ceramic and/or its derivatives, where under a given physical or physicochemical treatment the shell material is fusible and the core material is non-fusible. In another embodiment, a porogen comprises a shell material comprising a ceramic and/or its derivatives and a core material comprising a ceramic and/or its derivatives, where under a given physical or physicochemical treatment the shell material is fusible and the core material is non-fusible. In another embodiment, a porogen comprises a shell material comprising a sugar and/or its derivatives and a core material comprising a ceramic and/or its derivatives, where under a given physical or physicochemical treatment the shell material is fusible and the core material is non-fusible. In another embodiment, a porogen comprises a shell material comprising a polysaccharide and/or its derivatives and a core material comprising a ceramic and/or its derivatives, where under a given physical or physicochemical treatment the shell material is fusible and the core material is non-fusible. In another embodiment, a porogen comprises a shell material comprising a wax and/or its derivatives and a core material comprising a ceramic and/or its derivatives, where under a given physical or physicochemical treatment the shell material is fusible and the core material is non-fusible. In another embodiment, a porogen comprises a shell material comprising a metal and/or its derivatives and a core material comprising a ceramic and/or its derivatives, where under a given physical or physicochemical treatment the shell material is fusible and the core material is non-fusible. In another embodiment, a porogen comprises a shell material comprising a surfactant and/or its derivatives and a core material comprising a ceramic and/or its derivatives, where under a given physical or physicochemical treatment the shell material is fusible and the core material is non-fusible. In another embodiment, a porogen comprises a shell material comprising a water-soluble solid and/or its derivatives and a core material comprising a ceramic and/or its derivatives, where under a given physical or physicochemical treatment the shell material is fusible and the core material is non-fusible. In another embodiment, a porogen comprises a shell material comprising a polymer and/or its derivatives and a core material comprising a ceramic and/or its derivatives, where under a given physical or physicochemical treatment the shell material is fusible and the core material is non-fusible.

In another embodiment, a porogen comprises a shell material comprising a salt and/or its derivatives and a core material comprising a sugar and/or its derivatives, where under a given physical or physicochemical treatment the shell material is fusible and the core material is non-fusible. In another embodiment, a porogen comprises a shell material comprising a ceramic and/or its derivatives and a core material comprising a sugar and/or its derivatives, where under a given physical or physicochemical treatment the shell material is fusible and the core material is non-fusible. In another embodiment, a porogen comprises a shell material comprising a sugar and/or its derivatives and a core material comprising a sugar and/or its derivatives, where under a given physical or physicochemical treatment the shell material is fusible and the core material is non-fusible. In another embodiment, a porogen comprises a shell material comprising a polysaccharide and/or its derivatives and a core material comprising a sugar and/or its derivatives, where under a given physical or physicochemical treatment the shell material is fusible and the core material is non-fusible. In another embodiment, a porogen comprises a shell material comprising a wax and/or its derivatives and a core material comprising a sugar and/or its derivatives, where under a given physical or physicochemical treatment the shell material is fusible and the core material is non-fusible. In another embodiment, a porogen comprises a shell material comprising a metal and/or its derivatives and a core material comprising a sugar and/or its derivatives, where under a given physical or physicochemical treatment the shell material is fusible and the core material is non-fusible. In another embodiment, a porogen comprises a shell material comprising a surfactant and/or its derivatives and a core material comprising a sugar and/or its derivatives, where under a given physical or physicochemical treatment the shell material is fusible and the core material is non-fusible. In another embodiment, a porogen comprises a shell material comprising a water-soluble solid and/or its derivatives and a core material comprising a sugar and/or its derivatives, where under a given physical or physicochemical treatment the shell material is fusible and the core material is non-fusible. In another embodiment, a porogen comprises a shell material comprising a polymer and/or its derivatives and a core material comprising a sugar and/or its derivatives, where under a given physical or physicochemical treatment the shell material is fusible and the core material is non-fusible.

In another embodiment, a porogen comprises a shell material comprising a salt and/or its derivatives and a core material comprising a polysaccharide and/or its derivatives, where under a given physical or physicochemical treatment the shell material is fusible and the core material is non-fusible. In another embodiment, a porogen comprises a shell material comprising a ceramic and/or its derivatives and a core material comprising a polysaccharide and/or its derivatives, where under a given physical or physicochemical treatment the shell material is fusible and the core material is non-fusible. In another embodiment, a porogen comprises a shell material comprising a sugar and/or its derivatives and a core material comprising a polysaccharide and/or its derivatives, where under a given physical or physicochemical treatment the shell material is fusible and the core material is non-fusible. In another embodiment, a porogen comprises a shell material comprising a polysaccharide and/or its derivatives and a core material comprising a polysaccharide and/or its derivatives, where under a given physical or physicochemical treatment the shell material is fusible and the core material is non-fusible. In another embodiment, a porogen comprises a shell material comprising a wax and/or its derivatives and a core material comprising a polysaccharide and/or its derivatives, where under a given physical or physicochemical treatment the shell material is fusible and the core material is non-fusible. In another embodiment, a porogen comprises a shell material comprising a metal and/or its derivatives and a core material comprising a polysaccharide and/or its derivatives, where under a given physical or physicochemical treatment the shell material is fusible and the core material is non-fusible. In another embodiment, a porogen comprises a shell material comprising a surfactant and/or its derivatives and a core material comprising a polysaccharide and/or its derivatives, where under a given physical or physicochemical treatment the shell material is fusible and the core material is non-fusible. In another embodiment, a porogen comprises a shell material comprising a water-soluble solid and/or its derivatives and a core material comprising a polysaccharide and/or its derivatives, where under a given physical or physicochemical treatment the shell material is fusible and the core material is non-fusible. In another embodiment, a porogen comprises a shell material comprising a polymer and/or its derivatives and a core material comprising a polysaccharide and/or its derivatives, where under a given physical or physicochemical treatment the shell material is fusible and the core material is non-fusible.

In another embodiment, a porogen comprises a shell material comprising a salt and/or its derivatives and a core material comprising a wax and/or its derivatives, where under a given physical or physicochemical treatment the shell material is fusible and the core material is non-fusible. In another embodiment, a porogen comprises a shell material comprising a ceramic and/or its derivatives and a core material comprising a wax and/or its derivatives, where under a given physical or physicochemical treatment the shell material is fusible and the core material is non-fusible. In another embodiment, a porogen comprises a shell material comprising a sugar and/or its derivatives and a core material comprising a wax and/or its derivatives, where under a given physical or physicochemical treatment the shell material is fusible and the core material is non-fusible. In another embodiment, a porogen comprises a shell material comprising a polysaccharide and/or its derivatives and a core material comprising a wax and/or its derivatives, where under a given physical or physicochemical treatment the shell material is fusible and the core material is non-fusible. In another embodiment, a porogen comprises a shell material comprising a wax and/or its derivatives and a core material comprising a wax and/or its derivatives, where under a given physical or physicochemical treatment the shell material is fusible and the core material is non-fusible. In another embodiment, a porogen comprises a shell material comprising a metal and/or its derivatives and a core material comprising a wax and/or its derivatives, where under a given physical or physicochemical treatment the shell material is fusible and the core material is non-fusible. In another embodiment, a porogen comprises a shell material comprising a surfactant and/or its derivatives and a core material comprising a wax and/or its derivatives, where under a given physical or physicochemical treatment the shell material is fusible and the core material is non-fusible. In another embodiment, a porogen comprises a shell material comprising a water-soluble solid and/or its derivatives and a core material comprising a wax and/or its derivatives, where under a given physical or physicochemical treatment the shell material is fusible and the core material is non-fusible. In another embodiment, a porogen comprises a shell material comprising a polymer and/or its derivatives and a core material comprising a wax and/or its derivatives, where under a given physical or physicochemical treatment the shell material is fusible and the core material is non-fusible.

In another embodiment, a porogen comprises a shell material comprising a salt and/or its derivatives and a core material comprising a metal and/or its derivatives, where under a given physical or physicochemical treatment the shell material is fusible and the core material is non-fusible. In another embodiment, a porogen comprises a shell material comprising a ceramic and/or its derivatives and a core material comprising a metal and/or its derivatives, where under a given physical or physicochemical treatment the shell material is fusible and the core material is non-fusible. In another embodiment, a porogen comprises a shell material comprising a sugar and/or its derivatives and a core material comprising a metal and/or its derivatives, where under a given physical or physicochemical treatment the shell material is fusible and the core material is non-fusible. In another embodiment, a porogen comprises a shell material comprising a polysaccharide and/or its derivatives and a core material comprising a metal and/or its derivatives, where under a given physical or physicochemical treatment the shell material is fusible and the core material is non-fusible. In another embodiment, a porogen comprises a shell material comprising a wax and/or its derivatives and a core material comprising a metal and/or its derivatives, where under a given physical or physicochemical treatment the shell material is fusible and the core material is non-fusible. In another embodiment, a porogen comprises a shell material comprising a metal and/or its derivatives and a core material comprising a metal and/or its derivatives, where under a given physical or physicochemical treatment the shell material is fusible and the core material is non-fusible. In another embodiment, a porogen comprises a shell material comprising a surfactant and/or its derivatives and a core material comprising a metal and/or its derivatives, where under a given physical or physicochemical treatment the shell material is fusible and the core material is non-fusible. In another embodiment, a porogen comprises a shell material comprising a water-soluble solid and/or its derivatives and a core material comprising a metal and/or its derivatives, where under a given physical or physicochemical treatment the shell material is fusible and the core material is non-fusible. In another embodiment, a porogen comprises a shell material comprising a polymer and/or its derivatives and a core material comprising a metal and/or its derivatives, where under a given physical or physicochemical treatment the shell material is fusible and the core material is non-fusible.

In another embodiment, a porogen comprises a shell material comprising a salt and/or its derivatives and a core material comprising a water-soluble solid and/or its derivatives, where under a given physical or physicochemical treatment the shell material is fusible and the core material is non-fusible. In another embodiment, a porogen comprises a shell material comprising a ceramic and/or its derivatives and a core material comprising a water-soluble solid and/or its derivatives, where under a given physical or physicochemical treatment the shell material is fusible and the core material is non-fusible. In another embodiment, a porogen comprises a shell material comprising a sugar and/or its derivatives and a core material comprising a water-soluble solid and/or its derivatives, where under a given physical or physicochemical treatment the shell material is fusible and the core material is non-fusible. In another embodiment, a porogen comprises a shell material comprising a polysaccharide and/or its derivatives and a core material comprising a water-soluble solid and/or its derivatives, where under a given physical or physicochemical treatment the shell material is fusible and the core material is non-fusible. In another embodiment, a porogen comprises a shell material comprising a wax and/or its derivatives and a core material comprising a water-soluble solid and/or its derivatives, where under a given physical or physicochemical treatment the shell material is fusible and the core material is non-fusible. In another embodiment, a porogen comprises a shell material comprising a metal and/or its derivatives and a core material comprising a water-soluble solid and/or its derivatives, where under a given physical or physicochemical treatment the shell material is fusible and the core material is non-fusible. In another embodiment, a porogen comprises a shell material comprising a surfactant and/or its derivatives and a core material comprising a water-soluble solid and/or its derivatives, where under a given physical or physicochemical treatment the shell material is fusible and the core material is non-fusible. In another embodiment, a porogen comprises a shell material comprising a water-soluble solid and/or its derivatives and a core material comprising a water-soluble solid and/or its derivatives, where under a given physical or physicochemical treatment the shell material is fusible and the core material is non-fusible. In another embodiment, a porogen comprises a shell material comprising a polymer and/or its derivatives and a core material comprising a water-soluble solid and/or its derivatives, where under a given physical or physicochemical treatment the shell material is fusible and the core material is non-fusible.

In another embodiment, a porogen comprises a shell material comprising a salt and/or its derivatives and a core material comprising a polymer and/or its derivatives, where under a given physical or physicochemical treatment the shell material is fusible and the core material is non-fusible. In another embodiment, a porogen comprises a shell material comprising a ceramic and/or its derivatives and a core material comprising a polymer and/or its derivatives, where under a given physical or physicochemical treatment the shell material is fusible and the core material is non-fusible. In another embodiment, a porogen comprises a shell material comprising a sugar and/or its derivatives and a core material comprising a polymer and/or its derivatives, where under a given physical or physicochemical treatment the shell material is fusible and the core material is non-fusible. In another embodiment, a porogen comprises a shell material comprising a polysaccharide and/or its derivatives and a core material comprising a polymer and/or its derivatives, where under a given physical or physicochemical treatment the shell material is fusible and the core material is non-fusible. In another embodiment, a porogen comprises a shell material comprising a wax and/or its derivatives and a core material comprising a polymer and/or its derivatives, where under a given physical or physicochemical treatment the shell material is fusible and the core material is non-fusible. In another embodiment, a porogen comprises a shell material comprising a metal and/or its derivatives and a core material comprising a polymer and/or its derivatives, where under a given physical or physicochemical treatment the shell material is fusible and the core material is non-fusible. In another embodiment, a porogen comprises a shell material comprising a surfactant and/or its derivatives and a core material comprising a polymer and/or its derivatives, where under a given physical or physicochemical treatment the shell material is fusible and the core material is non-fusible. In another embodiment, a porogen comprises a shell material comprising a water-soluble solid and/or its derivatives and a core material comprising a polymer and/or its derivatives, where under a given physical or physicochemical treatment the shell material is fusible and the core material is non-fusible. In another embodiment, a porogen comprises a shell material comprising a polymer and/or its derivatives and a core material comprising a polymer and/or its derivatives, where under a given physical or physicochemical treatment the shell material is fusible and the core material is non-fusible.

The present specification discloses methods of making a porogen composition.

In one aspect, methods of making a porogen composition comprise the steps of: a) forming a particle out of a core material; and b) coating the particle with a shell material.

The present specification discloses, in part, forming a particle out of a core material. Suitable core materials are as described above. Forming a particle out of a core material can be accomplished by any suitable means, including, without limitation, pelletization by fluidized bed granulation, rotor granulation, or extrusion-spheronization; grinding by roller mills and sieving; solvent evaporation; or emulsion. Suitable particles of a core material are also commercially available from, e.g., Fisher Scientific (Pittsburgh, Pa.), Boehringer Ingelheim Pharmaceuticals, Inc. (Ridgefield, Conn.); and Paulaur Corp., (Cranbury, N.J.).

The present specification discloses, in part, coating a particle with a shell material. Suitable shell materials are as described above. Coating a particle with a shell material can be accomplished by any suitable means, including, without limitation, mechanical application such as, e.g., dipping, spraying, filtration, knifing, curtaining, brushing, or vapor deposition; physical adsorption application; thermal application; fluidization application; adhering application; chemical bonding application; self-assembling application; molecular entrapment application, and/or any combination thereof. The shell material is applied to the particle of core material in such a manner as to coat the particle with the desired thickness of shell material. Removal of excess shell material can be accomplished by any suitable means, including, without limitation, gravity-based filtering or sieving, vacuum-based filtering or sieving, blowing, and/or any combination thereof.

The present specification discloses in part, methods of making a porous material using the porogen compositions disclosed herein. In general, the porous material make by the methods disclosed herein are suitable for a wide variety of uses in biomedical, industrial and household applications currently fulfilled by polyurethane foam. For example, the porous materials disclosed herein may be produced in a variety of shapes and firmnesses useful as cushion underlay for carpets; as upholstery padding for furniture and vehicle interior components like seats, headrests, armrests, roof liners, dashboards, and instrument panels; as material for pillows, mattress bedding, toppers, and cores; as sponges; as mid- and outsoles of footwear; as vehicle fascia and other exterior parts; as fabric coatings as synthetic fibers; as packaging material; as integral skin form for vehicle interiors; and as sound-deadening material. As another example, the porous materials disclosed herein may be produced as a rigid and light weight material useful in the manufacturing of insulating material such as, e.g., panel or spray insulation in buildings, water heaters, refrigerated transport, and commercial and residential refrigeration. As yet another example, the porous materials disclosed herein may be produced having a wide variety of pore sizes useful in the manufacture of cleaning material such as, e.g., wipes, swabs, and abrasives; and filtration materials for air and/or liquid filtration.

The disclosed porous materials are not only useful in all applications currently fulfilled by polyurethane-based materials, but also in many additional applications not suitable for polyurethane-based materials. The porous materials disclosed herein a structural geometry substantially similar to polyurethane-based materials but with improved acid stability/resistance, base stability/resistance, chemical stability/resistance, thermal stability/resistance, oxidation stability/resistance, UV light stability/resistance, biocompatibility, biodegradation resistance, increased gas permeability, and/or increased range of mechanical properties. As such, the disclosed porous materials are not only useful in all applications currently fulfilled by polyurethane-based materials, but also in many additional applications not suitable for polyurethane-based materials. For example, the porous materials disclosed herein can be used in a filter for separating or cleaning material present in a chemically aggressive environment, as a component of a medical device where biocompatibility and/or biostability are desired, as a material, or component thereof, exposed to chemical, oxidative, UV light, thermal and/or radiation environment that would destabilize and/or degrade a polyurethane-based material. Non-limiting examples of applications for the porous materials disclosed herein include cushion underlay for carpets; upholstery padding for furniture and vehicle interior components like seats, headrests, armrests, roof liners, dashboards, and instrument panels; material for pillows, mattress bedding, toppers, and cores; sponges; mid- and outsoles of footwear; vehicle fascia and other exterior parts; fabric coatings as synthetic fibers; packaging material; integral skin form for vehicle interiors; sound-deadening material; insulating material such as, e.g., panel or spray insulation in buildings, water heaters, refrigerated transport, and commercial and residential refrigeration; structural components; simulated wood; cleaning material such as, e.g., wipes, swabs, and abrasives; and filtration materials for air and/or liquid filtration; filters for separating or cleaning material present in a chemically aggressive environment; and light weight armor material.

The present specification discloses, in part, a porous material comprising a matrix defining an array of interconnected pores having a low thermal conductivity and/or high acoustic absorption. Such a porous material is useful in insulation materials such as, e.g., panel or spray insulation in buildings, water heaters, refrigerated transport, and commercial and residential refrigeration. Additionally, such a porous material may be insoluble or substantially insoluble in solvents, acids, and/or bases used during the application of the insulating material or exposed to once installed. An insulating material useful for thermal insulation will typically be made from a thermoplastic polymer, such as, e.g., polystyrene. The porous material may be made in sheet form typically from about 0.5 cm to about 10 cm in thickness with a porosity of about 70 to about 95% with at least partly open pores with interconnection diameter from approximately 1.0 µm to approximately 150 µm and a mean pore size of about 50 µm to about 800 µm.

The present specification discloses, in part, a porous material comprising a matrix defining an array of interconnected pores useful in the manufacturing of cleaning materials, such as, e.g., wipes, swabs, and abrasives. Such porous cleaning materials are typically designed for particular applications by optimizing the affinity of the polymer and porosity of the matrix for the material to be cleaned. For instance, acidic aqueous solutions may be cleaned with a porous material comprising a lightly crosslinked polymer having basic functionalities on the backbone or pendants, such as lightly crosslinked chitosan or poly(ethyleneamine), which would swell in the acidic medium. Likewise basic aqueous spills can be best cleaned by a porous material comprising a lightly crosslinked poly(acrylic acid). In addition, amphiphilic aqueous spills can be best cleaned by a porous material comprising a lightly crosslinked poly(ethyleneglycol), which readily absorbs both water and some organic solvents such as, e.g., dioxane and dichloromethane. Lastly, hydrophobic spills can be cleaned using polymers that readily swell in and absorb hydrophobic materials, yet are not dissolved by them.

The present specification discloses, in part, a porous material comprising a matrix defining an array of interconnected pores useful as filtration materials for air and/or liquid filtration. Such porous filtration materials have Porosities for filters may vary from about 80% to approximately 99.9% and average pore size can vary from about 1 µm to about 2000 µm. The porous material must be predominantly open celled and with interconnection diameters varying from about 1 µm to about 1800 µm. Such porous filtration materials are typically designed for particular applications by optimizing the affinity of the polymer and porosity of the matrix for the material to be filtration. For example, hydrophilic filtration materials, such as, e.g., filtration materials comprising a matrix composed of fluoropolymer thermosets or poly(vinyl)-based thermoplastics, are readily wetted with aqueous solutions. Hydrophobic filters materials, such as, e.g., filtration materials comprising a matrix composed of cellulose-based thermoplastics or poly(vinyl)-based thermoplastics, are readily wet in low surface-tension liquids, such as organic solvents and silicone oil and are best suited for gas filtration and venting applications. In venting applications, air can pass through these filters without allowing the passage of water. Other filtration applications include the filtering of low surface tension and high surface tension solutions, as well as separation of low surface tension from high surface tension mediums.

The present specification discloses, in part, a porous material comprising a matrix defining an array of interconnected pores useful as filtration materials in a chemically aggressive environment. Such porous filtration materials have porosities for filters may vary from about 80% to approximately 99.9% and average pore size can vary from about 300 µm to about 5000 µm. The porous material must be predominantly open celled and with interconnection diameters varying from about 300 µm to about 5,000 µm. Such porous filtration materials are typically designed for particular applications by optimizing the affinity of the polymer and porosity of the matrix for the material to be filtration. For example, such filtration materials comprising a matrix composed of fluoropolymer thermosets.

The present specification discloses, in part, a porous material comprising a matrix defining an array of interconnected pores having thermally stability. Such a porous material is useful in light weight armor materials like a component of a flak jacket, bullet-proof vest, or armor panels for a vehicle. A porous filtration material suitable as light weight armor material typically comprises low carbon content materials or other non-combustible materials, such as, e.g., silicone-based elastomers, fluorosilicone-based elastomers, and/or fluoropolymer thermosets. The addition of certain ceramic nanopowders can help retard the projectile or shrapnel with aid of high density high yield strength particulate.

The porogens disclosed herein can be used in any methods of making a porous material that utilized previously described porogens. The porous materials disclosed herein can be formed as a separate component or can be integrated into a base material. Examples of such methods are described in, e.g., Gates, et al., Materials Containing Voids with Void Size Controlled on the Nanometer Scale, U.S. Pat. No. 7,674,521; Hart, et al., Discrete Nano-Textured Structures in Biomolecular Arrays and Method of Use, U.S. Pat. No. 7,651,872; Xu and Grenz, Methods and Devices Using a Shrinkable Support for Porous Monolithic Materials, U.S. Pat. No. 7,651,762; van den Hoek, et al., VLSI Fabrication Processes for Introducing Pores into Dielectric Materials, U.S. Pat. No. 7,629,224; Murphy, et al., Tissue Engineering Scaffolds, U.S. Pat. No. 7,575,759; Swetlin, et al., Polyester Compositions, Methods of Manufacturing Said Compositions, and Articles Made Therefrom, U.S. Pat. No. 7,557,167; Goodner, et al., Formation of Interconnect Structures by Removing Sacrificial Material with Supercritical Carbon Dioxide, U.S. Pat. No. 7,466,025; Xu, Ultraporous Sol Gel Monoliths, U.S. Pat. No. 7,439,272; Todd, Apparatus, Precursors and Deposition Methods for Silicone-Containing Materials, U.S. Pat. No. 7,425,350; Flodin and Aurell, Method for Preparing an Open Porous Polymer Material and an Open Porous Polymer Material, U.S. Pat. No. 7,425,288; Watkins and Pai, Mesoporous Materials and Methods, U.S. Pat. No. 7,419,772; Connor, et al., Porous Composition of Matter, and Method of Making Same, U.S. Pat. No. 7,368,483; Lukas, et al., Porous Low Dielectric Constant Compositions and Methods for Making and Using Same, U.S. Pat. No. 7,332,445; Wu, et al., Methods for Producing Low Stress Porous Low-K Dielectric Materials Using Precursors with Organic Functional Groups, U.S. Pat. No. 7,241,704; Yuan and Ding, Functionalized Porous Poly (Aryl Ether Ketone) Materials and Their Use, U.S. Pat. No. 7,176,273; Gleason, et al., Porous Material Formation by Chemical Vapor Deposition onto Colloidal Crystal Templates, U.S. Pat. No. 7,112,615; Bruza, et al., Composition Containing a Cross-Linkable Matrix Precursor and a Poragen, and Porous Matrix Prepared Therefrom, U.S. Pat. No. 7,109,249; Huang, et al., Nitrogen-Containing Polymers as Porogens in the Preparation of Highly Porous, Low Dielectric Constant Materials, U.S. Pat. No. 7,087,982; Taboas, et al., Controlled Local/Global and Micro/Macro-Porous 3D Plastic, Polymer and Ceramic/Cement Composite Scaffold Fabrication and Applications Thereof, U.S. Pat. No. 7,087,200; Kloster, et al., Method of Forming a Selectively Converted Inter-Layer Dielectric Using A Porogen Material, U.S. Pat. No. 7,018,918; You, et al., Porous Materials, U.S. Pat. No. 6,998,148; Khanarian, et al., Porous Optical Materials, U.S. Pat. No. 6,967,222; Holmes and Cooper, Manufacturing Porous Cross-Linked Polymer Monoliths, U.S. Pat. No. 6,693,159; Ma, Reverse Fabrication of Porous Materials, U.S. Pat. No. 6,673,285; Kilaas, et al., Combined Liner and Matrix System, U.S. Pat. No. 6,672,385; Chaouk and Meijs, Hydratable Siloxane Comprising Porous Polymers, U.S. Pat. No. 6,663,668; Allen, et al., Porous Materials, U.S. Pat. No. 6,602,804; Hawker, et al., Porous Dielectric Material and Electronic Devices Fabricated Therewith, U.S. Pat. No. 6,541,865; Davankov, et al., Method of Making Biocompatible Polymeric Adsorbing Material for Purification of Physiological Fluids of Organism, U.S. Pat. No. 6,531,523; Shastri, et al., Three-Dimensional Polymer Matrices, U.S. Pat. No. 6,471,993; Yates, Photogenerated Nanoporous Materials, U.S. Pat. No. 6,380,270; Fonnum, Method for the Manufacture of Amino Group Containing Support Matrices, Support Matrices Prepared by the Method, and Use of the Support Matrices, U.S. Pat. No. 6,335,438; Chaouk, et al., Polymers, U.S. Pat. No. 6,225,367; Chaouk, et al., High Water Content Porous Polymer, U.S. Pat. No. 6,160,030; Hawker, et al., Dielectric Compositions and Method for Their Manufacture, U.S. Pat. No. 6,107,357; Li, et al., Polymeric Microbeads and Methods of Preparation, U.S. Pat. No. 6,100,306; Chaouk, et al., Process for Manufacture of A Porous Polymer by Use of A Porogen, U.S. Pat. No. 6,060,530; Li, et al., Polymeric Microbeads, U.S. Pat. No. 5,863,957; Frechet and Svec, Porous Polymeric Material with Gradients, U.S. Pat. No. 5,728,457; Frechet and Svec, Pore-Size Selective Modification of Porous Materials, U.S. Pat. No. 5,633,290; Yen, et al., Ion Exchange Polyethylene Membrane and Process, U.S. Pat. No. 5,531,899; Soria, et al., Membrane for a Filtration, Gas or Liquid Separation or Pervaporation Apparatus and A Manufacturing Method for Such Membrane, U.S. Pat. No. 5,066,398; Axisa, et al., Method of Fabricating A Porous Elastomer, U.S. Patent Publication 2010/0075056; Liljensten and Persoon, Biodegradable Ostochondreal Implant, U.S. Patent Publication 2009/0164014; Favis, et al., Porous Nanosheath Networks, Method of Making and Uses Thereof, U.S. Patent Publication 2009/0087641; Hosoya, et al., Porous Polymer and Process For Producing the Same, U.S. Patent Publication 2009/0045119; Andersson, Chitosan Compositions, U.S. Patent Publication 2009/0022770; Xie, Three-Dimensional Hydrophilic Porous Structures for Fuel Cell Plates, U.S. Patent Publication 2008/0292939; Ratner and Marshall, Novel Porous Materials, U.S. Patent Publication 2008/0075752; Ma and Chen, Porous Materials having Multi-Sized Geometries, U.S. Patent Publication 2007/0036844; Ma, Reverse Fabrication of Porous Materials, U.S. Patent Publication 2002/0005600; Liu, et al., Porous Materials, Methods of Making and Uses; and Liu, et al., Porous Materials, Methods of Making and Uses, each of which is incorporated by reference in its entirety.

In one aspect, the method of making a porous material comprises the steps of: a) coating porogens comprising a shell material and a core material with a matrix material base to form a matrix material-coated porogen mixture; b) treating the matrix material-coated porogen mixture to allow fusing of the porogens to form a porogen scaffold and stabilization of the matrix material; and c) removing the porogen scaffold, wherein porogen scaffold removal results in a porous material, the porous material comprising a matrix defining an array of interconnected pores.

In another aspect, a method of making a porous material comprises the steps of a) coating porogens comprising a shell material and a core material with a matrix material base to form a matrix material-coated porogen mixture; b) packing the matrix material-coated porogen mixture into a mold; c) treating the matrix material-coated porogen mixture to allow fusing of the porogens to form a porogen scaffold and stabilization of the matrix material; and d) removing the porogen scaffold, wherein porogen scaffold removal results in a porous material, the porous material comprising a matrix defining an array of interconnected pores.

As used herein, the term "matrix material base" is synonymous with "matrix base", "material base", "uncured matrix material", "uncured matrix" and "uncured material" and refers to a material disclosed herein, such as, e.g., a thermoset polymer, an elastomer, or a thermoplastic elastomer, that is in its uncured state; or a material disclosed herein, such as, e.g., a thermoplastic polymer, that is in its fluid or soft state.

The present specification discloses, in part, packing porogens into a mold prior to fusion. Porogens can be packed into the mold before coating of a matrix material base, or can be first coated with a matrix material base before packing into a mold. If coated first, the matrix material-coated porogen mixture may first have to be devolitalized before packing into a mold. Any mold shape may be used for packing the porogens. As a non-limiting example, a mold shape can be a shell that outlines the contours an implantable device, such as, e.g., a shell for a breast implant, or a shell for a muscle implant. As another non-limiting example, the mold shape can be one that forms sheets. Such sheets can be made in a wide variety or proportions based on the needed application. As yet another non-limiting example, a mold shape can be a three-dimensional form that represents the final shape of the porous material, such as, e.g., a filter, an insulating material, a light armor panel. The porogens may be packed into a mold using ultrasonic agitation, mechanical agitation, or any other suitable method for obtaining a closely packed array of porogens.

In an embodiment, a matrix material-coated porogen mixture is packed into a mold. In an aspect of this embodiment, a matrix material-coated porogen mixture is packed into a mold in a manner suitable obtaining a closely packed array of porogens. In other aspects of this embodiment, a matrix material-coated porogen mixture is packed into a mold using sonic agitation or mechanical agitation.

In another embodiment, porogens are packed into a mold. In an aspect of this embodiment, porogens are packed into a mold in a manner suitable obtaining a closely packed array of porogens. In other aspects of this embodiment, porogens are packed into a mold using sonic agitation or mechanical agitation.

As used herein, the term "porogen scaffold" refers to a three-dimensional structural framework composed of fused porogens that serves as the negative replica of a matrix defining an interconnected array or pores. The porogen compositions disclosed herein comprise a shell material and a core material.

The present specification discloses, in part, coating porogens with a matrix material base to form a matrix material-coated porogen mixture. Coating the porogens with a matrix material base can be accomplished by any suitable means, including, without limitation, mechanical application such as, e.g., dipping, spraying, knifing, curtaining, brushing, or vapor deposition, thermal application, adhering application, chemical bonding, self-assembling, molecular entrapment, and/or any combination thereof. The matrix material is applied to the porogens in such a manner as to coat the porogens with the desired thickness of matrix material. Removal of excess matrix material base can be accomplished by any suitable means, including, without limitation, gravity-based filtering or sieving, vacuum-based filtering or sieving, blowing, and/or any combination thereof.

Any matrix material base can be used to coat the porogens with the proviso that the matrix material base is a suitable material to form a porous material. A matrix material base can be any organic or inorganic material, composites thereof, and/or combinations thereof. Non-limiting examples of a matrix material include thermoset polymers, thermoplastic polymers, elastomers, thermoplastic elastomers, or combinations thereof. A matrix material may comprise homopolymers or copolymers that are degradable, substantially non-degradable, or non-degradable. A matrix material useful in making the porous material disclosed herein may comprise block copolymers, random copolymers, alternating copolymers, graft copolymers, and/or mixtures thereof of thermoset polymers, thermoplastic polymers, elastomers, thermoplastic elastomers having an isotactic, syndiotactic or atactic organization. Isotactic polymers have all substituents located on the same side of the polymer backbone; the polymer comprises 100% meso diads. Syndiotactic polymers or syntactic polymers comprise have substituents in alternate positions along the chain; the polymer comprises 100% of racemo diads. Atactic polymers have substituents placed randomly along the chain; the polymer comprises between 1 and 99% meso diads. Suitable matrix material bases include, without limitation, natural and synthetic ceramics and/or its derivatives, natural and synthetic polysaccharides and its derivatives, natural and synthetic metals and its derivatives, natural and synthetic polymers and its derivatives, and/or natural and synthetic elastomers and its derivatives, composites thereof, and/or combinations thereof; and include, e.g., carbon-based polymers, fluorocarbon-based polymers, and silicone-based polymers, including, without limitation, polyolefins, polyacrylates, fluoropolymers, polysiloxanes, polyesters, polyethers, polycarbonates, polyamides, polyanhydrides, polyorthoesters, polyurethanes, polyureas, polysaccharides, polyalkanes, polyalkenes, polyalkynes, nitriles, and fluorosilicones.

The present specification discloses, in part, a thermoset polymer. As used herein, the term "thermoset" or "thermoset polymer" refers to a material that irreversibly hardens (i.e., sets) into a given shape, generally through a curing process. A thermoset polymer may comprise homopolymers or copolymers that are degradable, substantially non-degradable, or non-degradable. A thermoset polymer useful in making the porous material disclosed herein may comprise block copolymers, random copolymers, alternating copolymers, graft copolymers, and/or mixtures thereof. Thermoset polymers outperform other materials (such as thermoplastics, see below) in a number of areas, including mechanical properties, chemical resistance, thermal stability, and overall durability. Thermoplastics include, without limitation, thermoset elastomers including carbon-based thermoset elastomers, fluorocarbon-based thermoset elastomers and silicone-based thermoset elastomers; formaldehyde-based thermoset polymers like phenol-formaldehyde, urea-formaldehyde, melamine formaldehyde; poly(ester)-based thermoset polymers; poly(epoxide)-based thermoset polymers; poly(imide)-based thermoset polymers; and poly(cyanurate)-based thermoset polymers.

The present specification discloses, in part, a thermoplastic polymer. As used herein, the term "thermoplastic", "thermoplastic polymer", or "thermosoftening plastic" refers to a material that softens and becomes fluid when heated and which hardens or freezes to a very glassy state when cooled sufficiently. Thermoplastics are elastic and flexible above a glass transition temperature Tg, the midpoint of a temperature range. Below a second, higher melting temperature, Tm, also the midpoint of a range, most thermoplastics have crystalline regions alternating with amorphous regions in which the chains approximate random coils. The amorphous regions contribute elasticity and the crystalline regions contribute strength and rigidity. Above Tm all crystalline structure disappears and the chains become randomly inter dispersed. As the temperature increases above Tm, viscosity gradually decreases without any distinct phase change. During processing, thermoplastic pellets are heated to a fluid state that allows the material to be injected under pressure from a heated cavity into a cool mold. As the material cools, the thermoplastic will harden in the shape of the mold. However, no cross-links are formed as with a thermoset polymer (i.e. no curing). Thermoplastic polymers differ from thermosetting polymers in that the changes seen are purely physical and, with the reapplication of heat, wholly reversible. As such, thermoplastics can be reprocessed many times through a cycle of remelting and remoulding. Most thermoplastics are high-molecular-weight polymers whose chains associate through weak Van der Weals forces; stronger dipole-dipole interactions and hydrogen bonding; or even stacking of aromatic rings. Thermoplastics include, e.g., amorphous thermoplastics, semi-crystalline thermoplastics, crystalline thermoplastics, and elastomeric and include, without limitation, poly(aryletherketone) (PAEK), poly(butylene terephthalate) (PBT), poly(butyrate), poly(ether ether ketone) (PEEK), poly(etherimide) (PEI), poly(2-hydroxyethyl methacrylate) (pHEMA), poly(isocyanurate) (PIR), poly(methyl methacrylate) (PMMA), poly (oxymethylene) (POM); poly(phenylsulfone) (PPSF), poly (styrene) (PS), poly(trimethylene terephthalate) (PTT), poly (urea) (PU); poly(amide)-based thermoplastics like aliphatic poly(amides), poly(phthalamides) (PPA), and aramides (aromatic poly(amides)); poly(carbonate)-based thermoplastics; poly(ester)-based thermoplastics like poly(ethylene) naphthalate (PEN), and poly(ethylene terephthalate) (PET); poly (olefin)-based thermoplastics like poly(ethylene) (PE), poly (propylene) (PP), poly(propylene carbonate) (PPC), poly (methylpentene) (PMP), and poly(butene-1) (PB-1); poly (stannane)-based thermoplastics; poly(sulfone)-based thermoplastics; poly(vinyl)-based thermoplastics like poly (vinyl chloride) (PVC), poly(vinylidene fluoride) (PVDF), poly(vinyl fluoride) (PVF), poly(vinyl nitrate) (PVN), and poly-(4-vinylphenol) (PVP); and cellulose-based thermoplastic like cellulose ester-based thermoplastics and cellulose ether-based thermoplastics.

The present specification discloses, in part, a fluoropolymer. As used herein, the term "fluoropolymer" refers to a fluorocarbon-based polymer with multiple strong carbon-fluorine bonds characterized by a high resistance to solvents, acids, and bases. Fluoropolymers include, without limitation, poly(vinyl fluoride) (PVF), poly(vinylidene fluoride) (PVDF), poly(tetrafluoroethylene) (PTFE), poly(chlorotrifluoroethylene) (PCTFE), perfluoroalkoxy (PFA), fluorinated ethylene-propylene (FEP), polyethylenetetrafluoroethylene (ETFE), poly(ethylenechlorotrifluoroethylene) (ECTFE), perfluoropolyether (PFPE) and fluoroelastomers.

The present specification discloses, in part, an elastomer. As used herein, the term "elastomer" or "elastic polymer" is synonymous with "thermoset elastomer" refers to an amorphous polymer that exists above its glass transition temperature ($T_g$) at ambient temperatures, thereby conferring the property of viscoelasticity so that considerable segmental motion is possible. Elastomers include, without limitation, carbon-based elastomers, silicone-based elastomers, thermoset elastomers, and thermoplastic elastomers. As used herein, the term "ambient temperature" refers to a temperature of about 18° C. to about 22° C. Elastomers, either naturally-occurring or synthetically-made, comprise monomers commonly made of carbon, hydrogen, oxygen, and/or silicone which are linked together to form long polymer chains. Elastomers are typically covalently cross-linked to one another, although non-covalently cross-linked elastomers are known. An elastomer may comprise homopolymers or copolymers that are degradable, substantially non-degradable, or non-degradable. An elastomer useful in making the porous material disclosed herein may comprise block copolymers, random copolymers, alternating copolymers, graft copolymers, and/or mixtures thereof. Unlike other polymers classes, an elastomer can be stretched many times its original length without breaking by reconfiguring themselves to distribute an applied stress, and the cross-linkages ensure that the elastomers will return to their original configuration when the stress is removed. Elastomers can be a non-medical grade elastomer or a medical grade elastomer. Medical grade elastomers are typically divided into three categories: non implantable, short term implantable and long-term implantable. Exemplary elastomers include, without limitation, bromo isobutylene isoprene (BIIR), polybutadiene (BR), chloro isobutylene isoprene (CIIR), polychloroprene (CR), chlorosulphonated polyethylene (CSM), diphenylsiloxane (DPS), ethylene propylene (EP), ethylene propylene diene monomer (EPDM), fluoronated hydrocarbon (FKM), fluoro silicone (FVQM), hydrogenated nitrile butadiene (HNBR), polyisoprene (IR), isobutylene isoprene butyl (IIR), methyl vinyl silicone (MVQ), nitrile, acrylonitrile butadiene (NBR), polyurethane (PU), styrene butadiene (SBR), styrene ethylene/butylene styrene (SEBS), polydimethylsiloxane (PDMS), polysiloxane (SI), acrylonitrile butadiene carboxy monomer (XNBR), and polyolefin elastomers like polyisobutylene (PIB), ethylene propylene rubber (EPR), ethylene propylene diene monomer (EPDM).

The present specification discloses, in part, an elastomer that is a fluorocarbon-based elastomer. As used herein, the term "fluorocarbon-based elastomer" refers to any fluorocarbon containing elastomer, such as, e.g., fluoro-elastomers (FKM), perfluoro-elastomers (FFKM) and tetrafluoro-ethylene/propylene elastomers (FEPM).

The present specification discloses, in part, an elastomer that is a silicone-based elastomer. As used herein, the term "silicone-based elastomer" refers to any silicone containing elastomer, such as, e.g., methyl vinyl silicone, polydimethylsiloxane, or polysiloxane. A silicone-based elastomer can be a high temperature vulcanization (HTV) silicone or a room temperature vulcanization (RTV). A silicone-based elastomer can be a non-medical grade silicone-based elastomer or a medical grade silicone-based elastomer. As used herein, the term "medical grade silicone-based elastomer" refers to a silicone-based elastomer approved by the U.S. Pharmacopeia (USP) as at least Class V. Medical grade silicone-based elastomers are typically divided into three categories: non implantable, short term implantable and long-term implantable.

The present specification discloses, in part, a thermoplastic elastomer. As used herein, the term "thermoplastic elastomer" or "thermoplastic rubber" refers to a material comprising a class of copolymers or a physical mix of polymers of a plastic and an elastomer that exhibit both thermoplastic and elastomeric properties. The principal difference between thermoset elastomers and thermoplastic elastomers is the type of crosslinking bond in their structures. In fact, crosslinking is a critical structural factor that contributes to impart high elastic properties. The crosslink in thermoset polymers is a covalent bond created during the vulcanization process. On the other hand, the crosslink in thermoplastic elastomer polymers is a weaker dipole or hydrogen bond or takes place in one of the phases of the material. A thermoplastic elastomer combines the elastomer-like properties of a thermoset elastomer and the processing characteristics of a thermoplastic. The TPE achieves this blend because it is composed of two regions (or phases): soft phases (cured thermoset rubber particles) dispersed within hard phases (the thermoplastic portion). Be aware that the physical, chemical, and thermal limits of both phases will determine the overall limits for the TPE. Because it is a blended material, a TPE is also considerably more expensive than a simpler thermoset material. Thermoplastic elastomers include, without limitation, styrenic block copolymers, elastomeric alloys, thermoplastic polyurethanes, thermoplastic polyester elastomers copolymers, polyolefin blends, thermoplastic polyester blends, and thermoplastic polyamides blends. Non-limiting examples, include, ethylene-vinyl acetate (EVA), copolymers of polypropylene and ethylene propylene diene monomer (EPDM) elastomer, copolymers of polystyrene and polybutadiene, and copolymers of polystyrene and polyisoprene.

Selection of a particular matrix material is within the knowledge level of a person of ordinary skill and will depend on the specific properties and characteristics desired of the porous material. For example, where the porous material is a component of an implantable medical device, the porous material will typically comprise a biocompatible, substantially non-degradable silicone-based elastomer. As another example, where the porous material is used as a component of an insulating application, the porous material will typically comprise a poly(styrene)-based low thermal conductivity thermoset polymer. As yet another example, where the porous material is a component of a filtration device for chemically aggressive or harsh applications, the porous material will typically comprise a fluoropolymer thermoset. As yet another example, where the porous material is a component of a light weight armor, the porous material will typically comprise a silicone-based elastomer, a fluorosilicone-based elastomer, or a fluoropolymer thermoset.

Thus, in an embodiment, porogens are coated with a matrix material base to a thickness sufficient to allow formation of a porous material comprising a matrix defining an interconnected array or pores. In aspects of this embodiment, porogens are coated with a matrix material to a thickness of, e.g., about 1 µm, about 2 µm, about 3 µm, about 4 µm, about 5 µm, about 6 µm, about 7 µm, about 8 µm, about 9 µm, about 10 µm, about 20 µm, about 30 µm, about 40 µm, about 50 µm, about 60 µm, about 70 µm, about 80 µm, about 90 µm, or about 100 µm. In other aspects of this embodiment, porogens are coated with a matrix material base to a thickness of, e.g., at least 1 µm, at least 2 µm, at least 3 µm, at least 4 µm, at least 5 µm, at least 6 µm, at least 7 µm, at least 8 µm, at least 9 µm, at least 10 µm, at least 20 µm, at least 30 µm, at least 40 µm, at least 50 µm, at least 60 µm, at least 70 µm, at least 80 µm, at least 90 µm, or at least 100 µm. In yet other aspects of this embodiment, porogens are coated with a matrix material base to a thickness of, e.g., at most 1 µm, at most 2 µm, at most 3 µm, at most 4 µm, at most 5 µm, at most 6 µm, at most 7 µm, at most 8 µm, at most 9 µm, at most 10 µm, at most 20 µm, at most 30 µm, at most 40 µm, at most 50 µm, at most 60 µm, at most 70 µm, at most 80 µm, at most 90 µm, or at most 100 µm. In still other aspects of this embodiment, porogens are coated with a matrix material base to a thickness of, e.g., about 1 µm to about 5 µm, about 1 µm to about 10 µm, about 5 µm to about 10 µm, about 5 µm to about 25 µm, about 5 µm to about 50 µm, about 10 µm to about 50 µm, about 10 µm to about 75 µm, about 10 µm to about 100 µm, about 25 µm to about 100 µm, or about 50 µm to about 100 µm.

The present specification discloses, in part, devolitalizing a matrix material-coated porogens. As used herein, the term "devolitalizing" or "devolitalization" refers to a process that removes volatile components from the matrix material-coated porogens. Matrix material-coated porogens may, or may not, be devolitalized. Devolitalization of the matrix material-coated porogens can be accomplished by any suitable means that substantially all the volatile components removed from the matrix material-coated porogens. Non-limiting examples of devolitalizing procedures include evaporation, freeze-drying, sublimation, extraction, and/or any combination thereof.

In an embodiment, a matrix material-coated porogens is devolitalized at a single temperature for a time sufficient to allow the evaporation of substantially all volatile components from the matrix material-coated porogens. In an aspect of this embodiment, a matrix material-coated porogens are devolitalized at ambient temperature for about 1 minute to about 5 minutes. In another aspect of this embodiment, a matrix material-coated porogens are devolitalized at ambient temperature for about 45 minutes to about 75 minutes. In yet another aspect of this embodiment, a matrix material-coated porogens are devolitalized at ambient temperature for about 90 minutes to about 150 minutes. In another aspect of this embodiment, a matrix material-coated porogens are devolitalized at about 18° C. to about 22° C. for about 1 minute to about 5 minutes. In yet another aspect of this embodiment, a matrix material-coated porogens are devolitalized at about 18° C. to about 22° C. for about 45 minutes to about 75 minutes. In still another aspect of this embodiment, a matrix material-coated porogens are devolitalized at about 18° C. to about 22° C. for about 90 minutes to about 150 minutes.

The present specification discloses, in part, treating a matrix material-coated porogen mixture to allow fusing of the porogens to form a porogen scaffold and stabilization of the matrix material. As used herein, the term "treating" refers to a process that 1) fuses the porogens to form a porogen scaffold useful to make a porous material comprising a matrix of interconnected array of pore and 2) stabilizes the matrix material. Non-limiting examples of treating include thermal treating like heating or freezing, chemical treating, catalyst treating, radiation treating, and physical treating. Treating of a matrix material-coated porogen scaffold can be done under any condition for any length of time with the proviso that the treating fuses the porogens to form a porogen scaffold useful to make a porous material comprising a matrix of interconnected array of pore and stabilizes the matrix material.

Thermal treating a matrix material-coated porogen mixture can be at any temperature or temperatures for any length of time or times with the proviso that the thermal treatment fuses the porogens to form a porogen scaffold and stabilizes the matrix material base to form a matrix as disclosed herein. A non-limiting example of temperatures useful in a thermal treatment are temperatures higher than the glass transition temperature or melting temperature of the porogens, such as between about 5° C. to about 50° C. higher than the glass transition temperature or melting temperature of the porogens. Any temperature can be used in a thermal treatment with the proviso that the temperature is sufficient to cause fusion of the porogens. As a non-limiting example, the thermal treatment can be from about 30° C. to about 250° C. Increasing the duration of the thermal treatment at a given temperature increases the connection size; increases the sintering temperature, and increases the growth rate of the connections. Any time can be used in a thermal treatment with the proviso that the time is sufficient to cause fusion of the porogens and cures the matrix material. Suitable times are generally from about 0.5 hours to about 48 hours.

Thus, in an embodiment, a matrix material-coated porogen scaffold is treated by thermal treatment, chemical treatment, catalyst treatment, radiation treatment, or physical treatment where the treatment is sufficient to stabilize a matrix material. In another embodiment, a matrix material-coated porogen scaffold is treated at a single time, where the treating time is sufficient to stabilize a matrix material.

In another embodiment, matrix material-coated porogens are thermal treated at a single temperature for a single time, where the treating temperature and time is sufficient to fuse the porogens to form a porogen scaffold and stabilize the matrix material.

In other aspects of this embodiment, the thermal treatment comprises heating a matrix material-coated porogens for a time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperature and time is sufficient to fuse the porogens to form a porogen scaffold and stabilize the matrix material. In yet other aspects of this embodiment, the thermal treatment comprises heating a matrix material-coated porogens for a time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperature and time is sufficient to fuse the porogens to form a porogen scaffold and stabilize the matrix material. In still other aspects of this embodiment, the thermal treatment comprises heating a matrix material-coated porogens for a time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperature and time is sufficient to fuse the porogens to form a porogen scaffold and stabilize the matrix material. In further aspects of this embodiment, the thermal treatment comprises heating a matrix material-coated porogens for a time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperature and time is sufficient to fuse the porogens to form a porogen scaffold and stabilize the matrix material.

In another aspect of this embodiment, a matrix material on a matrix material-coated porogen scaffold is treated at about 30° C. to about 130° C. for about 10 minutes to about 360 minutes, where the treating temperature and time is sufficient to fuse the porogens to form a porogen scaffold and stabilize the matrix material.

In yet another embodiment, a matrix material-coated porogens are thermal treated at a plurality of temperatures for a plurality of times, where the treating temperatures and times are sufficient to fuse the porogens to form a porogen scaffold and stabilize the matrix material. In an aspect of this embodiment, matrix material-coated porogens are treated at a first temperature for a first time, and then a second temperature for a second time, where the treating temperatures and times are sufficient to fuse the porogens to form a porogen scaffold and stabilize the matrix material, and where the first and second temperatures are different.

In aspects of this embodiment, thermal treatment comprises heating the matrix material-coated porogens at a first temperature for a first time, and then heating the porogens at a second temperature for a second time, where the treating temperatures and times are sufficient to fuse the porogens to form a porogen scaffold and stabilize the matrix material, and where the first and second temperatures are different. In other aspects of this embodiment, the thermal treatment comprises heating a matrix material-coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the matrix material-coated porogens, then heating for a second time the porogens at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and stabilize the matrix material, and where the first and second temperatures are different. In yet other aspects of this embodiment, the thermal treatment comprises heating a matrix material-coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating a matrix material-coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and stabilize the matrix material, and where the first and second temperatures are different. In still other aspects of this embodiment, the thermal treatment comprises heating a matrix material-coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating a matrix material-coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and stabilize the matrix material, and where the first and second temperatures are different.

In further aspects of this embodiment, the thermal treatment comprises heating a matrix material-coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating a matrix material-coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and stabilize the matrix material, and where the first and second temperatures are different.

In other aspects of this embodiment, thermal treatment comprises heating the matrix material-coated porogens at a first temperature for a first time, heating the porogens at a second temperature for a second time, and then heating the porogens at a third temperature at a third time, where the treating temperatures and times are sufficient to fuse the porogens to form a porogen scaffold and stabilize the matrix material, and where the first temperature is different from the second temperature and the second temperature is different from the third temperature.

In other aspects of this embodiment, the thermal treatment comprises heating a matrix material-coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating a matrix material-coated porogens for a second time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating a matrix material-coated porogens for a third time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and stabilize the matrix material, and where the first temperature is different from the second temperature and the second temperature is different from the third temperature. In yet other aspects of this embodiment, the thermal treatment comprises heating a matrix material-coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating a matrix material-coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating a matrix material-coated porogens for a third time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and stabilize the matrix material, and where the first temperature is different from the second temperature and the second temperature is different from the third temperature. In still other aspects of this embodiment, the thermal treatment comprises heating a matrix material-coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating a matrix material-coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating a matrix material-coated porogens for a third time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and stabilize the matrix material, and where the first temperature is different from the second temperature and the second temperature is different from the third temperature.

In further aspects of this embodiment, the thermal treatment comprises heating a matrix material-coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating a matrix material-coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C.

higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating a matrix material-coated porogens for a third time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and stabilize the matrix material, and where the first temperature is different from the second temperature and the second temperature is different from the third temperature.

In still other aspect of this embodiment, matrix material-coated porogens are treated at about 60° C. to about 75° C. for about 15 minutes to about 45 minutes, and then at about 120° C. to about 130° C. for about 60 minutes to about 90 minutes, where the treating temperatures and times is sufficient to fuse the porogens to form a porogen scaffold and stabilize the matrix material. In a further aspect of this embodiment, matrix material-coated porogen mixture is treated at about 60° C. to about 75° C. for about 15 minutes to about 45 minutes, then at about 135° C. to about 150° C. for about 90 minutes to about 150 minutes, and then at about 150° C. to about 165° C. for about 15 minutes to about 45 minutes.

The present specification discloses, in part, to form a porogen scaffold. As used herein, the term "porogen scaffold" refers to a three-dimensional structural framework composed of fused porogens that serves as the negative replica of the matrix defining an interconnected array of pores as disclosed herein.

The porogen scaffold is formed in such a manner that substantially all the fused porogens in the porogen scaffold have a similar diameter. As used herein, the term "substantially", when used to describe fused porogen, refers to at least 90% of the porogen comprising the porogen scaffold are fused, such as, e.g., at least 95% of the porogens are fused or at least 97% of the porogen are fused. As used herein, the term "similar diameter", when used to describe fused porogen, refers to a difference in the diameters of the two fused porogen that is less than about 20% of the larger diameter. As used herein, the term "diameter", when used to describe fused porogen, refers to the longest line segment that can be drawn that connects two points within the fused porogen, regardless of whether the line passes outside the boundary of the fused porogen. Any fused porogen diameter is useful with the proviso that the fused porogen diameter is sufficient to allow formation of a porogen scaffold useful in making a matrix as disclosed herein.

The porogen scaffold is formed in such a manner that the diameter of the connections between each fused porogen is sufficient to allow formation of a porogen scaffold useful in making a matrix as disclosed herein. As used herein, the term "diameter", when describing the connection between fused porogens, refers to the diameter of the cross-section of the connection between two fused porogens in the plane normal to the line connecting the centroids of the two fused porogens, where the plane is chosen so that the area of the cross-section of the connection is at its minimum value. As used herein, the term "diameter of a cross-section of a connection" refers to the average length of a straight line segment that passes through the center, or centroid (in the case of a connection having a cross-section that lacks a center), of the cross-section of a connection and terminates at the periphery of the cross-section. As used herein, the term "substantially", when used to describe the connections between fused porogens refers to at least 90% of the fused porogens comprising the porogen scaffold make connections between each other, such as, e.g., at least 95% of the fused porogens make connections between each other or at least 97% of the fused porogens make connections between each other.

In an embodiment, a porogen scaffold comprises fused porogens where substantially all the fused porogens have a similar diameter. In aspects of this embodiment, at least 90% of all the fused porogens have a similar diameter, at least 95% of all the fused porogens have a similar diameter, or at least 97% of all the fused porogens have a similar diameter. In another aspect of this embodiment, difference in the diameters of two fused porogens is, e.g., less than about 20% of the larger diameter, less than about 15% of the larger diameter, less than about 10% of the larger diameter, or less than about 5% of the larger diameter.

In another embodiment, a porogen scaffold comprises fused porogens have a mean diameter sufficient to enable the desired function of the porous material. In aspects of this embodiment, a porogen scaffold comprises fused porogens comprising mean fused porogen diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen scaffold comprises fused porogens comprising mean fused porogen diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen scaffold comprises fused porogens comprising mean fused porogen diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a matrix comprises fused porogens comprising mean fused porogen diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen scaffold comprises fused porogens comprising mean fused porogen diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a matrix comprises fused porogens comprising mean fused porogen diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen scaffold comprises fused porogens comprising mean fused porogen diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porogen scaffold comprises fused porogens connected to a plurality of other porogens. In aspects of this embodiment, a porogen scaffold comprises a mean fused porogen connectivity, e.g., about two other fused porogens, about three other fused porogens, about four other fused porogens, about five other fused porogens, about six other fused porogens, about seven other fused porogens, about eight other fused porogens, about nine other fused porogens, about ten other fused porogens, about 11 other fused porogens, or about 12 other fused porogens. In other aspects of this embodiment, a porogen scaffold comprises a mean fused porogen connectivity, e.g., at least two other fused porogens, at least three other fused porogens, at least four other fused porogens, at least five other fused porogens, at least six other fused porogens, at least seven other fused porogens, at least eight other fused porogens, at least nine other fused porogens, at least ten other fused porogens, at least 11 other fused porogens, or at least 12 other fused porogens. In yet other aspects of this embodiment, a porogen scaffold comprises a mean fused porogen connectivity, e.g., at most two other fused porogens, at most three other fused porogens, at most four other fused porogens, at most five other fused porogens, at most six other fused porogens, at most seven other fused porogens, at most eight other fused porogens, at most nine other fused porogens, at most ten other fused porogens, at most 11 other fused porogens, or at most 12 other fused porogens.

In still other aspects of this embodiment, a porogen scaffold comprises fused porogens connected to, e.g., about two other fused porogens to about 12 other fused porogens, about two other fused porogens to about 11 other fused porogens, about two other fused porogens to about ten other fused porogens, about two other fused porogens to about nine other fused porogens, about two other fused porogens to about eight other fused porogens, about two other fused porogens to about seven other fused porogens, about two other fused porogens to about six other fused porogens, about two other fused porogens to about five other fused porogens, about three other fused porogens to about 12 other fused porogens, about three other fused porogens to about 11 other fused porogens, about three other fused porogens to about ten other fused porogens, about three other fused porogens to about nine other fused porogens, about three other fused porogens to about eight other fused porogens, about three other fused porogens to about seven other fused porogens, about three other fused porogens to about six other fused porogens, about three other fused porogens to about five other fused porogens, about four other fused porogens to about 12 other fused porogens, about four other fused porogens to about 11 other fused porogens, about four other fused porogens to about ten other fused porogens, about four other fused porogens to about nine other fused porogens, about four other fused porogens to about eight other fused porogens, about four other fused porogens to about seven other fused porogens, about four other fused porogens to about six other fused porogens, about four other fused porogens to about five other fused porogens, about five other fused porogens to about 12 other fused porogens, about five other fused porogens to about 11 other fused porogens, about five other fused porogens to about ten other fused porogens, about five other fused porogens to about nine other fused porogens, about five other fused porogens to about eight other fused porogens, about five other fused porogens to about seven other fused porogens, or about five other fused porogens to about six other fused porogens.

In another embodiment, a porogen scaffold comprises fused porogens where the diameter of the connections between the fused porogens is sufficient to enable the desired function of the porous material. In aspects of this embodiment, the porogen scaffold comprises fused porogens where the diameter of the connections between the fused porogens is, e.g., about 10% the mean fused porogen diameter, about 20% the mean fused porogen diameter, about 30% the mean fused porogen diameter, about 40% the mean fused porogen diameter, about 50% the mean fused porogen diameter, about 60% the mean fused porogen diameter, about 70% the mean fused porogen diameter, about 80% the mean fused porogen diameter, or about 90% the mean fused porogen diameter. In other aspects of this embodiment, the porogen scaffold comprises fused porogens where the diameter of the connections between the fused porogens is, e.g., at least 10% the mean fused porogen diameter, at least 20% the mean fused porogen diameter, at least 30% the mean fused porogen diameter, at least 40% the mean fused porogen diameter, at least 50% the mean fused porogen diameter, at least 60% the mean fused porogen diameter, at least 70% the mean fused porogen diameter, at least 80% the mean fused porogen diameter, or at least 90% the mean fused porogen diameter. In yet other aspects of this embodiment, the porogen scaffold comprises fused porogens where the diameter of the connections between the fused porogens is, e.g., at most 10% the mean fused porogen diameter, at most 20% the mean fused porogen diameter, at most 30% the mean fused porogen diameter, at most 40% the mean fused porogen diameter, at most 50% the mean fused porogen diameter, at most 60% the mean fused porogen diameter, at most 70% the mean fused porogen diameter, at most 80% the mean fused porogen diameter, or at most 90% the mean fused porogen diameter.

In still other aspects of this embodiment, a porogen scaffold comprises fused porogens where the diameter of the connections between the fused porogens is, e.g., about 10% to about 90% the mean fused porogen diameter, about 15% to about 90% the mean fused porogen diameter, about 20% to about 90% the mean fused porogen diameter, about 25% to about 90% the mean fused porogen diameter, about 30% to about 90% the mean fused porogen diameter, about 35% to about 90% the mean fused porogen diameter, about 40% to about 90% the mean fused porogen diameter, about 10% to about 80% the mean fused porogen diameter, about 15% to about 80% the mean fused porogen diameter, about 20% to about 80% the mean fused porogen diameter, about 25% to about 80% the mean fused porogen diameter, about 30% to about 80% the mean fused porogen diameter, about 35% to about 80% the mean fused porogen diameter, about 40% to about 80% the mean fused porogen diameter, about 10% to about 70% the mean fused porogen diameter, about 15% to about 70% the mean fused porogen diameter, about 20% to about 70% the mean fused porogen diameter, about 25% to about 70% the mean fused porogen diameter, about 30% to about 70% the mean fused porogen diameter, about 35% to about 70% the mean fused porogen diameter, about 40% to about 70% the mean fused porogen diameter, about 10% to about 60% the mean fused porogen diameter, about 15% to about 60% the mean fused porogen diameter, about 20% to about 60% the mean fused porogen diameter, about 25% to about 60% the mean fused porogen diameter, about 30% to about 60% the mean fused porogen diameter, about 35% to about 60% the mean fused porogen diameter, about 40% to about 60% the mean fused porogen diameter, about 10% to about 50% the mean fused porogen diameter, about 15% to about 50% the mean fused porogen diameter, about 20% to about 50% the mean fused porogen diameter, about 25% to about 50% the mean fused porogen diameter, about 30% to about 50% the mean fused porogen diameter, about 10% to about 40% the mean fused porogen diameter, about 15% to about 40% the mean fused porogen diameter, about 20% to about 40% the mean fused porogen diameter, about 25% to about 40% the mean fused porogen diameter, or about 30% to about 40% the mean fused porogen diameter.

The present specification discloses, in part, stabilizing a matrix material. As used herein, the term "stabilizing" refers to a process that exposes the matrix material base to a element which activates a phase change in the matrix material base to a more stable state, such as, e.g., by physically or chemically cross-linked components of the matrix material to one another. Such a stabilization forms, e.g., a matrix. Non-limiting examples of stabilizing include curing, such as, e.g., thermal curing, chemical curing, catalyst curing, radiation curing, and physical curing of a thermoset, an elastomer, or a thermoplastic elastomer; or hardening of a thermoplastic. Stabilizing of a matrix material-coated porogen scaffold can be done under any condition for any length of time with the proviso that the conditions used stabilizes the matrix material.

The present specification discloses, in part, removing a porogen scaffold from a treated matrix material. Removal of the porogen scaffold can be accomplished by any suitable means, with the proviso that removal results in a porous material comprising a matrix defining an array of interconnected pores. Non-limiting examples of porogen removal include solvent extraction, thermal decomposition extraction, degradation extraction, mechanical extraction, and/or any combination thereof. As such, it is beneficial to use shell and core materials that are removable using an extraction method, but such method leaves the porous material intact. In extraction methods requiring exposure to another solution, such as, e.g., solvent extraction, the extraction can incorporate a plurality of solution changes over time to facilitate removal of the porogen scaffold. Non-limiting examples of solvents useful for solvent extraction include water, methylene chloride, acetic acid, formic acid, pyridine, tetrahydrofuran, dimethylsulfoxide, dioxane, benzene, and/or mixtures thereof. A mixed solvent can be in a ratio of higher than about 1:1, first solvent to second solvent or lower than about 1:1, first solvent to second solvent.

In an embodiment, a porogen scaffold is removed by extraction, where the extraction removes substantially all the porogen scaffold leaving a porous material comprising a matrix defining an array of interconnected pores. In aspects of this embodiment, a porogen scaffold is removed by extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold. In an aspect, a porogen scaffold is removed by a solvent extraction, a thermal extraction, a degradation extraction, a mechanical extraction, and/or any combination thereof.

In another embodiment, a porogen scaffold is removed by solvent extraction, where the extraction removes substantially all the porogen scaffold leaving a porous material comprising a matrix defining an array of interconnected pores. In aspects of this embodiment, a porogen scaffold is removed by solvent extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by solvent extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by solvent extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In yet another embodiment, a porogen scaffold is removed by thermal decomposition extraction, where the extraction removes substantially all the porogen scaffold leaving a porous material comprising a matrix defining an array of interconnected pores. In aspects of this embodiment, a porogen scaffold is removed by thermal decomposition extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by thermal decomposition extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by thermal decomposition extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by degradation extraction, where the extraction removes substantially all the porogen scaffold leaving a porous material comprising a matrix defining an array of interconnected pores. In aspects of this embodiment, a porogen scaffold is removed by degradation extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by degradation extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by degradation extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by mechanical extraction, where the extraction removes substantially all the porogen scaffold leaving a porous material comprising a matrix defining an array of interconnected pores. In aspects of this embodiment, a porogen scaffold is removed by mechanical extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by mechanical extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by mechanical extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

The present specification discloses, in part, a porous material comprising a matrix defining an array of interconnected pores. As used herein, the term "matrix defining an array of interconnected pores" or "matrix material defining an array of interconnected pores" is synonymous with "treated matrix" or "treated matrix material" and refers to a three-dimensional structural framework composed of a material, such as, e.g. a thermoset polymer, an elastomer, or a thermoplastic elastomer in its cured state or a material, such as, e.g., a thermoplastic polymer in its harden or solid state.

A porous material comprising a matrix defining an array of interconnected pores may exhibit high resistance to deformation. Resistance to deformation is the ability of a material to maintain its original form after being exposed to stress, and can be calculated as the original form of the material ($L_0$), divided by the form of the material after it is released from a stress ($L_R$), and then multiplied by 100.

In an embodiment, a porous material comprising a matrix defining an array of interconnected pores exhibits high resistance to deformation. In aspects of this embodiment, a porous material disclosed herein exhibits resistance to deformation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material disclosed herein exhibits resistance to deformation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material disclosed herein exhibits its resistance to deformation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material disclosed herein exhibits resistance to deformation of, e.g., about 85% to about 100%, about 87% to about 100%, about 90% to about 100%, about 93% to about 100%, about 95% to about 100%, or about 97% to about 100%.

A porous material comprising a matrix defining an array of interconnected pores may exhibit high elastic elongation. Elongation is a type of deformation caused when a material stretches under a tensile stress. Deformation is simply a change in shape that anything undergoes under stress. The elongation property of a material can be expressed as percent elongation, which is calculated as the length of a material after it is stretched (L), divided by the original length of the material ($L_0$), and then multiplied by 100. In addition, this elastic elongation may be reversible. Reversible elongation is the ability of a material to return to its original length after being release for a tensile stress, and can be calculated as the original length of the material ($L_0$), divided by the length of the material after it is released from a tensile stress ($L_R$), and then multiplied by 100.

In an embodiment, a porous material comprising a matrix defining an array of interconnected pores exhibits high elastic elongation. In aspects of this embodiment, a porous material disclosed herein exhibits an elastic elongation of, e.g., about 50%, about 80%, about 100%, about 200%, about 300%, about 400%, about 500%, about 600%, about 700%, about 800%, about 900%, about 1000%, about 1100%, about 1200%, about 1300%, about 1400%, about 1500%, about 1600%, about 1700%, about 1800%, about 1900%, or about 2000%. In other aspects of this embodiment, a porous material disclosed herein exhibits an elastic elongation of, e.g., at least 50%, at least 80%, at least 100%, at least 200%, at least 300%, at least 400%, at least 500%, at least 600%, at least 700%, at least 800%, at least 900%, at least 1000%, at least 1100%, at least 1200%, at least 1300%, at least 1400%, at least 1500%, at least 1600%, at least 1700%, at least 1800%, at least 1900%, or at least 2000%. In yet other aspects of this embodiment, a porous material disclosed herein exhibits an elastic elongation of, e.g., at most 50%, at most 80%, at most 100%, at most 200%, at most 300%, at most 400%, at most 500%, at most 600%, at most 700%, at most 800%, at most 900%, at most 1000%, at most 1100%, at most 1200%, at most 1300%, at most 1400%, at most 1500%, at most 1600%, at most 1700%, at most 1800%, at most 1900%, or at most 2000%. In still aspects of this embodiment, a porous material disclosed herein exhibits an elastic elongation of, e.g., about 50% to about 600%, about 50% to about 700%, about 50% to about 800%, about 50% to about 900%, about 50% to about 1000%, about 80% to about 600%, about 80% to about 700%, about 80% to about 800%, about 80% to about 900%, about 80% to about 1000%, about 100% to about 600%, about 100% to about 700%, about 100% to about 800%, about 100% to about 900%, about 100% to about 1000%, about 200% to about 600%, about 200% to about 700%, about 200% to about 800%, about 200% to about 900%, or about 200% to about 1000%.

In another embodiment, a porous material comprising a matrix defining an array of interconnected pores exhibits reversible elongation. In aspects of this embodiment, a porous material disclosed herein exhibits a reversible elastic elongation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material disclosed herein exhibits a reversible elastic elongation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material disclosed herein exhibits a reversible elastic elongation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material disclosed herein exhibits a reversible elastic elongation of, e.g., about 85% to about 100%, about 87% to about 100%, about 90% to about 100%, about 93% to about 100%, about 95% to about 100%, or about 97% to about 100%.

A porous material comprising a matrix defining an array of interconnected pores may exhibit low elastic modulus. Elastic modulus, or modulus of elasticity, refers to the ability of a material to resists deformation, or, conversely, an object's tendency to be non-permanently deformed when a force is applied to it. The elastic modulus of an object is defined as the slope of its stress-strain curve in the elastic deformation region: λ=stress/strain, where λ is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an objects response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a porous material comprising a matrix defining an array of interconnected pores exhibits low tensile modulus. In aspects of this embodiment, a porous material disclosed herein exhibits a tensile modulus of, e.g., about 0.01 MPa, about 0.02 MPa, about 0.03 MPa, about 0.04 MPa, about 0.05 MPa, about 0.06 MPa, about 0.07 MPa, about 0.08 MPa, about 0.09 MPa, about 0.1 MPa, about 0.15 MPa, about 0.2 MPa, about 0.25 MPa, about 0.3 MPa, about 0.35 MPa, about 0.4 MPa, about 0.45 MPa, about 0.5 MPa, about 0.55 MPa, about 0.6 MPa, about 0.65 MPa, or about 0.7 MPa. In other aspects of this embodiment, a porous material disclosed herein exhibits a tensile modulus of, e.g., at most 0.01 MPa, at most 0.02 MPa, at most 0.03 MPa, at most 0.04 MPa, at most 0.05 MPa, at most 0.06 MPa, at most 0.07 MPa, at most 0.08 MPa, at most 0.09 MPa, at most 0.1 MPa, at most 0.15 MPa, at most 0.2 MPa, at most 0.25 MPa, at most 0.3 MPa, at most 0.35 MPa, at most 0.4 MPa, at most 0.45 MPa, at most 0.5 MPa, at most 0.55 MPa, at most 0.6 MPa, at most 0.65 MPa, or at most 0.7 MPa. In yet other aspects of this embodiment, a porous material disclosed herein exhibits a tensile modulus of, e.g., about 0.01 MPa to about 0.1 MPa, about 0.01 MPa to about 0.2 MPa, about 0.01 MPa to about 0.3 MPa, about 0.01 MPa to about 0.4 MPa, about 0.01 MPa to about 0.5 MPa, about 0.01 MPa to about 0.6 MPa, or about 0.01 MPa to about 0.7 MPa.

In another embodiment, a porous material comprising a matrix defining an array of interconnected pores exhibits low shear modulus. In aspects of this embodiment, a porous material disclosed herein exhibits a shear modulus of, e.g., about 0.1 MPa, about 0.2 MPa, about 0.3 MPa, about 0.4 MPa, about 0.5 MPa, about 0.6 MPa, about 0.7 MPa, about 0.8 MPa, about 0.9 MPa, about 1 MPa, about 1.5 MPa, about 2 MPa, about 2.5 MPa, or about 3 MPa. In other aspects of this embodiment, a porous material disclosed herein exhibits a shear modulus of, e.g., at most 0.1 MPa, at most 0.2 MPa, at most 0.3 MPa, at most 0.4 MPa, at most 0.5 MPa, at most 0.6 MPa, at most 0.7 MPa, at most 0.8 MPa, at most 0.9 MPa, at most 1 MPa, at most 1.5 MPa, at most 2 MPa, at most 2.5 MPa, or at most 3 MPa. In yet other aspects of this embodiment, a porous material disclosed herein exhibits a shear modulus of, e.g., about 0.1 MPa to about 1 MPa, about 0.1 MPa to about 1.5 MPa, about 0.1 MPa to about 2 MPa, about 0.1 MPa to about 2.5 MPa, or about 0.1 MPa to about 3 MPa.

In another embodiment, a porous material comprising a matrix defining an array of interconnected pores exhibits low bulk modulus. In aspects of this embodiment, a porous material disclosed herein exhibits a bulk modulus of, e.g., about 0.5 GPa, about 0.6 GPa, about 0.7 GPa, about 0.8 GPa, about 0.9 GPa, about 1 GPa, about 1.5 GPa, about 2 GPa, about 2.5 GPa, about 3 GPa, about 3.5 GPa, about 4 GPa, about 4.5 GPa, or about 5 GPa. In other aspects of this embodiment, a porous material disclosed herein exhibits a bulk modulus of, e.g., at most 0.5 GPa, at most 0.6 GPa, at most 0.7 GPa, at most 0.8 GPa, at most 0.9 GPa, at most 1 GPa, at most 1.5 GPa, at most 2 GPa, at most 2.5 GPa, at most 3 GPa, at most 3.5 GPa, at most 4 GPa, at most 4.5 GPa, or at most 5 GPa. In yet other aspects of this embodiment, a porous material disclosed herein exhibits a bulk modulus of, e.g., about 0.5 GPa to about 5 GPa, about 0.5 GPa to about 1 GPa, or about 1 GPa to about 5 GPa.

A porous material comprising a matrix material defining an array of interconnected pores may exhibit high tensile strength relative to other polymer classes. Other polymer classes include any other polymer not classified as a matrix material. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a porous material comprising a matrix defining an array of interconnected pores exhibits high yield strength relative to other polymer classes. In aspects of this embodiment, a porous material disclosed herein exhibits a yield strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material disclosed herein exhibits a yield strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits a yield strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits a yield strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprising a matrix defining an array of interconnected pores exhibits high ultimate strength relative to other polymer classes. In aspects of this embodiment, a porous material disclosed herein exhibits an ultimate strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material disclosed herein exhibits an ultimate strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits an ultimate strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits an ultimate strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprising a matrix defining an array of interconnected pores exhibits high breaking strength relative to other polymer classes. In aspects of this embodiment, a porous material disclosed herein exhibits a breaking strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material disclosed herein exhibits a breaking strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits a breaking strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits a breaking strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

A porous material comprising a matrix defining an array of interconnected pores may exhibit low flexural strength relative to other polymer classes. Flexural strength, also known as bend strength or modulus of rupture, refers to an object's ability to resist deformation under load and represents the highest stress experienced within the object at its moment of rupture. It is measured in terms of stress.

In an embodiment, a porous material comprising a matrix defining an array of interconnected pores exhibits low flexural strength relative to other polymer classes. In aspects of this embodiment, a porous material disclosed herein exhibits a flexural strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, 1500 MPa, or about 2000 MPa. In other aspects of this embodiment, a porous material disclosed herein exhibits a flexural strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits a flexural strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits a flexural strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

A porous material comprising a matrix defining an array of interconnected pores may exhibit high compressibility. Compressibility refers to the relative volume change in response to a pressure (or mean stress) change, and is the reciprocal of the bulk modulus.

In an embodiment, a porous material comprising a matrix defining an array of interconnected pores exhibits high compressibility. In aspects of this embodiment, a porous material disclosed herein exhibits a compressibility of, e.g., about 0.1 kPa, about 0.5 kPa, about 1 kPa, about 5 kPa, about 10 kPa, about 15 kPa, about 20 kPa, about 30 kPa, about 40 kPa, about 50 kPa, about 60 kPa, about 70 kPa, about 80 kPa, about 90 kPa, or about 100 kPa. In other aspects of this embodiment, a porous material disclosed herein exhibits a compressibility of, e.g., at least 0.1 kPa, at least 0.5 kPa, at least 1 kPa, at least 5 kPa, at least 10 kPa, at least 15 kPa, at least 20 kPa, at least 30 kPa, at least 40 kPa, at least 50 kPa, at least 60 kPa, at least 70 kPa, at least 80 kPa, at least 90 kPa, or at least 100 kPa. In yet other aspects of this embodiment, a porous material disclosed herein exhibits a compressibility of, e.g., at most 0.1 kPa, at most 0.5 kPa, at most 1 kPa, at most 5 kPa, at most 10 kPa, at most 15 kPa, at most 20 kPa, at most 30 kPa, at most 40 kPa, at most 50 kPa, at most 60 kPa, at most 70 kPa, at most 80 kPa, at most 90 kPa, or at most 100 kPa. In still other aspects of this embodiment, a porous material disclosed herein exhibits a compressibility of, e.g., about 0.1 kPa to about 100 kPa, about 0.5 kPa to about 100 kPa, about 1 kPa to about 100 kPa, about 5 kPa to about 100 kPa, about 10 kPa to about 100 kPa, about 1 kPa to about 30 kPa, about 1 kPa to about 40 kPa, about 1 kPa to about 50 kPa, or about 1 kPa to about 60 kPa.

A porous material comprising a matrix defining an array of interconnected pores may exhibit low hardness. Hardness refers to various properties of an object in the solid phase that gives it high resistance to various kinds of shape change when force is applied. Hardness can be measured using a durometer and expressed using a Shore A scale, a unitless value that ranges from zero to 100.

In an embodiment, a porous material comprising a matrix defining an array of interconnected pores exhibits low hardness. In aspects of this embodiment, a porous material disclosed herein exhibits a Shore A hardness of, e.g., about 5, about 10, about 15, about 20, about 25, about 30, about 35, about 40, about 45, about 50, about 55, or about 60. In other aspects of this embodiment, a porous material disclosed herein exhibits a Shore A hardness of, e.g., at least 5, at least 10, at least 15, at least 20, at least 25, at least 30, at least 35, at least 40, at least 45, at least 50, at least 55, or at least 60. In yet other aspects of this embodiment, a porous material disclosed herein exhibits a Shore A hardness of, e.g., at most 5, at most 10, at most 15, at most 20, at most 25, at most 30, at most 35, at most 40, at most 45, at most 50, at most 55, or at most 60. In still other aspects of this embodiment, a porous material disclosed herein exhibits a Shore A hardness of, e.g., about 5 to about 60, about 10 to about 50, about 15 to about 45, about 20 to about 40, or about 25 to about 35.

A porous material comprising a matrix defining an array of interconnected pores may exhibit low thermal conductivity. Thermal conductivity, k, refers to the property of a material that indicates its ability to conduct heat and is measured in watts per Kelvin per meter ($W \cdot K^{-1} \cdot m^{-1}$). Multiplied by a temperature difference (in K) and an area (in $m^2$), and divided by a thickness (in m) the thermal conductivity predicts the energy loss (in W) through a piece of material. The reciprocal of thermal conductivity is thermal resistivity, and is measured in Kelvin-meters per watt ($K \cdot m \cdot W^{-1}$). Thermal conductance refers to the quantity of heat that passes in unit time through a plate of particular area and thickness when its opposite faces differ in temperature by one Kelvin. For a plate of thermal conductivity k, area A and thickness L this is kA/L, measured in $W \cdot K^{-1}$ (equivalent to: W/° C.). The reciprocal of thermal conductance is thermal resistance [L/(kA)], and is measured in $K \cdot W^{-1}$ (equivalent to: ° C./W). Heat transfer coefficient (k/L), also known as thermal admittance, refers to the quantity of heat that passes in unit time through unit area of a plate of particular thickness when its opposite faces differ in temperature by one Kelvin, and is measured in $W \cdot K^{-1} \, m^{-2}$. The reciprocal of heat transfer coefficient is thermal insulance (L/k), and is measured in $K \cdot m^2 W^{-1}$.

In an embodiment, a porous material comprising a matrix defining an array of interconnected pores exhibits low thermal conductivity. In aspects of this embodiment, a porous material disclosed herein exhibits a thermal conductivity of, e.g., about 0.010 $Wm^{-1}K^{-1}$, about 0.025 $Wm^{-1}K^{-1}$, about 0.050 $Wm^{-1}K^{-1}$, about 0.075 $Wm^{-1}K^{-1}$, about 0.10 $Wm^{-1}K^{-1}$, about 0.25 $Wm^{-1}K^{-1}$, about 0.50 $Wm^{-1}K^{-1}$, about 0.75 $Wm^{-1}K^{-1}$, about 1.0 $Wm^{-1}K^{-1}$, about 2.5 $Wm^{-1}K^{-1}$, about 5.0 $Wm^{-1}K^{-1}$, about 7.5 $Wm^{-1}K^{-1}$, or about 10 $Wm^{-1}K^{-1}$. In other aspects of this embodiment, a porous material disclosed herein exhibits a thermal conductivity of, e.g., at most 0.010 $Wm^{-1}K^{-1}$, at most 0.025 $Wm^{-1}K^{-1}$, at most 0.050 $Wm^{-1}K^{-1}$, at most 0.075 $Wm^{-1}K^{-1}$, at most 0.10 $Wm^{-1}K^{-1}$, at most 0.25 $Wm^{-1}K^{-1}$, at most 0.50 $Wm^{-1}K^{-1}$, at most 0.75 $Wm^{-1}K^{-1}$, at most 1.0 $Wm^{-1}K^{-1}$, at most 2.5 $Wm^{-1}K^{-1}$, at most 5.0 $Wm^{-1}K^{-1}$, at most 7.5 $Wm^{-1}K^{-1}$, or at most 10 $Wm^{-1}K^{-1}$. In yet other aspects of this embodiment, a porous material disclosed herein exhibits a thermal conductivity of, e.g., about 0.010 $Wm^{-1}K^{-1}$ to about 0.10 $Wm^{-1}K^{-1}$, about 0.010 $Wm^{-1}K^{-1}$ to about 1.0 $Wm^{-1}K^{-1}$, about 0.010 $Wm^{-1}K^{-1}$ to about 10 $Wm^{-1}K^{-1}$, about 0.050 $Wm^{-1}K^{-1}$ to about 0.50 $Wm^{-1}K^{-1}$, about 0.050 $Wm^{-1}K^{-1}$ to about 5.0 $Wm^{-1}K^{-1}$, about 0.010 $Wm^{-1}K^{-1}$ to about 0.050 $Wm^{-1}K^{-1}$, about 0.025 $Wm^{-1}K^{-1}$ to about 0.075 $Wm^{-1}K^{-1}$, about 0.050 $Wm^{-1}K^{-1}$ to about 0.10 $Wm^{-1}K^{-1}$, about 0.075 $Wm^{-1}K^{-1}$ to about 0.25 $Wm^{-1}K^{-1}$, about 0.10

Wm$^{-1}$K$^{-1}$ to about 0.50 Wm$^{-1}$K$^{-1}$, about 0.25 Wm$^{-1}$K$^{-1}$ to about 0.75 Wm$^{-1}$K$^{-1}$, about 0.50 Wm$^{-1}$K$^{-1}$ to about 1.0 Wm$^{-1}$K$^{-1}$, about 0.75 Wm$^{-1}$K$^{-1}$ to about 2.5 Wm$^{-1}$K$^{-1}$, about 1.0 Wm$^{-1}$K$^{-1}$ to about 5.0 Wm$^{-1}$K$^{-1}$, about 2.5 Wm$^{-1}$K$^{-1}$ to about 7.5 Wm$^{-1}$K$^{-1}$, or about 5.0 Wm$^{-1}$K$^{-1}$ to about 10 Wm$^{-1}$K$^{-1}$.

A porous material comprising a matrix includes pores having a shape sufficient to enable the desired function of the porous material. Useful pore shapes include, without limitation, roughly spherical, perfectly spherical, dodecahedrons (such as pentagonal dodecahedrons), and ellipsoids. For example, in certain biomedical applications, the shape of the pores should be in a form sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the shape of the pores should be in a form that facilitates removal unwanted substances from the filtered material.

A porous material comprising a matrix includes pores having a roundness sufficient to enable the desired function of the porous material. As used herein, "roundness" is defined as $(6 \times V)/(\pi \times D^3)$, where V is the volume and D is the diameter. Any pore roundness is useful with the proviso that the pore roundness is sufficient to enable the desired function of the porous material. For example, in certain biomedical applications, pore roundness should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, pore roundness should be sufficient to facilitate removal unwanted substances from the filtered material.

A porous material comprising a matrix may be formed in such a manner that substantially all the pores in the matrix have a similar diameter. As used herein, the term "substantially", when used to describe pores, refers to at least 90% of the pores within the matrix such as, e.g., at least 95% or at least 97% of the pores. As used herein, the term "similar diameter", when used to describe pores, refers to a difference in the diameters of the two pores that is less than about 20% of the larger diameter. As used herein, the term "diameter", when used to describe pores, refers to the longest line segment that can be drawn that connects two points within the pore, regardless of whether the line passes outside the boundary of the pore. For example, in certain biomedical applications, pore diameter should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, pore diameter should be sufficient to facilitate removal unwanted substances from the filtered material.

A porous material comprising a matrix is formed in such a manner that the diameter of the connections between pores is sufficient to enable the desired function of the porous material. As used herein, the term "diameter", when describing the connection between pores, refers to the diameter of the cross-section of the connection between two pores in the plane normal to the line connecting the centroids of the two pores, where the plane is chosen so that the area of the cross-section of the connection is at its minimum value. As used herein, the term "diameter of a cross-section of a connection" refers to the average length of a straight line segment that passes through the center, or centroid (in the case of a connection having a cross-section that lacks a center), of the cross-section of a connection and terminates at the periphery of the cross-section. As used herein, the term "substantially", when used to describe the connections between pores refers to at least 90% of the connections made between each pore comprising the matrix, such as, e.g., at least 95% or at least 97% of the connections. For example, in certain biomedical applications, the diameter of the connections between pores should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the diameter of the connections between pores should be sufficient to facilitate removal unwanted substances from the filtered material.

Thus, in an embodiment, a porous material comprising matrix defining an array of interconnected pores includes pores having a roundness sufficient to enable the desired function of the porous material. In aspects of this embodiment, a porous material disclosed herein includes pores having a roundness of, e.g., about 0.1, about 0.2, about 0.3, about 0.4, about 0.5, about 0.6, about 0.7, about 0.8, about 0.9, or about 1.0. In other aspects of this embodiment, a porous material disclosed herein includes pores having a roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, a porous material disclosed herein includes pores having a roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, a porous material disclosed herein includes pores having a roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

In another embodiment, substantially all pores within a porous material comprising a matrix have a similar diameter sufficient to enable the desired function of the porous material. In aspects of this embodiment, at least 90% of all pores within a porous material comprising a matrix have a similar diameter, at least 95% of all pores within a porous material comprising a matrix have a similar diameter, or at least 97% of all pores within a porous material comprising a matrix have a similar diameter. In another aspect of this embodiment, difference in the diameters of two pores is, e.g., less than about 20% of the larger diameter, less than about 15% of the larger diameter, less than about 10% of the larger diameter, or less than about 5% of the larger diameter.

In another embodiment, a porous material comprising a matrix defining an array of interconnected pores includes pores having a mean diameter sufficient to enable the desired function of the porous material. In aspects of this embodiment, a porous material comprising a matrix includes pores having mean pore diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porous material disclosed herein includes pores having mean pore diameter of, e.g., about 500 μm, about 600 μm, about 700 μm, about 800 μm, about 900 μm, about 1000 μm, about 1500 μm, about 2000 μm, about 2500 μm, or about 3000 μm. In yet other aspects of this embodiment, a porous material disclosed herein includes pores having mean pore diameter of, e.g., at least 50 μm, at least 75 μm, at least 100 μm, at least 150 μm, at least 200 μm, at least 250 μm, at least 300 μm, at least 350 μm, at least 400 μm, at least 450 μm, or at least 500 μm. In still other aspects, a porous material disclosed herein includes pores having mean pore diameter of, e.g., at least 500 μm, at least 600 μm, at least 700 μm, at least 800 μm, at least 900 μm, at least 1000 μm, at least 1500 μm, at least 2000 μm, at least 2500 μm, or at least 3000 μm. In further aspects of this embodiment, a porous material disclosed herein includes pores having mean pore diameter of, e.g., at most 50 μm, at most 75 μm, at most 100 μm, at most 150 μm, at most 200 μm, at most 250 μm, at most 300 μm, at most 350 μm, at most 400 μm, at most 450 μm, or at most 500 μm. In yet further aspects of this embodiment, a porous material disclosed herein includes pores having mean pore diameter of, e.g., at most 500 μm, at most 600 μm, at most 700 μm, at most 800 μm, at most 900 μm, at most 1000 μm, at most 1500 μm, at most 2000 μm, at most 2500 μm, or at most 3000 μm. In still further aspects of this embodiment, a porous material disclosed herein includes pores having mean pore diameter in a range from, e.g., about 300 μm to about 600 μm, about 200 μm to about 700 μm, about 100 μm to about 800 μm, about 500 μm to about 800 μm, about 50 μm to about 500 μm, about 75 μm to about 500 μm, about 100 μm to about 500 μm, about 200 μm to about 500 μm, about 300 μm to about 500 μm, about 50 μm to about 1000 μm, about 75 μm to about 1000 μm, about 100 μm to about 1000 μm, about 200 μm to about 1000 μm, about 300 μm to about 1000 μm, about 50 μm to about 1000 μm, about 75 μm to about 3000 μm, about 100 μm to about 3000 μm, about 200 μm to about 3000 μm, or about 300 μm to about 3000 μm.

In another embodiment, a porous material comprising a matrix defining an array of interconnected pores includes pores having a mean matrix strut thickness sufficient to enable the desired function of the porous material. In aspects of this embodiment, a porous material disclosed herein includes pores having a mean matrix strut thickness of, e.g., about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm. In other aspects of this embodiment, a porous material disclosed herein includes pores having a mean matrix strut thickness of, e.g., at least 10 μm, at least 20 μm, at least 30 μm, at least 40 μm, at least 50 μm, at least 60 μm, at least 70 μm, at least 80 μm, at least 90 μm, at least 100 μm, at least 110 μm, at least 120 μm, at least 130 μm, at least 140 μm, at least 150 μm, at least 160 μm, at least 170 μm, at least 180 μm, at least 190 μm, or at least 200 μm. In yet other aspects of this embodiment, a porous material disclosed herein includes pores having a mean matrix strut thickness of, e.g., at most 10 μm, at most 20 μm, at most 30 μm, at most 40 μm, at most 50 μm, at most 60 μm, at most 70 μm, at most 80 μm, at most 90 μm, at most 100 μm, at most 110 μm, at most 120 μm, at most 130 μm, at most 140 μm, at most 150 μm, at most 160 μm, at most 170 μm, at most 180 μm, at most 190 μm, or at most 200 μm. In still aspects of this embodiment, a porous material disclosed herein includes pores having a mean matrix strut thickness of, e.g., about 50 μm to about 110 μm, about 50 μm to about 120 μm, about 50 μm to about 130 μm, about 50 μm to about 140 μm, about 50 μm to about 150 μm, about 60 μm to about 110 μm, about 60 μm to about 120 μm, about 60 μm to about 130 μm, about 60 μm to about 140 μm, about 70 μm to about 110 μm, about 70 μm to about 120 μm, about 70 μm to about 130 μm, or about 70 μm to about 140 μm.

In another embodiment, a porous material comprising a matrix defining an array of interconnected pores includes pores connected to a plurality of other pores. In aspects of this embodiment, a porous material disclosed herein comprises a mean pore connectivity, e.g., about two other pores, about three other pores, about four other pores, about five other pores, about six other pores, about seven other pores, about eight other pores, about nine other pores, about ten other pores, about 11 other pores, or about 12 other pores. In other aspects of this embodiment, a porous material disclosed herein comprises a mean pore connectivity, e.g., at least two other pores, at least three other pores, at least four other pores, at least five other pores, at least six other pores, at least seven other pores, at least eight other pores, at least nine other pores, at least ten other pores, at least 11 other pores, or at least 12 other pores. In yet other aspects of this embodiment, a porous material disclosed herein comprises a mean pore connectivity, e.g., at most two other pores, at most three other pores, at most four other pores, at most five other pores, at most six other pores, at most seven other pores, at most eight other pores, at most nine other pores, at most ten other pores, at most 11 other pores, or at most 12 other pores.

In still other aspects of this embodiment, a porous material disclosed herein includes pores connected to, e.g., about two other pores to about 12 other pores, about two other pores to about 11 other pores, about two other pores to about ten other pores, about two other pores to about nine other pores, about two other pores to about eight other pores, about two other pores to about seven other pores, about two other pores to about six other pores, about two other pores to about five other pores, about three other pores to about 12 other pores, about three other pores to about 11 other pores, about three other pores to about ten other pores, about three other pores to about nine other pores, about three other pores to about eight other pores, about three other pores to about seven other pores, about three other pores to about six other pores, about three other pores to about five other pores, about four other pores to about 12 other pores, about four other pores to about 11 other pores, about four other pores to about ten other pores, about four other pores to about nine other pores, about four other pores to about eight other pores, about four other pores to about seven other pores, about four other pores to about six other pores, about four other pores to about five other pores, about five other pores to about 12 other pores, about five other pores to about 11 other pores, about five other pores to about ten other pores, about five other pores to about nine other pores, about five other pores to about eight other pores, about five other pores to about seven other pores, or about five other pores to about six other pores.

In another embodiment, a porous material comprising a matrix defining an array of interconnected pores includes pores where the diameter of the connections between pores is sufficient to enable the desired function of the porous material. In aspects of this embodiment, a porous material disclosed herein includes pores where the diameter of the connections between pores is, e.g., about 10% the mean pore diameter, about 20% the mean pore diameter, about 30% the mean pore diameter, about 40% the mean pore diameter, about 50% the mean pore diameter, about 60% the mean pore diameter, about 70% the mean pore diameter, about 80% the mean pore diameter, or about 90% the mean pore diameter. In other aspects of this embodiment, a porous material disclosed herein includes pores where the diameter of the connections between pores is, e.g., at least 10% the mean pore diameter, at least 20% the mean pore diameter, at least 30% the mean pore diameter, at least 40% the mean pore diameter, at least 50% the mean pore diameter, at least 60% the mean pore diameter, at least 70% the mean pore diameter, at least 80% the mean pore diameter, or at least 90% the mean pore diameter. In yet other aspects of this embodiment, a porous material disclosed herein includes pores where the diameter of the connections between pores is, e.g., at most 10% the mean pore diameter, at most 20% the mean pore diameter, at most 30% the mean pore diameter, at most 40% the mean pore diameter, at most 50% the mean pore diameter, at most 60% the mean pore diameter, at most 70% the mean pore diameter, at most 80% the mean pore diameter, or at most 90% the mean pore diameter.

In still other aspects of this embodiment, a porous material disclosed herein includes pores where the diameter of the connections between pores is, e.g., about 10% to about 90% the mean pore diameter, about 15% to about 90% the mean pore diameter, about 20% to about 90% the mean pore diameter, about 25% to about 90% the mean pore diameter, about 30% to about 90% the mean pore diameter, about 35% to about 90% the mean pore diameter, about 40% to about 90% the mean pore diameter, about 10% to about 80% the mean pore diameter, about 15% to about 80% the mean pore diameter, about 20% to about 80% the mean pore diameter, about 25% to about 80% the mean pore diameter, about 30% to about 80% the mean pore diameter, about 35% to about 80% the mean pore diameter, about 40% to about 80% the mean pore diameter, about 10% to about 70% the mean pore diameter, about 15% to about 70% the mean pore diameter, about 20% to about 70% the mean pore diameter, about 25% to about 70% the mean pore diameter, about 30% to about 70% the mean pore diameter, about 35% to about 70% the mean pore diameter, about 40% to about 70% the mean pore diameter, about 10% to about 60% the mean pore diameter, about 15% to about 60% the mean pore diameter, about 20% to about 60% the mean pore diameter, about 25% to about 60% the mean pore diameter, about 30% to about 60% the mean pore diameter, about 35% to about 60% the mean pore diameter, about 40% to about 60% the mean pore diameter, about 10% to about 50% the mean pore diameter, about 15% to about 50% the mean pore diameter, about 20% to about 50% the mean pore diameter, about 25% to about 50% the mean pore diameter, about 30% to about 50% the mean pore diameter, about 10% to about 40% the mean pore diameter, about 15% to about 40% the mean pore diameter, about 20% to about 40% the mean pore diameter, about 25% to about 40% the mean pore diameter, or about 30% to about 40% the mean pore diameter.

The present specification discloses, in part, a porous material comprising a matrix defining an array of interconnected pores having a porosity sufficient to enable the desired function of the porous material. As used herein, the term "porosity" refers to the amount of void space in a porous material comprising a matrix. As such, the total volume of a porous material comprising a matrix disclosed herein is based upon the matrix space and the void space. For example, in certain biomedical applications, the porosity of the porous material should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the porosity of the porous material should be sufficient to facilitate removal unwanted substances from the filtered material.

In aspects of this embodiment, a porous material comprising a matrix defining an array of interconnected pores has a porosity of, e.g., about 40% of the total volume of a matrix, about 50% of the total volume of a matrix, about 60% of the total volume of a matrix, about 70% of the total volume of a matrix, about 80% of the total volume of a matrix, about 90% of the total volume of a matrix, about 95% of the total volume of a matrix, or about 97% of the total volume of a matrix. In other aspects of this embodiment, a porous material disclosed herein has a porosity of, e.g., at least 40% of the total volume of a matrix, at least 50% of the total volume of a matrix, at least 60% of the total volume of a matrix, at least 70% of the total volume of a matrix, at least 80% of the total volume of a matrix, at least 90% of the total volume of a matrix, at least 95% of the total volume of a matrix, or at least 97% of the total volume of a matrix. In yet other aspects of this embodiment, a porous material disclosed herein has a porosity of, e.g., at most 40% of the total volume of a matrix, at most 50% of the total volume of a matrix, at most 60% of the total volume of a matrix, at most 70% of the total volume of a matrix, at most 80% of the total volume of a matrix, at most 90% of the total volume of a matrix, at most 95% of the total volume of a matrix, or at most 97% of the total volume of a matrix. In yet other aspects of this embodiment, a porous material disclosed herein has a porosity of, e.g., about 40% to about 97% of the total volume of a matrix, about 50% to about 97% of the total volume of a matrix, about 60% to about 97% of the total volume of a matrix, about 70% to about 97% of the total volume of a matrix, about 80% to about 97% of the total volume of a matrix, about 90% to about 97% of the total volume of a matrix, about 40% to about 95% of the total volume of a matrix, about 50% to about 95% of the total volume of a matrix, about 60% to about 95% of the total volume of a matrix, about 70% to about 95% of the total volume of a matrix, about 80% to about 95% of the total volume of a matrix, about 90% to about 95% of the total volume of a matrix, about 40% to about 90% of the total volume of a matrix, about 50% to about 90% of the total volume of a matrix, about 60% to about 90% of the total volume of a matrix, about 70% to about 90% of the total volume of a matrix, or about 80% to about 90% of the total volume of a matrix.

The present specification discloses, in part, a porous material comprising a matrix defining an array of interconnected pores having a mean open pore value and/or a mean closed pore value sufficient to enable the desired function of the porous material. As used herein, the term "mean open pore value" or "mean open pore" refers to the average number of pores that are connected to at least one other pore present in the matrix. As used herein, the term "mean closed pore value" or "mean closed pore" refers to the average number of pores that are not connected to any other pores present in the matrix. For example, in certain biomedical applications, the array of interconnected pores should have a mean open pore value and/or a mean closed pore value sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the array of interconnected pores should have a mean open pore value and/or a mean closed pore value sufficient to facilitate removal unwanted substances from the filtered material.

In aspects of this embodiment, a porous material comprising a matrix defining an array of interconnected pores has a mean open pore value of, e.g., about 70%, about 75%, about 80%, about 85%, about 90%, about 95%, or about 97%. In other aspects of this embodiment, a porous material disclosed herein has a mean open pore value of, e.g., at least 70%, at least 75%, at least 80%, at least 85%, at least 90%, at least 95%, or at least 97%. In yet other aspects of this embodiment, a porous material disclosed herein has a mean open pore value of, e.g., at most 70%, at most 75%, at most 80%, at most 85%, at most 90%, at most 95%, or at most 97%. In still aspects of this embodiment, a porous material disclosed herein has a mean open pore value of, e.g., about 70% to about 90%, about 75% to about 90%, about 80% to about 90%, about 85% to about 90%, about 70% to about 95%, about 75% to about 95%, about 80% to about 95%, about 85% to about 95%, about 90% to about 95%, about 70% to about 97%, about 75% to about 97%, about 80% to about 97%, about 85% to about 97%, or about 90% to about 97%.

In another embodiment, a porous material comprising a matrix defining an array of interconnected pores has a mean closed pore value sufficient to enable the desired function of the porous material. In aspects of this embodiment, a porous material disclosed herein has a mean closed pore value of, e.g., about 5%, about 10%, about 15%, or about 20%. In other aspects of this embodiment, a porous material disclosed herein has a mean closed pore value of, e.g., about 5% or less, about 10% or less, about 15% or less, or about 20% or less. In yet other aspects of this embodiment, a porous material disclosed herein has a mean closed pore value of, e.g., about 5% to about 10%, about 5% to about 15%, or about 5% to about 20%.

The present specification discloses, in part, a porous material comprising a matrix defining an array of interconnected pores having a void space sufficient to enable the desired function of the porous material. As used herein, the term "void space" refers to actual or physical space in a porous material comprising a matrix. As such, the total volume of a porous material comprising a matrix disclosed herein is based upon the matrix space and the void space. For example, in certain biomedical applications, the void space should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the void space should be sufficient to facilitate removal unwanted substances from the filtered material.

In aspects of this embodiment, a porous material comprising a matrix defining an array of interconnected pores has a void space of, e.g., about 50% of the total volume of a matrix, about 60% of the total volume of a matrix, about 70% of the total volume of a matrix, about 80% of the total volume of a matrix, about 90% of the total volume of a matrix, about 95% of the total volume of a matrix, or about 97% of the total volume of a matrix. In other aspects of this embodiment, a porous material disclosed herein has a void space of, e.g., at least 50% of the total volume of a matrix, at least 60% of the total volume of a matrix, at least 70% of the total volume of a matrix, at least 80% of the total volume of a matrix, at least 90% of the total volume of a matrix, at least 95% of the total volume of a matrix, or at least 97% of the total volume of a matrix. In yet other aspects of this embodiment, a porous material disclosed herein has a void space of, e.g., at most 50% of the total volume of a matrix, at most 60% of the total volume of a matrix, at most 70% of the total volume of a matrix, at most 80% of the total volume of a matrix, at most 90% of the total volume of a matrix, at most 95% of the total volume of a matrix, or at most 97% of the total volume of a matrix. In yet other aspects of this embodiment, a porous material disclosed herein has a void space of, e.g., about 50% to about 97% of the total volume of a matrix, about 60% to about 97% of the total volume of a matrix, about 70% to about 97% of the total volume of a matrix, about 80% to about 97% of the total volume of a matrix, about 90% to about 97% of the total volume of a matrix, about 50% to about 95% of the total volume of a matrix, about 60% to about 95% of the total volume of a matrix, about 70% to about 95% of the total volume of a matrix, about 80% to about 95% of the total volume of a matrix, about 90% to about 95% of the total volume of a matrix, about 50% to about 90% of the total volume of a matrix, about 60% to about 90% of the total volume of a matrix, about 70% to about 90% of the total volume of a matrix, or about 80% to about 90% of the total volume of a matrix.

A porous material comprising a matrix defining an array of interconnected pores generally has a low level of microporosity. As used herein, the term "microporosity" refers to a measure of the presence of small micropores within a porous material comprising a matrix itself (as opposed to the pores defined by a matrix). In some embodiments, all or substantially all of the micropores in a porous material disclosed herein are between about 0.1 µm and about 5 µm, such as between about 0.1 µm and about 3 µm or between about 0.1 µm and about 2 µm. The term "low level of microporosity" means that micropores represent less than 2% of the volume of a porous material disclosed herein, as measured by measuring the percentage void space in a cross-section through a matrix.

The shape, roundness, and diameter of pores, the connections between pores, the total volume of the porous material, the void volume, and the matrix volume can all be assessed using scanning electron microscopy. See, for example, FIGS. 2A-2H.

EXAMPLES

The following examples illustrate representative embodiments now contemplated, but should not be construed to limit the disclosed porous materials and methods of forming such porous materials.

Example 1

A Method of Making a Porous Material Sheet

This example illustrates how to make a sheet of porous material using the porogen compositions disclosed herein.

To coat porogens with a matrix material, an appropriate amount of porogens comprising a sugar core of about 335 µm and a polyethylene glycol shell of about 15 µm were mixed with an appropriate amount of about 35% (v/v) silicone in xylene (PN-3206-1; NuSil Technology LLC, Carpinteria, Calif.). In other experiments, the porogen composition used were porogens comprising a sugar core of about 335 µm and a polyethylene glycol shell of about 53 µm, porogens comprising a sugar core of about 390 µm and a polyethylene glycol shell of about 83 µm, or porogens comprising a sugar core of about 460 µm and a polyethylene glycol shell of about 104 µm. The mixture was filtered through a 43 µm sieve to remove the excess silicone and was poured into an about 20 cm×20 cm square mold coated with a non-stick surface.

To treat a matrix material-coated porogen mixture to allow fusing of the porogens to form a porogen scaffold and stabilization of the matrix material, the porogen/silicone mixture was placed into an oven and heated at a temperature of about 75° C. for about 60 min, and then about 126° C. for about 75 minutes. In another experiments, the porogen/silicone mixture was treated by placing into an oven and heated at a temperature of about 126° C. for about 75 minutes, or heated at a temperature of about 145° C. for about 150 minutes, or heated at a temperature of about 126° C. for about 85 min, and then about 30° C. for about 60 minutes. After curing, the sheet of cured elastomer coated porogen scaffold was removed.

To remove a porogen scaffold from the cured matrix material, the cured elastomer/porogen scaffold was immersed in hot water. After about 30 minutes, the hot water was removed and the resulting 20 cm×20 cm×1.5 mm sheet of porous material was air dried at an ambient temperature of about 18° C. to about 22° C. This process results in a porous material sheet as disclosed herein.

A sample from the sheet of porous material can be characterized by microCT analysis and/or scanning electron microscopy (SEM).

Example 2

A Method of Making a Device Comprising a Porous Material

This example illustrates how to make a device comprising a porous material formed using the porogen compositions disclosed herein.

Sheets of porous material comprising an elastomer matrix defining an interconnected array of pores is obtained as described in Example 1.

To attach a porous material to an article or device to form an article having elastomeric porous surface, a first porous material sheet is coated with a thin layer of silicone and then placed in the bottom cavity of a mold, adhesive side up. An article is then placed on top of the material surface coated with the adhesive. A second porous material sheet is then coated with a thin layer of silicone and applied to the uncovered surface of the article. The top piece of the mold cavity is then fixed in place pressing the two material sheets together creating a uniform interface. The silicone adhesive is allowed to cure by placing the covered device into an oven and heated at a temperature of about 126° C. for about 75 minutes. After curing, excess material is trimmed off creating a uniform seam around the article.

Example 3

A Method of Making a Textured Material Shell

This example illustrates how to make a textured breast implant shell using the porogen compositions disclosed herein.

To coat porogens with a matrix material, an appropriate amount of a porogen composition comprising a sugar core of about 335 µm and a polyethylene glycol shell of about 53 µm are mixed with an appropriate amount of about 35% (v/v) silicone in xylene (PN-3206-1; NuSil Technology LLC, Carpinteria, Calif.). In other experiments, the porogen composition used are porogens comprising a sugar core of about 335 µm and a polyethylene glycol shell of about 65 µm, porogens comprising a sugar core of about 320 µm and a polyethylene glycol shell of about 30 µm, or porogens comprising a sugar core of about 350 µm and a polyethylene glycol shell of about 50 µm. The mixture is filtered through a 43 µm sieve to remove the excess silicone.

To pour a matrix material-coated porogen mixture into a mold, the filtered elastomer coated porogen mixture is poured into a mold in the shape of a breast implant shell and the mold is mechanically agitated to pack firmly the mixture. The thickness of the shell is controlled based upon the design of the shell mold.

To treat a matrix material-coated porogen mixture to allow fusing of the porogens to form a porogen scaffold and cure the elastomer, the porogen/silicone mixture is placed into an oven and is heated at a temperature of about 75° C. for about 45 min, and then about 126° C. for about 75 minutes. In another experiments, the porogen/silicone mixture is treated by placing into an oven and heated at a temperature of about 126° C. for about 75 minutes, or heated at a temperature of about 145° C. for about 60 minutes. After treating, the shell mold is dismantled and the cured elastomer coated porogen scaffold is removed.

To remove a porogen scaffold from the cured matrix material, the cured elastomer/porogen scaffold is immersed in hot water. After about 3 hours, the hot water is removed and the resulting shell of porous material is dried in an oven of about 126° C. for 30 minutes. This process results in a textured breast implant shell.

Example 4

A Method of Making a Biocompatible Implantable Device Comprising a Porous Material This example illustrates how to make a biocompatible implantable device comprising a porous material formed using the porogen compositions disclosed herein.

A porous material shell comprising a matrix defining an interconnected array of pores is obtained as described in Example 3.

To attach the porous material shell to a biocompatible implantable device, the surface of the device is coated with a thin layer of silicone. The material shell is then placed over the adhesive coated device in a manner that ensures no wrinkles in the material form. The silicone adhesive is allowed to cure by placing the covered device into an oven and heating at a temperature of 126° C. for 75 minutes. After curing, excess material is trimmed off creating a uniform seam around the biocompatible implantable device. This process results in a biocompatible implantable device comprising a porous material as disclosed herein.

Example 5

A Method of Making a Biocompatible Implantable Article Having a Elastomeric Porous Surface This example illustrates how to make an implantable article comprising a porous material disclosed herein of about 0.5 mm to about 1.5 mm in thickness.

To preparing the surface of a device to receive a porous material, a base layer of 35% (w/w) silicone in xylene (PN-3206-1; NuSil Technology LLC, Carpinteria, Calif.) was coated on a mandrel (LR-10), placed into an oven, and cured at a temperature of about 126° C. for about 75 minutes.

To coat the base layer with a mixture comprising a matrix material and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 µm and a polyethylene glycol shell of about 53 µm until the maximum amount of porogens were absorbed into the uncured silicone. In other experiments, the porogen composition used were porogens comprising a sugar core of about 335 μm and a polyethylene glycol shell of about 60 μm, porogens comprising a sugar core of about 390 μm and a polyethylene glycol shell of about 83 μm, or porogens comprising a sugar core of about 460 μm and a polyethylene glycol shell of about 104 μm. The mandrel with the uncured silicon/porogen coating was air dried for about 60 minutes to allow the xylene to evaporate.

To treat a matrix material-coated porogen mixture to allow fusing of the porogens to form a porogen scaffold and stabilization of the matrix material, the mandrel coated with the uncured silicone/porogen mixture was placed into an oven and cured at a temperature of about 75° C. for 30 min, and then about 126° C. for 75 minutes. In another experiments, the porogen/silicone mixture was treated by placing into an oven and heated at a temperature of about 126° C. for about 75 minutes, or heated at a temperature of about 145° C. for about 60 minutes.

To remove porogen scaffold, the cured silicon/porogen scaffold was immersed in hot water. After about 3 hours, the hot water was removed and the resulting implant comprising a porous material of about 0.5 mm to about 1.5 mm was dried in an oven of about 126° C. for 30 minutes. This process resulted in a biocompatible implantable device comprising a porous material.

Figure 2A:
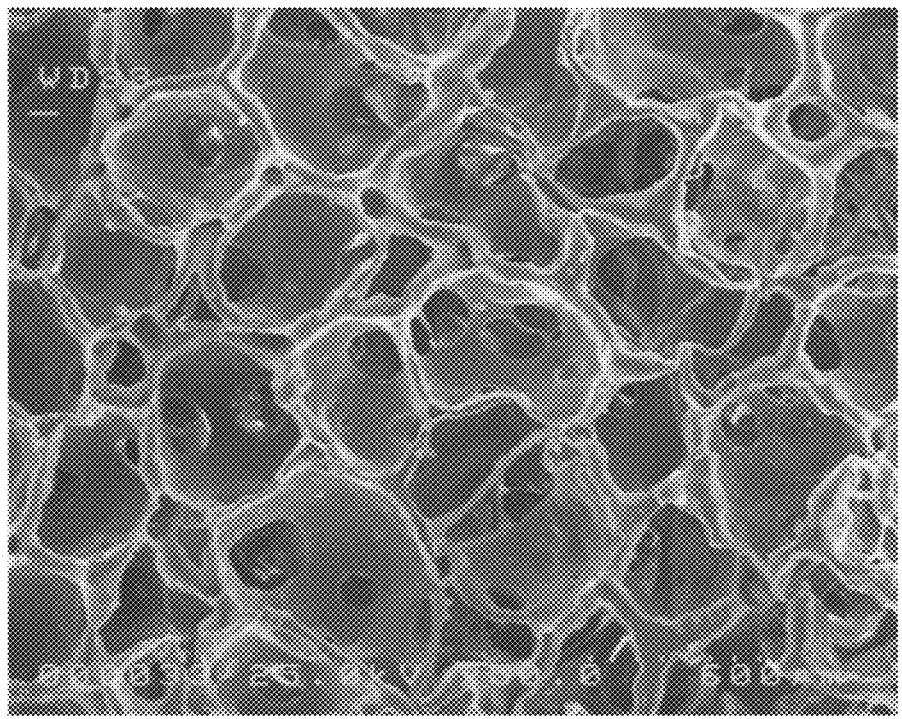
FIGS. 2A-2H show scanning electron micrograph images of porous materials made in accordance with the present specification.
Figure 2B:
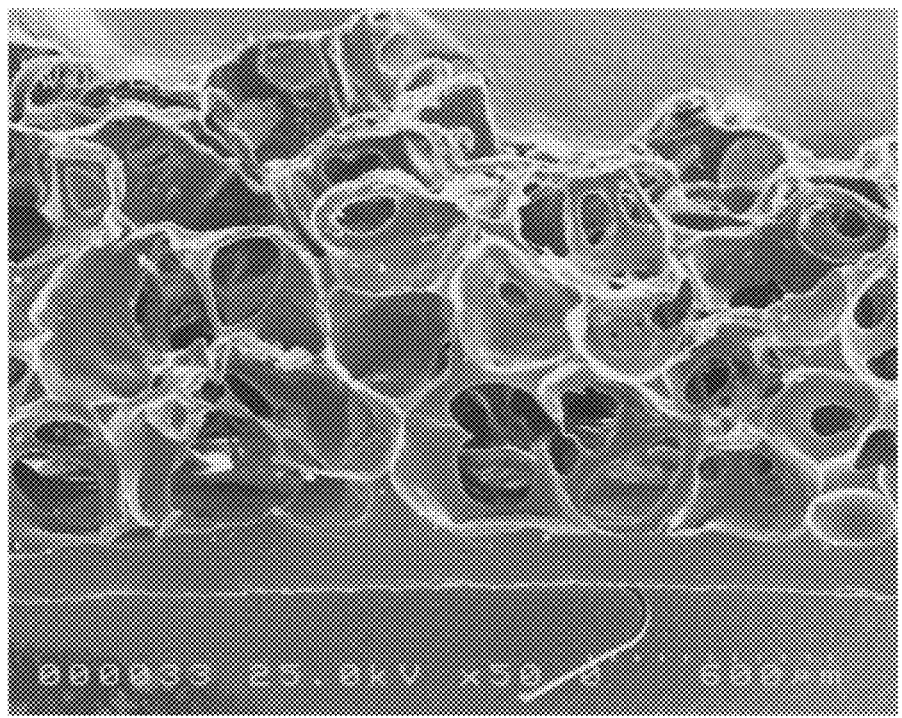

A sample from the implant was characterized by microCT analysis. This analysis revealed that the porous material was about 1.4 mm to about 1.6 mm in thickness with a porosity of about 80%, with open pores comprising at least 80% and close pores comprising at most 0.07%. The mean strut thickness was about 90 μm, with a mean pore size of about 400 μm. The porous material has a compressive modulus of about 20 kPa, elongation at break of about 350%, and a tensile strength of about 14 μPa. Scanning electron microscope images of the porous material are shown in FIGS. 2A and 2B.

To increase the thickness of the porous material covering the base layer, multiple dippings were performed to produce a mandrel coated with multiple layers of an uncured silicone/porogen mixture. Dippings were repeated until the desired thickness is achieved.

Example 6

A Method of Making an Implant Comprising a Porous Material

This example illustrates how to make an implant comprising a porous material of about 1 mm to about 2.5 mm in thickness formed using the porogen compositions disclosed herein.

A mandrel comprising a base layer of elastomer was prepared as described in Example 3.

To coat the base layer with a mixture comprising a matrix material and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 μm and a polyethylene glycol shell of about 53 μm until the maximum amount of porogens were absorbed into the uncured silicone. In other experiments, the porogen composition used were porogens comprising a sugar core of about 335 μm and a polyethylene glycol shell of about 60 μm, porogens comprising a sugar core of about 390 μm and a polyethylene glycol shell of about 83 μm, or porogens comprising a sugar core of about 460 μm and a polyethylene glycol shell of about 104 μm. The mandrel with the uncured silicon/porogen mixture coating was air dried for about 60 minutes to allow the xylene to evaporate. After xylene evaporation, the mandrel coated with the uncured silicone/porogen mixture was dipped first in about 35% (w/w) silicone in xylene, air dried to allow xylene evaporation (about 3 minutes), and then dipped in porogen composition until the maximum amount of porogens were absorbed into the uncured silicone. The mandrel with the second coating of uncured silicon/porogen mixture was air dried for about 60 minutes to allow the xylene to evaporate.

The mandrel comprising the two coats of uncured silicone/porogen mixture was treating as described in Example 3.

Removal of the porogen scaffold was as described in Example 5, and the resulting implant comprising a porous material of about 1 mm to about 2.5 mm was dried in an oven of about 126° C. for 30 minutes. This process resulted in a biocompatible implantable device comprising a porous material as disclosed herein.

Figure 2C:
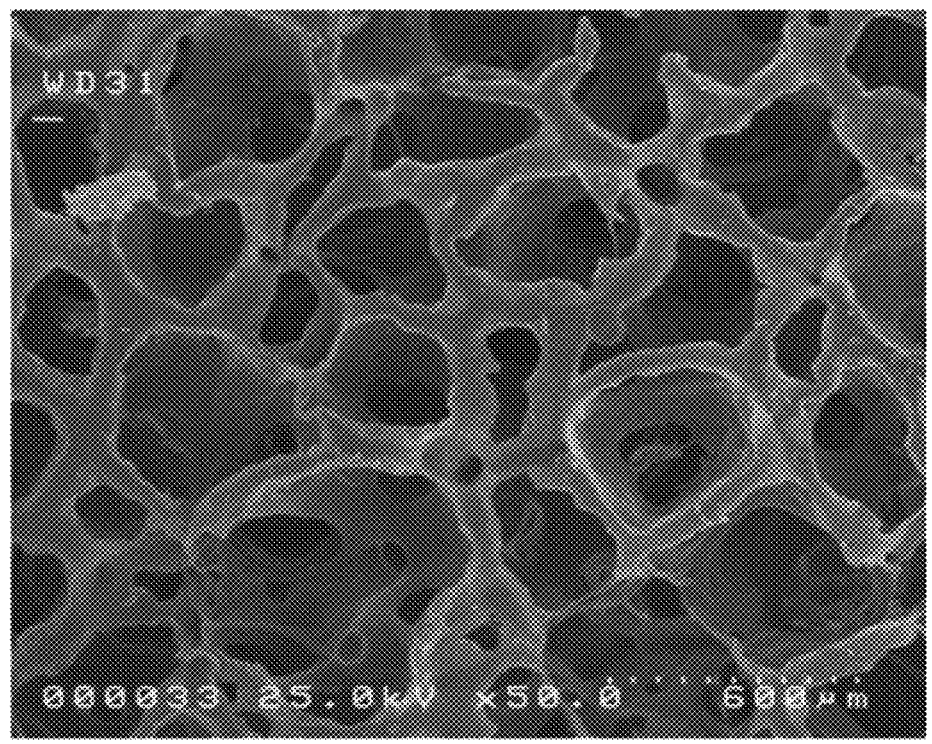
Figure 2D:
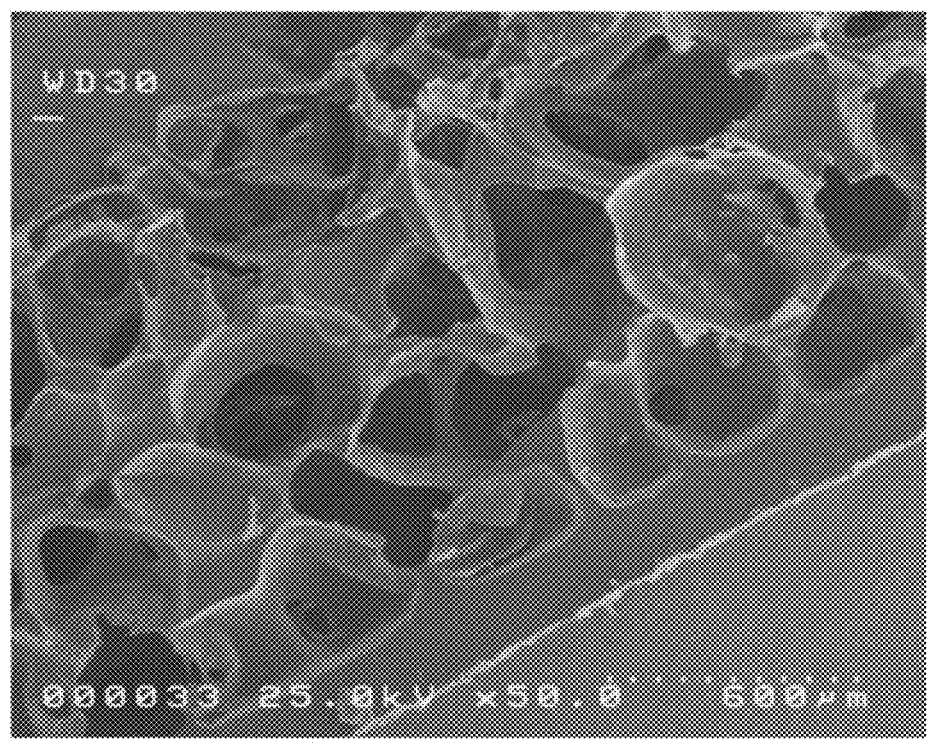

A sample from the implant was characterized by microCT analysis. This analysis revealed that the porous material was about 1.0 mm to about 3.0 mm in thickness with a porosity of about 85%, with open pores comprising at least 80% and close pores comprising at most 10%. The mean strut thickness was about 90 μm, with a mean pore size of about 400 μm. The porous material has a compressive modulus of about 20 kPa, elongation at break of about 300%, and a tensile strength of about 14 μPa. Scanning electron microscope images of the porous material are shown in FIGS. 2C and 2D.

Example 7

A Method of Making an Implant Comprising a Porous Material

This example illustrates how to make an implant comprising a porous material of about 2.5 mm to about 4.5 mm in thickness formed using the porogen compositions disclosed herein.

A mandrel comprising a base layer of elastomer was prepared as described in Example 3.

To coat the base layer with a mixture comprising a matrix material and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 μm and a polyethylene glycol shell of about 53 μm until the maximum amount of porogens were absorbed into the uncured silicone. In other experiments, the porogen composition used were porogens comprising a sugar core of about 335 μm and a polyethylene glycol shell of about 60 μm, porogens comprising a sugar core of about 390 μm and a polyethylene glycol shell of about 83 μm, or porogens comprising a sugar core of about 460 μm and a polyethylene glycol shell of about 104 μm. The mandrel with the uncured silicon/PGLA coating was air dried for about 60 minutes to allow the xylene to evaporate. After xylene evaporation, the mandrel coated with the uncured silicone/porogen mixture was dipped first in about 35% (w/w) silicone in xylene, air dried to allow xylene evaporation (about 3 minutes), and then dipped in the porogen composition until the maximum amount of porogens were absorbed into the uncured silicone. The mandrel with the second coating of uncured silicon/porogen mixture was air dried for about 60 minutes to allow the xylene to evaporate. After xylene evaporation, the mandrel coated with the two layers of the uncured silicone/porogen mixture was dipped first in about 32% (w/w) silicone in xylene, air dried to allow xylene evaporation (about 3 minutes), and then dipped in the porogen composition until the maximum amount of porogens were absorbed into the uncured silicone. The mandrel with the third coating of uncured silicon/porogen mixture was air dried for about 60 minutes to allow the xylene to evaporate.

The mandrel comprising the three coats of uncured silicone/porogen mixture was treating as described in Example 3.

Removal of the porogen scaffold was as described in Example 5, and the resulting implant comprising a porous material of about 2.5 mm to about 4.5 mm was air dried at an ambient temperature of about 18° C. to about 22° C. This process resulted in a biocompatible implantable device comprising a porous material as disclosed herein.

Figure 2E:
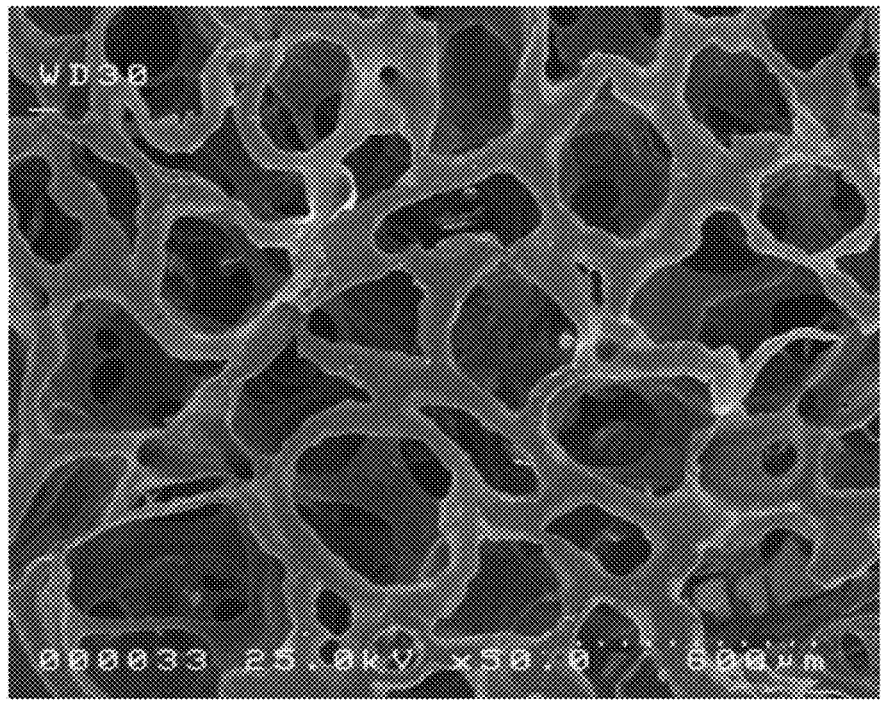
Figure 2F:
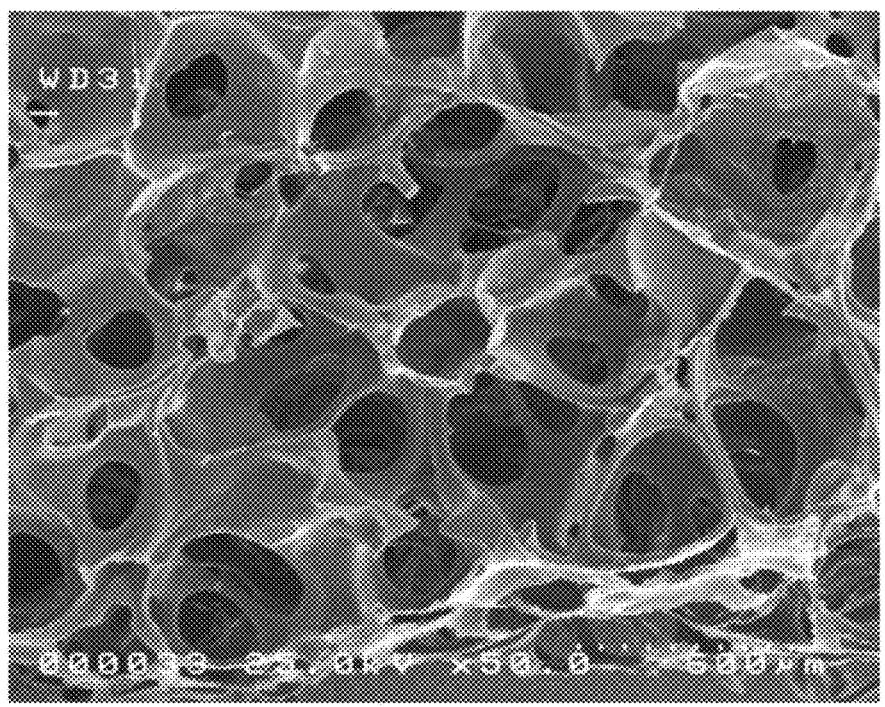

A sample from the implant was characterized by microCT analysis. This analysis revealed that the porous material was about 2.0 mm to about 3.0 mm in thickness with a porosity of about 80%, with open pores comprising at least 75% and close pores comprising at most 25%. The mean strut thickness was about 100 μm, with a mean pore size of about 90 μm. Scanning electron microscope images of the porous material are shown in FIGS. 2E and 2F.

Example 8

A Method of Making an Implant Comprising a Porous Material

This example illustrates how to make an implant comprising a porous material of about 3.5 mm to about 5.5 mm in thickness formed using the porogen compositions disclosed herein.

A mandrel comprising a base layer of elastomer was prepared as described in Example 3.

To coat the base layer with a mixture comprising a matrix material and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 μm and a polyethylene glycol shell of about 53 μm until the maximum amount of porogens were absorbed into the uncured silicone. In other experiments, the porogen composition used were porogens comprising a sugar core of about 335 μm and a polyethylene glycol shell of about 60 μm, porogens comprising a sugar core of about 390 μm and a polyethylene glycol shell of about 80 μm, or porogens comprising a sugar core of about 460 μm and a polyethylene glycol shell of about 104 μm. The mandrel with the uncured silicon/porogen mixture coating was air dried for about 60 minutes to allow the xylene to evaporate. After xylene evaporation, the mandrel coated with the uncured silicone/porogen mixture was dipped first in about 35% (w/w) silicone in xylene, air dried to allow xylene evaporation (about 3 minutes), and then dipped in the porogen composition until the maximum amount of porogens were absorbed into the uncured silicone. The mandrel with the second coating of uncured silicon/porogen mixture was air dried for about 60 minutes to allow the xylene to evaporate. After xylene evaporation, the mandrel coated with the two layers of the uncured silicone/porogen mixture was dipped first in about 32% (w/w) silicone in xylene, air dried to allow xylene evaporation (about 3 minutes), and then dipped in the porogen composition until the maximum amount of porogens were absorbed into the uncured silicone. The mandrel with the third coating of uncured silicon/porogen mixture was air dried for about 60 minutes to allow the xylene to evaporate. After xylene evaporation, the mandrel coated with the three layers of the uncured silicone/porogen mixture was dipped first in about 28% (w/w) silicone in xylene, air dried to allow xylene evaporation (about 3 minutes), and then dipped in the porogen composition until the maximum amount of porogens were absorbed into the uncured silicone. The mandrel with the fourth coating of uncured silicon/porogen mixture was air dried for about 60 minutes to allow the xylene to evaporate.

The mandrel comprising the four coats of uncured silicone/porogen mixture was treating as described in Example 3.

Figure 2G:
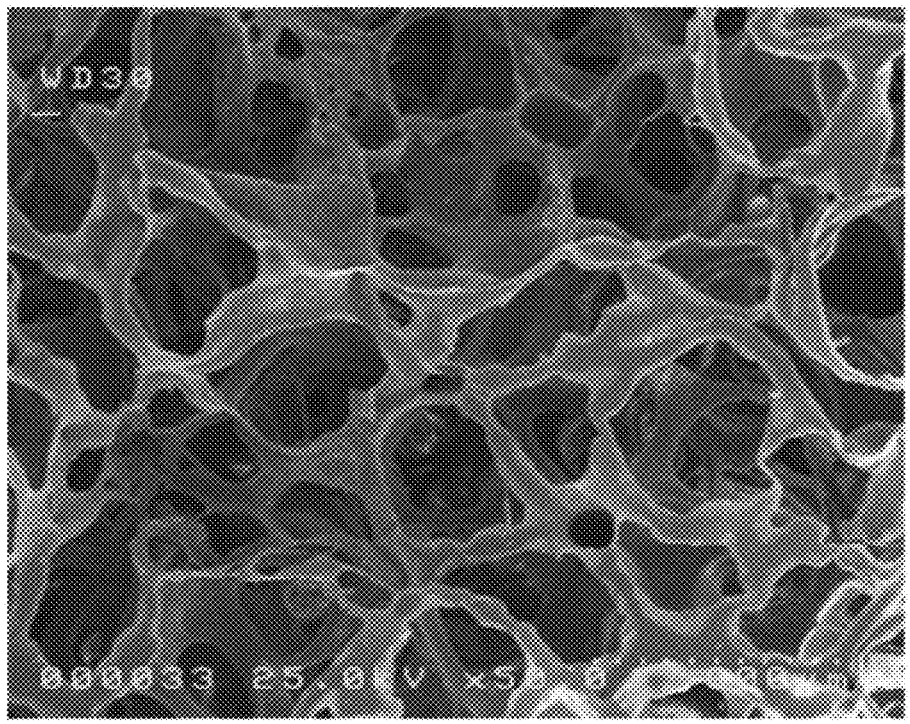
Figure 2H:
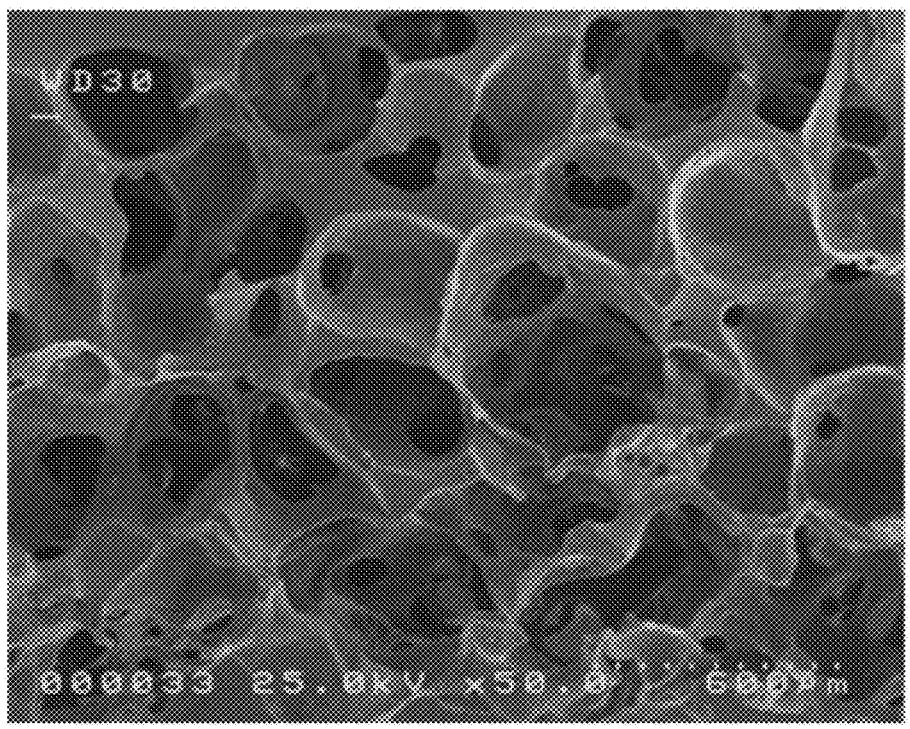

Removal of the porogen scaffold was as described in Example 5, and the resulting implant comprising a porous material of about 3.5 mm to about 5.5 mm was dried in an oven of about 126° C. for 30 minutes. This process resulted in a biocompatible implantable device comprising a porous material as disclosed herein. Scanning electron microscope images of the porous material are shown in FIGS. 2G and 2H.

Example 9

A Method of Making a Porous Material Comprising a Carbon-Based Elastomer

This example illustrates how to make a porous material comprising a rubber as disclosed herein.

To coat porogens with a carbon-based elastomer base, an appropriate amount of porogens comprising a sugar core of about 335 μm and a polyethylene glycol shell of about 15 μm is mixed with an appropriate amount of a carbon-based elastomer base, such as, e.g., poly(isoprene), poly(butadiene), poly(isobutylene isoprene), poly(butadiene acrylonitrile), and poly(chloroprene). The mixture is filtered through a 43 μm sieve to remove the excess rubber and is poured into about 20 cm×20 cm square mold coated with a non-stick surface.

To treat a carbon-based elastomer base-coated porogen mixture to allow fusing of the porogens to form a porogen scaffold and curing of the elastomer, the rubber/porogen mixture is placed into an oven and is heated at a temperature of about 75° C. for about 60 min, sulfur and zinc oxide are added, and then this mixture is heated to 126° C. for 75 minutes. After curing, the sheet of cured rubber-coated porogen scaffold is removed.

To remove a porogen scaffold from the cured carbon-based elastomer, the cured rubber/porogen scaffold was immersed in hot water. After about 30 minutes, the hot water was removed and the resulting 20 cm×20 cm×1.5 mm sheet of porous material was air dried at an ambient temperature of about 18° C. to about 22° C. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using any of the core/shell porogens disclosed herein. Similarly, porogen diameters from about 50 μm to about 3000 μm can be used. Likewise, the porous material may be affixed to another component in a manner similar to that described in Example 2. Similarly, the porous material may be shaped using a mold in a manner similar to that described in Example 3 and/or affixed to another component in a manner similar to that described in Example 4. Furthermore, the porous material may be part of a manufacturing process where it is integrated as a component in a manner similar to that described in Examples 5-8.

Example 10

A Method of Making a Porous Material Comprising a Poly(Vinyl)-Based Thermoplastic This example illustrates how to make a porous material comprising a thermoplastic as disclosed herein.

To coat porogens with an thermoplastic base, an appropriate amount of porogens comprising a sugar core of about 335 μm and a polyethylene glycol shell of about 15 μm is mixed with an appropriate amount of poly(vinyl)-based thermoplastic, such as, e.g., poly(vinyl chloride), poly(vinylidene fluoride), poly(vinyl fluoride), poly(vinyl nitrate), and poly-(4-vinylphenol). The mixture is filtered through a 43 μm sieve to remove the excess poly(vinyl)-based thermoplastic and is poured into about 20 cm×20 cm square mold coated with a non-stick surface.

To treat a thermoplastic-coated porogen mixture to allow fusing of the porogens to form a porogen scaffold and hardening of the thermoplastic, the poly(vinyl)-based thermoplastic/porogen mixture is placed into an oven and is heated at a temperature of 75° C. for 60 minutes, and then this mixture is heated to 120° C. for 30 minutes. The mixture is cooled to room temperature to allow hardening of the poly(vinyl)-based thermoplastic. After hardening, the sheet of hardened poly(vinyl)-based thermoplastic-coated porogen scaffold is removed.

To remove a porogen scaffold from the cured elastomer, the hardened poly(vinyl)-based thermoplastic/porogen scaffold is immersed in warm water. After 30 minutes, the water is removed and fresh warm water is added. After 30 minutes, the water is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using any of the core/shell porogens disclosed herein. Similarly, porogen diameters from about 50 μm to about 3000 μm can be used. Likewise, the porous material may be affixed to another component in a suitable manner. Similarly, the porous material may be shaped using a mold in a manner similar to that described in Example 3 and/or affixed to another component in a manner similar to that described in Example 4. Furthermore, the porous material may be part of a manufacturing process where it is integrated as a component in a manner similar to that described in Examples 5-8.

Example 11

A Method of Making a Porous Material Comprising Thermoplastic Elastomer

This example illustrates how to make a porous material comprising a thermoplastic elastomer as disclosed herein.

To coat porogens with an thermoplastic elastomer base, an appropriate amount of porogens comprising a sugar core of about 335 μm and a polyethylene glycol shell of about 15 μm is mixed with an appropriate amount of a thermoplastic elastomer, such as, e.g., poly(styrene-co-butadiene-polystyrene) (SBS). The mixture is filtered through a 43 μm sieve to remove the excess SBS and is poured into about 20 cm×20 cm square mold coated with a non-stick surface.

To treat a thermoplastic elastomer-coated porogen mixture to allow fusing of the porogens to form a porogen scaffold and curing of the thermoplastic elastomer, the SBS/porogen mixture is placed into an oven and is heated at a temperature of 75° C. for 60 minutes, and then this mixture is heated to 120° C. for 30 minutes. After curing, the sheet of hardened SBS-coated porogen scaffold is removed.

To remove a porogen scaffold from the cured elastomer, the hardened poly(vinyl)-based thermoplastic/porogen scaffold is immersed in warm water. After 30 minutes, the water is removed and fresh warm water is added. After 30 minutes, the water is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using any of the core/shell porogens disclosed herein. Similarly, porogen diameters from about 50 μm to about 3000 μm can be used. Likewise, the porous material may be affixed to another component in a manner similar to that described in Example 2. Similarly, the porous material may be shaped using a mold in a manner similar to that described in Example 3 and/or affixed to another component in a manner similar to that described in Example 4. Furthermore, the porous material may be part of a manufacturing process where it is integrated as a component of an article.

Example 12

A Method of Making a Porous Material Comprising a Thermoset Elastomer

This example illustrates how to make a porous material comprising a thermoset elastomer as disclosed herein.

To coat porogens with an thermoset elastomer base, an appropriate amount of porogens comprising a sugar core of about 335 μm and a polyethylene glycol shell of about 15 μm is mixed with an appropriate amount of a poly(urethane). The mixture is filtered through a 43 μm sieve to remove the excess poly(urethane) and is poured into about 20 cm×20 cm square mold coated with a non-stick surface.

To treat a thermoset elastomer-coated porogen mixture to allow fusing of the porogens to form a porogen scaffold and curing of the thermoset elastomer, the poly(urethane)/porogen mixture is placed into an oven and is heated at a temperature of 75° C. for 60 minutes, and then this mixture is heated at a temperature of 126° C. for 75 minutes. After curing, the sheet of cured poly(urethane)-coated porogen scaffold is removed.

To remove a porogen scaffold from the cured elastomer, the cured poly(urethane)/porogen scaffold is immersed in acetone or chloroform. After 30 minutes, the acetone or chloroform is removed and fresh acetone or chloroform is added. After 30 minutes, the acetone or chloroform is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using any of the core/shell porogens disclosed herein. Similarly, porogen diameters from about 50 µm to about 3000 µm can be used. Likewise, the porous material may be affixed to another component in a manner similar to that described in Example 2. Similarly, the porous material may be shaped using a mold in a manner similar to that described in Example 3 and/or affixed to another component in a manner similar to that described in Example 4. Furthermore, the porous material may be part of a manufacturing process where it is integrated as a component of an article.

Example 13

A Method of Making a Porogen Composition

This example illustrates how to make porogen compositions disclosed herein.

To make a porogen composition comprising a sugar core material and a polymer shell material, sugar particles suitable for a core material were purchased from Paular Corp, (Cranbury, N.J.). These sugar particles were sieved through an about 40 to about 60 mesh to separate particles of about 250 µm about 450 µm in size. To coat sugar core particles with a polymer, poly(ethylene glycol) was coated onto the sugar core material to a thickness of about 53 µm by fluidization using a fluid bed dryer. The resulting porogen compositions yielded porogens comprising a sugar core material of about 335 µm in diameter and a poly(ethylene glycol) shell material of about 53 µm in thickness.

To make a porogen composition comprising a polymer core material and a wax shell material, a polycaprolactone (PCL) core material will be made using a solvent evaporation process. Briefly, about 500 mL of a 30% (w/v) solution of PCL in dichloromethane will be poured into 3 L of a 6% (w/v) solution of poly(vinyl alcohol), MW 23000, with constant stirring. The mixture will be continuously stirred for enough time to allow methylene chloride to evaporate. The resulting PCL particles of core material will be filtered to remove debris and then will be washed with deionized water to remove the poly(vinyl alcohol). This process will result in about 100 g of PCL particles of core material with a mean diameter of about 400 µm to about 500 µm. To coat polymer core particles with a wax, paraffin will be coated onto the PCL core material to a thickness of about 50 µm by fluidization using a fluid bed dryer. The resulting porogen compositions will yield porogens comprising a polymer core material of about 450 µm in diameter and a paraffin shell material of about 50 µm in thickness.

To make a porogen composition comprising a salt core material and a surfactant shell material, sodium chloride particles suitable for a core material will be purchased from a commercial supplier. These salt particles will be sieved through an about 40 to about 60 mesh to separate particles of about 250 µm about 450 µm in size. To coat salt core particles with a surfactant, polysorbate 20 will be coated onto the salt core material to a thickness of about 15 µm by fluidization using a fluid bed dryer. The resulting porogen compositions will yield porogens comprising a salt core material of about 350 µm in diameter and a polysorbate 20 shell material of about 15 µm in thickness.

To make a porogen composition comprising a PGLA (50:50) core and a PCL shell material, PGLA (50:50) and poly-caprolactone (PCL) were co-dissolved in methylene chloride, where at least 2 parts of PGLA (50:50) and at most at 1 part of PCL were dissolved in methylene chloride. Solvent evaporation was applied to form microparticles. A PGLA (50:50) core with PCL shell was formed by annealing the microparticles at 60° C. to allow phase separation between PGLA and PCL. About 500 mL of a 30% (w/v) solution of PGLA (50:50) and PCL in dichloromethane was poured into 3 L of a 6% (w/v) solution of poly(vinyl alcohol), MW 23000, with constant stirring until the methylene chloride evaporated. The resulting particles in polyvinyl alcohol dispersions were heated at 60° C. to allow phase separation between PGLA (50:50) and PCL. After cooling down, the microparticles were filtered to remove debris and then washed with deionized water to remove the poly(vinyl alcohol). This process resulted in about 100 g of a PGLA (50:50) core and PCL shell composition with a mean diameter of about 400 µm to about 500 µm.

It can be appreciated that porous materials are provided by the present invention, which can be designed and manufactured with a high degree of precision. The present invention provides such materials that have numerous industrial, household and medical uses. For example, porous materials in the biomedical field are provided which can be components of devices and articles useful for tissue engineering/regeneration, wound dressings, drug release matrices, membranes for separations and filtration, sterile filters, artificial kidneys, absorbents, hemostatic devices, and the like. In various industrial and household applications, porous materials are provided which can make up insulating materials, packaging materials, impact absorbers, liquid or gas absorbents, and wound dressings. The material provided also can be used as components of personal hygiene products, such as but not limited to cleaning and cleansing pads, wipes and swabs, deodorant, disposable towels, dry shampoo, facial tissues, handkerchiefs, hygiene wipes, paper towels, shaving brushes, tampons, towels, underarm liners, washing mitts, and wet wipes, membranes, filters and so forth. Many other uses are contemplated for the present materials and are considered to be within the scope of the invention. In some embodiments of the invention, the porous materials are silicone elastomers having well defined pore size, shape and interconnectivity.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of making a porous material, the method comprising the steps of:
   a) coating porogens with a matrix material to form a matrix material-coated porogen mixture, the porogens comprising a shell material and a core material, wherein the core material is a sugar and the shell material is polyethylene glycol, and further wherein the shell material has a melting temperature that is lower than a melting temperature of the core material;
   b) treating the matrix material-coated porogen mixture to form a porogen scaffold comprising fused porogens and stabilized matrix material; and
   c) removing the porogen scaffold from the stabilized matrix material, wherein porogen scaffold removal results in a porous material, the porous material comprising a matrix defining an array of interconnected pores.

2. The method of claim 1 wherein the porous material is a porous silicone elastomer.

3. The method of claim 1 wherein the step of treating comprises heat treatment.

4. The method of claim 1 wherein the matrix material is a silicone dispersion.

5. A method of making a porous material, the method comprising the steps of:
   a) coating porogens with a matrix material to form a matrix material-coated porogen mixture, the porogens comprising a shell material and a core material, wherein the shell material has a melting temperature that is lower than a melting temperature of the core material;
   b) treating the matrix material-coated porogen mixture to form a porogen scaffold comprising fused porogens and stabilized matrix material; and
   c) removing the porogen scaffold from the stabilized matrix material, wherein porogen scaffold removal results in a porous material, the porous material comprising a matrix defining an array of interconnected pores;
   wherein the porous material is a porous silicone elastomer.

6. The method of claim 5 wherein the step of treating comprises heat treatment.

* * * * *